US010988811B2

(12) United States Patent
Olsson et al.

(10) Patent No.: US 10,988,811 B2
(45) Date of Patent: Apr. 27, 2021

(54) MARKER GENES FOR COLORECTAL CANCER CLASSIFICATION, METHOD FOR JUDGING LYMPH NODE METASTASIS FOR PROGNOSIS OF COLORECTAL CANCER AND KIT THEREFOR

(71) Applicant: HiloProbe AB, Umeå (SE)

(72) Inventors: Lina Olsson, Umeå (SE); Sten Hammarström, Stockholm (SE); Marie-Louise Hammarström, Umeå (SE); Gudrun Lindmark, Helsingborg (SE); Anne Israelsson, Umeå (SE)

(73) Assignee: HiloProbe AB, Umeå (SE)

( * ) Notice: Subject to any disclaimer, the term of this patent is extended or adjusted under 35 U.S.C. 154(b) by 0 days.

(21) Appl. No.: 16/093,013

(22) PCT Filed: Apr. 12, 2017

(86) PCT No.: PCT/SE2017/050368
§ 371 (c)(1),
(2) Date: Oct. 11, 2018

(87) PCT Pub. No.: WO2017/184059
PCT Pub. Date: Oct. 26, 2017

(65) Prior Publication Data
US 2019/0136328 A1 May 9, 2019

(30) Foreign Application Priority Data
Apr. 20, 2016 (SE) ..................................... 1630095-6

(51) Int. Cl.
C12Q 1/6886 (2018.01)
C12Q 1/68 (2018.01)
(52) U.S. Cl.
CPC ............. *C12Q 1/6886* (2013.01); *C12Q 1/68* (2013.01); *C12Q 2600/112* (2013.01); *C12Q 2600/118* (2013.01); *C12Q 2600/158* (2013.01)
(58) Field of Classification Search
None
See application file for complete search history.

(56) References Cited

U.S. PATENT DOCUMENTS

| 6,773,882 B2 * | 8/2004 | Hogan | C12Q 1/6895 435/471 |
|---|---|---|---|
| 2010/0009905 A1 | 1/2010 | Macina | |
| 2011/0071049 A1 * | 3/2011 | Heintz | C12N 15/111 506/9 |
| 2012/0015904 A1 * | 1/2012 | Sharp | A61K 31/37 514/56 |
| 2013/0317043 A1 | 11/2013 | Wagner et al. | |

FOREIGN PATENT DOCUMENTS

| WO | 2009/057849 | 5/2009 |
|---|---|---|
| WO | 2011/018435 | 2/2011 |
| WO | 2013/033609 | 3/2013 |
| WO | 2013/033629 | 3/2013 |
| WO | 2013/052480 | 4/2013 |
| WO | 2015/120069 | 8/2015 |

OTHER PUBLICATIONS

Diffenbach (PCR methods and Applications (1993) vol. 3, pp. S30-S37) (Year: 1993).*
Roux et al (PCR Methods and Applications (1995) vol. 4, pp. s185-s194) (Year: 1995).*
Chang G. J. et al. "Lymph Node Evaluation and Survival After Curative Resection of Colon Cancer: Systematic Review" J. Natl. Cancer Inst., vol. 99, Iss. 6, pp. 433-441 (2007).
Iddings et al., "The Biologic Significance of Micrometastatic Disease and Sentinel Lymph Node Technology on Colorectal Cancer*" J. Surg. Oncol., vol. 96, Iss. 8, pp. 671-677 (2007).
Nicastri et al., "Is Occult Lymph Node Disease in Colorectal Cancer Patients Clinically Significant?" J. Mol. Diagn., vol. 9, p. 563-571 (2007).
Bockelman et al., "Risk of recurrence in patients with colon cancer stage II and III: A systematic review and meta-analysis of recent literature," Acta Oncol., vol. 54, Iss. 1, pp. 5-16 (2015).
Tsai et al., "Factors affecting number of lymph nodes harvested and the impact of examining a minimum of 12 lymph nodes in stage I-III colorectal cancer patients: a retrospective single institution cohort study of 1167 consecutive patients," BMC Surg., vol. 16, p. 17 (2016).
Parnaby C. N. et al, Br. J. Cancer, vol. 113, pp. 212-219 (2015).
Ohlsson L. et al., "Lymph node tissue kallikrein-related peptidase 6 mRNA: a progression marker for colorectal cancer," Br. J. Cancer, vol. 107, pp. 150-157 (2012).
Ohlsson L. et al., "Lymph node CEA and MUC2 mRNA as useful predictors of outcome in colorectal cancer" Int. J. Cancer, vol. 130, Iss. 8, pp. 1833-1843 (2012).
Ohlsson L. et al., "Biomarker selection for detection of occult tumour cells in lymph nodes of colorectal cancer patients using real-time quantitative RT-PCR," Br. J. Cancer, vol. 95, pp. 218-225 (2006).
Ohlsson, "Biomarker mRNAs for staging and prognosis of colorectal cancer," Department of Clinical Microbiology, Immunology, Thesis, pp. 1-86, ISBN 978-91-7459-318-1 (2011).

(Continued)

*Primary Examiner* — Katherine D Salmon
(74) *Attorney, Agent, or Firm* — Grüneberg and Myers PLLC

(57) ABSTRACT

A group of molecular biomarkers having the genes SLC35D3, POSTN, KLK6 and MUC2 can be used in objective and quantitative methods for the classification, prediction of prognosis and for guiding treatment decisions of a subject with colorectal cancer. More specifically, a method for determining the metastatic potential and/or tumor aggressiveness of a colorectal cancer in a subject can include determining the gene expression levels of genes SLC35D3, POSTN, KLK6 and/or MUC2 in a regional lymph node, a primary intestinal tumor, blood, or feces sample obtained from the subject.

6 Claims, 5 Drawing Sheets

Figure 1:
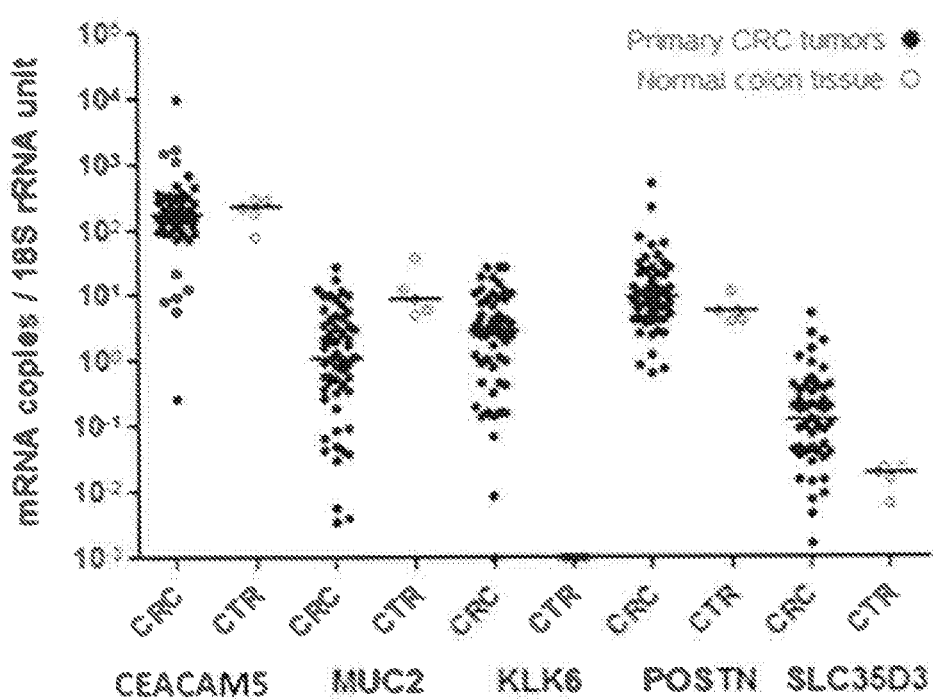

Specification includes a Sequence Listing.

(56) References Cited

OTHER PUBLICATIONS

Byrd et al., "Mucins and mucin binding proteins in colorectal cancer" Cancer Metastasis Review, vol. 23, pp. 77-99 (2004).
Bas et al., "Utility of the Housekeeping Genes 18S rRNA, b-Actin and Glyceraldehyde-3-Phosphate-Dehydrogenase for Normalization in Real-Time Quantitative Reverse Transcriptase-Polymerase Chain Reaction Analysis of Gene Expression in Human T Lymphocytes" Scand. J. Immunol., vol. 59, Iss. 6, pp. 566-573 (2004).
Fahlgren et al., "Increased expression of antimicrobial peptides and lysozyme in colonic epithelial cells of patients with ulcerative colitis" Clin. Exp. Immunol., vol. 131, Iss. 1, pp. 90-101 (2003).
Chomczynski et al., "Single-Step Method of RNA Isolation by Acid Guanidinium Thiocyanate-Phenol-Chloroform Extraction," Analytical Biochemistry, vol. 162, pp. 156-159 (1987).
Ben et al., "Circulating levels of periostin may help identify patients with more aggressive colorectal cancer," International Journal of Oncology, vol. 34, pp. 821-828 (2009).
Bao et al., "Periostin potently promotes metastatic growth of colon cancer by augmenting cell survival via the Akt/PKB pathway," Cancer Cell, vol. 5, No. 4, pp. 329-339 (2004).
Reiner et al., "Identifying differentially expressed genes using false discovery rate controlling procedures" Bioinformatics, vol. 19, pp. 368-375 (2003).
International Search Report mailed in PCT/SE2017/050368 dated Jul. 10, 2017.
Written Opinion of the International Searching Authority mailed in PCT/SE2017/050368 dated Jul. 10, 2017.

\* cited by examiner

SEQUENCE LISTING

<160> NUMBER OF SEQ ID NOS: 32

<210> SEQ ID NO 1
<211> LENGTH: 19
<212> TYPE: DNA
<213> ORGANISM: Homo sapiens

<400> SEQUENCE: 1
agcactcccg tgacgtacc                                     19

<210> SEQ ID NO 2
<211> LENGTH: 17
<212> TYPE: DNA

<213> ORGANISM: Homo sapiens

<400> SEQUENCE: 2
tcatcaccac ctgcggc                                                    17

<210> SEQ ID NO 3
<211> LENGTH: 18
<212> TYPE: DNA
<213> ORGANISM: Homo sapiens

<400> SEQUENCE: 3
cctggcagga gccggcga                                                   18

<210> SEQ ID NO 4
<211> LENGTH: 21
<212> TYPE: DNA
<213> ORGANISM: Homo sapiens

<400> SEQUENCE: 4
cccttgctta ctccctttct c                                               21

<210> SEQ ID NO 5
<211> LENGTH: 24
<212> TYPE: DNA
<213> ORGANISM: Homo sapiens

<400> SEQUENCE: 5
acagctcaga gtcttcgtat atcg                                            24

<210> SEQ ID NO 6
<211> LENGTH: 17
<212> TYPE: DNA
<213> ORGANISM: Homo sapiens

<400> SEQUENCE: 6
acagctgtct gcattga                                                    17

<210> SEQ ID NO 7
<211> LENGTH: 19
<212> TYPE: DNA
<213> ORGANISM: Homo sapiens

<400> SEQUENCE: 7
aaggttatgc ttccccagg                                                  19

<210> SEQ ID NO 8
<211> LENGTH: 21
<212> TYPE: DNA
<213> ORGANISM: Homo sapiens

<400> SEQUENCE: 8
cttatccatc cactgtgggt c                                               21

<210> SEQ ID NO 9
<211> LENGTH: 27
<212> TYPE: DNA
<213> ORGANISM: Homo sapiens

<400> SEQUENCE: 9
cactgcaaaa aaccgaatct tcaggtc                                         27

<210> SEQ ID NO 10
<211> LENGTH: 21

```
<212> TYPE: DNA
<213> ORGANISM: Homo sapiens

<400> SEQUENCE: 10
tagtgtccag ctccagcatg a                                              21

<210> SEQ ID NO 11
<211> LENGTH: 21
<212> TYPE: DNA
<213> ORGANISM: Homo sapiens

<400> SEQUENCE: 11
aagagcgatg cctacaccaa a                                              21

<210> SEQ ID NO 12
<211> LENGTH: 16
<212> TYPE: DNA
<213> ORGANISM: Homo sapiens

<400> SEQUENCE: 12
tcccggttcc acatga                                                    16

<210> SEQ ID NO 13
<211> LENGTH: 24
<212> TYPE: DNA
<213> ORGANISM: Homo sapiens

<400> SEQUENCE: 13
tgtagctgtt gcaaatgctt taag                                           24

<210> SEQ ID NO 14
<211> LENGTH: 24
<212> TYPE: DNA
<213> ORGANISM: Homo sapiens

<400> SEQUENCE: 14
ctgatatagc agccctggtg tagt                                           24

<210> SEQ ID NO 15
<211> LENGTH: 18
<212> TYPE: DNA
<213> ORGANISM: Homo sapiens

<400> SEQUENCE: 15
aggaagactg acagttgt                                                  18

<210> SEQ ID NO 16
<211> LENGTH: 17
<212> TYPE: DNA
<213> ORGANISM: Homo sapiens

<400> SEQUENCE: 16
ccgctcccaa gatccaa                                                   17

<210> SEQ ID NO 17
<211> LENGTH: 23
<212> TYPE: DNA
<213> ORGANISM: Homo sapiens

<400> SEQUENCE: 17
gtaattccag ctccaatagc gta                                            23

<210> SEQ ID NO 18
```

-continued

```
<211> LENGTH: 15
<212> TYPE: DNA
<213> ORGANISM: Homo sapiens

<400> SEQUENCE: 18
ctgcagttaa aaagc                                                          15

<210> SEQ ID NO 19
<211> LENGTH: 19
<212> TYPE: DNA
<213> ORGANISM: Homo sapiens

<400> SEQUENCE: 19
cagcactccc gtgacgtac                                                      19

<210> SEQ ID NO 20
<211> LENGTH: 17
<212> TYPE: DNA
<213> ORGANISM: Homo sapiens

<400> SEQUENCE: 20
catcggcgtc ctggttc                                                        17

<210> SEQ ID NO 21
<211> LENGTH: 16
<212> TYPE: DNA
<213> ORGANISM: Homo sapiens

<400> SEQUENCE: 21
tggatcacag cccgga                                                         16

<210> SEQ ID NO 22
<211> LENGTH: 18
<212> TYPE: DNA
<213> ORGANISM: Homo sapiens

<400> SEQUENCE: 22
tacacctcgg gccacttg                                                       18

<210> SEQ ID NO 23
<211> LENGTH: 18
<212> TYPE: DNA
<213> ORGANISM: Homo sapiens

<400> SEQUENCE: 23
ccgggctgct cattgaga                                                       18

<210> SEQ ID NO 24
<211> LENGTH: 19
<212> TYPE: DNA
<213> ORGANISM: Homo sapiens

<400> SEQUENCE: 24
tggctaggat ggtctcgat                                                      19

<210> SEQ ID NO 25
<211> LENGTH: 21
<212> TYPE: DNA
<213> ORGANISM: Homo sapiens

<400> SEQUENCE: 25
ggacctatgc ctgttttgtc t                                                   21
```

```
<210> SEQ ID NO 26
<211> LENGTH: 20
<212> TYPE: DNA
<213> ORGANISM: Homo sapiens

<400> SEQUENCE: 26
cgctcccaag atccaactac                                                  20

<210> SEQ ID NO 27
<211> LENGTH: 3420
<212> TYPE: DNA
<213> ORGANISM: Homo sapiens
<220> FEATURE:
<223> OTHER INFORMATION: SLC35D3

<400> SEQUENCE: 27
agtcggacgc agagctgcct aaccgcaaga acgcctggcc ggagctgccc tctgcagccg      60
agccggcgcc ccctgccctt cgccgccgcg ctgggcgggc gccccgccg ccctcactcc      120
gctgctcccg gctcctcgcg cgcaggtcgc ggagctccgc caccgctggg tgcggcgagg      180
ccggcgcgat gcggcagctg tgccggggcc gcgtgctggg catctcggtg gccatcgcgc      240
acggggtctt ctcgggctcc ctcaacatct tgctcaagtt cctcatcagc cgctaccagt      300
tctccttcct gaccctggtg cagtgcctga ccagctccac cgcggcgctg agcctggagc      360
tgctgcggcg cctcgggctc atcgccgtgc ccccttcgg tctgagcctg gcgcgctcct      420
tcgcggggt cgcggtgctc tccacgctgc agtccagcct cacgctctgg tccctgcgcg      480
gcctcagcct gcccatgtac gtggtcttca agcgctgcct gccctggtc accatgctca      540
tcggcgtcct ggtgctcaag aacggcgcgc cctcgccagg ggtgctggcg gcggtgctca      600
tcaccacctg cggcgccgcc ctggcaggtg agcgggcccc cgcgccgacc ccagccgac      660
cccacccacc ccgctccgtc gggcagagac cgcggggatc actgagttca acgacctcac      720
ttccagatgg ggagactgag gcagagagag ccggagagct ttgagagtgg tcgctcagct      780
cgcaaaaggg acttccgaga cccagagagc tccccagcgc cccaccaagt cccctgccc       840
cctaatgtcc tggcttccga ccctcgccca tgcttcaccc ggcatcgccc ttcctgtcgc      900
cccctctcct ggtcttcccc tgtcacccca ttctccggga gaggtgggag ggccgcctga      960
gcctgggagc tggagtcctc caagcctgga ccaagccgga aggagggggc cgtgaacttc     1020
cttgggtcac gaggggctgg aatggaggtg ggggatgggg gcgaagctga gggttcccgg     1080
ggctactgcg gggtgtctcg tgctgcgcag ggggctgcgg ccctgggcca gacgacccag     1140
gtgctgagcg agacgagagc ctgggcaggg ggaagcttca ctgggggcca gaacaggcgt     1200
tctccccgc gcctggcccg ctccgggttg caggccactg gctggggctc cctctccctt     1260
tggtgcccca cggggcaggg gctccggggt gcaggtacca cgccgcccaag tgacctcggt     1320
gccagctcgg ggaagccaca gcacctgccc cgagggcatc tgcgctctcc ggggcctttg     1380
tcttggacag aggaagatgg agtgacccgg ggatatggcg ggaaggcgct ctgagcactg     1440
agtttggctg tcgcatttga cacgggtggc cgagggacgg cgggcgtctg tcactcagga     1500
atccggtggg cagagctggg gcgcgaaccc agtctccttt cctacccgac gcgttttccc     1560
cgtgggtccc cgcccacgcc aacctgctgt cttctctctt tttccttccc gcccgggctc     1620
ggccgtcctc ctcgtgcgcc gcaggagccg gcgacctgac gggcgacccc atcgggtacg     1680
tcacgggagt gctggcggtg ctggtgcacg ctgcctacct ggtgctcatc cagaaggcca     1740
gcgcagacac cgagcacggg ccgctcaccg cgcagtacgt catcgccgtc tctgccaccc     1800
```

| | |
|---|---|
| cgctgctggt catctgctcc ttcgccagca ccgactccat ccacgcctgg accttcccgg | 1860 |
| gctggaagga cccggccatg gtctgcatct tcgtggcctg catcctgatc ggctgcgcca | 1920 |
| tgaacttcac cacgctgcac tgcacctaca tcaattcggc cgtgaccacc agcttcgtgg | 1980 |
| gtgtggtgaa gagcatcgcc accatcacgg tgggcatggt ggccttcagc gacgtggagc | 2040 |
| ccacctctct gttcattgcc ggcgtggtgg tgaacaccct gggctctatc atttactgtg | 2100 |
| tggccaagtt catggagacc agaaagcaaa gcaactacga ggacctggag gcccagcctc | 2160 |
| ggggagagga ggcgcagcta agtggagacc agctgccgtt cgtgatggag gagctgcccg | 2220 |
| ggagggagg aaatggccgg tcagaaggtg gggaggcagc aggtggcccc gctcaggaga | 2280 |
| gcaggcaaga ggtcaggggc agcccccgag gagtcccgct ggtggctggg agctctgaag | 2340 |
| aagggagcag gaggtcgtta aaagatgctt acctcgaggt atggaggttg gttaggggaa | 2400 |
| ccaggtatat gaagaaggat tatttgatag aaaacgagga gttacccagt ccttgagaag | 2460 |
| gaggtgcatg tacgtaccta tgtgcataca cttattttat atgttagaaa tgacgtgttt | 2520 |
| taatgagagg cctccccgtt ttattctttg aggagtgggg aagggaagaa agaaagaag | 2580 |
| ctgaaaggta ctgacacaga gcaacaaaat tagcacctgt gtgaattatt tagtgtgact | 2640 |
| tcacctgagg catcacagag acaaagaat gtgaagctac ttaacaaagt aaggcaacgt | 2700 |
| ttctgcttca gactcctggc acatttactt tttgtcatta taaccataac taaatatctg | 2760 |
| catgtaccaa gagtccctaa gccaccccct ccaaagatgg agtgtagaaa tgatgacagc | 2820 |
| acttagtaag ttcaaagatg acattcaggg atgcattttt tgatgataga actcagtttt | 2880 |
| ttatcgccag ctgggcaaag agtatattgc tgaaatgata tataaatata ttgaattgat | 2940 |
| gtttactgtt tatagtcatc tgaaatatca tatttactct gattctactc acttgttttt | 3000 |
| taaaaataag tgtcctatta ttgtattata tattgataga aactgttaaa gctattttga | 3060 |
| aaatatgagt tcttagcttt aatcatgaag tctgaagttt gctttcagta attattttaa | 3120 |
| aagttgtttt ggttcattgc tttataatat ttattattga atgccaaacc tgttcttttt | 3180 |
| tttactgtgt ccaatattct ttcaagcaaa tgcaatggct ggaatataat tcagaattaa | 3240 |
| ctgaaaccca gccagaagag ggaccacctg taaagcaagt cctttcaagt ttcactgcac | 3300 |
| atcccaaacc atgttacaaa aagagcaact gctatattca cattatgata ttttctatc | 3360 |
| ttaaatttgt caaaataaag tatgagtcta actattaaag gatacattgt tagaaattta | 3420 |

<210> SEQ ID NO 28
<211> LENGTH: 36263
<212> TYPE: DNA
<213> ORGANISM: Homo sapiens
<220> FEATURE:
<223> OTHER INFORMATION: POSTN

<400> SEQUENCE: 28

| | |
|---|---|
| taatttcatt caatttcctt taatgagtac ttgttacagt aaaagaggta taaagtcctg | 60 |
| ttcccaagtc caaaccactt tttaacttaa atcttgagtt tttctgaatt actcaatttg | 120 |
| aagtaattct ctttatatct gaaaaatggt tttattgaaa cgtttgagat taaaaaatat | 180 |
| gcattgcaag aagcatatga caaacattct gagagtacaa aattagttgt aaaaaataac | 240 |
| ataatttacc agtaaaccca ctcatataga aatgtgcaaa gccttttgat ataaaaagtt | 300 |
| ttgtacacca agcacctatt tttataactt agcttcccat ggagagataa tggcttgcgt | 360 |
| gcattttatg tatccataac atacatacaa ggctcggtct tttcaatggg ataacagttc | 420 |
| acaactcttc gatttgaatt gtaatgaatc tggtgacaag gattttctc taatggattc | 480 |

```
caaagttagc cagaactttt aatgtcaaga tgaaaaaggg tgtaaggtgt tatattttct    540
tcaattcctt taccacagga ggctaactcc acaatttccc tcatgtttct cattcagaaa    600
aaaaaatatt aaatttgtgt tcagaattat ttgatgattg cttctttgtg ctgatgtttc    660
agttcctgaa gtcaacttgg ctctcacaat tttctaaggt caggttattg acttagggtt    720
gtataaacat ttttttctgg tttttggatt ttcactgaga acgaccttcc cttaatcgtc    780
ttctagatcc taattagaaa gaaggagaa tgtatagact gtaaatgtta ggaaatttta    840
aaatttaaga atatattatt ctctgtatat ctatcagagg ccattatttt ttgtaataaa    900
ccttagatta tgttttctta atatcttcaa cttatggtga agcaaatatt atattttgat    960
caaaagtata taaataata atttgaaatt taataatttt aactctttag aaaatttgtg   1020
tcaatttgga tatttacata gatttactga cacattcttt agttaaaaaa tatctgtgca   1080
gttgatcttt tactttcaaa ggtctgtata ttggattggt ttaaagtaag aagttcctat   1140
agcgcattga taagccttgt gtctcctttt cactactagt atctaattaa cccagaaatt   1200
ccaaacttgc aattccaaac ttgcaattta ctctagcttc cacaagggaa attcttgctc   1260
tctcaatgta ttggaatgta agataactta agtggaggaa ttagcaaatg cacatagtgt   1320
aattatgaaa taaattgtaa tgcacatgtg atatatacat ataatcta catatttaaa    1380 tgaacatttt gtaaatagct atattaatgg ttttttgcat atatacattt cttatttact   1440
tatgtctcaa actgtagcat tgtctcacat aataacattt taaggattc aggtccacct   1500 gcaatctaca tttgtttatc tctgatattc aacaatttct ttttgactta actcttatat   1560
acacaaaatt atatgtatac ttgtatatac aaaacattac atatatatat atatatatat   1620
atatatatat atatatatat atatatgt atggagaata tacacttgag tctatctcaa     1680
gggttcaata tgcctagcag tttacatgag tatgttgacc tttcccttaa tatttgttat   1740
tagattctga tagtatagaa catgagaaat ttattttctg attgttatca aaattgtttt   1800
catcaaaact ggctagcttt tctctctgat cgataacaag tttcaataaa atactttaaa   1860
atctttccta ttgtttgatt tctcttcatg taacaaaaga ggccatatac acacattact   1920
atagccaata cacttacctt gaactttttt gttggcttgc aacttcctca cgggtgtgtc   1980
taaaattaaa ttgttgtagt tagaaatact tcgcaattat ggctaaaatc agacaggaga   2040
ccatggttaa acagaacagt gtaaagtctt aaataagtat cacttaaaca cgaagattat   2100
ttttagtagt taaattttat gatcctcaga gttttacatt ttttcgtaaa ggacaagtag   2160
acagacagtg ttttccatat atcataatga atgtttctta gttgcaaaac acattgtttc   2220
attatggatt ttggaacccc acctaatgtg ccattttttgc agagtaaatg acttacatga   2280 tttttttcaat cttttttgtaa aaaacattgc cttatgatga agggttatta aatgtcatat   2340
aaagtttaac acaagtatct tcccagagtt agccacccat ttttgcagtc atacctatgt   2400
gcaatgtctg cctctgtaaa attatcacta agatcaattt gtgattcctt tattgtacat   2460
tgacgacaac aaagtagcac tgacctaatg attctagaaa tgttataata agtaattcag   2520
aaagaatatg ccatcaccct tgttccacct cccaacctga ttcagtgtca atcctatgag   2580
atccttttaa aaaattaact aataaaaagct tttatttta agaactgcaa gtgtttcaaa   2640
actatgctgt tttgtgttgt tatagttgta acatatttct caattttcct gttttttcttt   2700 tagtttattg acaagactac ctggtcggcc taaattcaca ttttcattca gttttttgggc   2760 atttgagatc aaagagtaag tatggtttct acagttactt cattttttcta cttatctttt   2820
```

```
taaatttttt ctccaaattt tgacttcttt tatatgtatc atctatactc agcatgaagt    2880
ccagtttttt ctattatata catgttttca attcgctgaa atcatataaa aagtaagcaa    2940
tgaaactgtc accatgaata gttttggcta tatgacacca agcaaatttt ttaaaaaga    3000 aataacattc aaaacaactt atatattctg tttctgtcta cttagcacat tttcacattt    3060
ctttcccccc agaatataag gcatataatc atttataaaa ccacattaat actagagtaa    3120
aatatagaac tatagaaaaa tctcactatg ttggataatg gggagaagtc tgtgtaaaac    3180
aaccaagtct gagttatgaa atattctcca acagatataa atagatgtaa atataaatat    3240
ttcttaactt caggtttatt tggtaacgaa ataatggctt ctaaaaaatt gtcaagaaga    3300
gacagatcca acctttaatt ggtgtgcagg cacattgctt atagtggact tattaaattc    3360
caaatagcag ttaattgtat aacttaaaac tgcatcatag aagtatttac caatttcttt    3420
tcaaaacaag tgtgctcact cagatttcct ttcataattt tgatagcatc caattaatga    3480
ggttttgctg tgataatatt ccagaataaa aaacattcaa tgtgtcaaac aaatactttg    3540
aaagaacagc ttgattaatg tgtagaaaac aggtttactc ctagcagctc tctgctatgt    3600
caacatgaat gagagttata ttagatcatg tttagagcag caaaacatgg gaagatataac    3660 caattacttg aatatattgg cacaaagaac caccctacat cttatttcct aaagcatgca    3720
aagtactcag ctcaattatt ttgacatttt atttgcatgt ttgttttttg tatgtttcca    3780
tggttatgac tatggaaatt taagttggg tgagaaacat tacttaattg accatgttaa    3840
tgtcaattga tgattgacag taacatttga tgacagctta ctttgtgctg aacattgttc    3900
taagagcttg tcatatatta acttatttag actgtaggta tcactactat cctcactttc    3960
agatgaagga aacaagcaag aaaagagtca actaatttgg gattgagttg gggctcagac    4020
tgaatgcaga cctacaactc gatctactat tctctataga ggttacaaat cttaacctct    4080
tatgttggca gatttgcgaa aaccttcaaa aatgactttt tgttgttgtt cctttcgaca    4140
tagtctgtta ttctccttta attgcttgag tcgtttcaga atgcataatt ctaaggtaag    4200
cccaaaaatt ttatgcattt aatgagaaat ttttcagtt aaggtcttgg aagtgtatca    4260
gtgacaaatc acaacatcag tactcaaagt accagttagc catgttaata gtcatgactt    4320
aaatgattga gaaatatact caaattacca aaagtacaaa aaatgtacta catggccggg    4380
cgcggtggct cacgcctgta atcccagcac tttgggaggc cgaggcgggc ggatcacgag    4440
gtcaggagat cgagaccatc ccggctaaaa cggtgaaacc ccgtctctac taaaaataca    4500
aaacattagc cgggcgtagt ggcgggcgcc tgtagtccca gctacttggg aggctgaggc    4560
aggagaatgg cgtgaacccg ggaggcggag cttgcagtga gccgagatcc gccactgca    4620 ctccagcctg ggcgacagag cgagactccg tctcaaaaaa aaaaaaaaaa aatgtactac    4680
atgtaccaca atgtatacga tatgaactgt ttagatagaa aattcagttt taggtagaac    4740
ttattgagtt gaagagcatg gttcagatat gtattaattg gccagacctt ggaaaaaaaa    4800
aaagtcttac atagtgtaat ctttactagc ttctttatc aatgcctttt aggatctaga    4860 caagggata cttgtgactc agtaatgacc tgatggtttt agatagctgg aaaaaagaaa    4920
acaagcatgt ccaattaatg ctggtactag taattctacc gcatatagtg ttttcctac    4980 aaaaagcaaa accttggaga aatgatttga taaaaacttt taattttttt tgttttttca    5040
caatgctata atagttgacg tggcattgtg aaaaccgatg ccttacagat atgtagagag    5100
atcatacact gggaactaaa ggaataaact tctgggatga tcagaggcaa gagctaagaa    5160
aggagttcat taactaaaaa ttgaatgtca tatacttaac ttgtagcagt tatatgtttt    5220
```

```
cttggctgaa gcaattcttt agtatttaac tggattttc atagtggcct caataacagg    5280
ggcttatcaa aggggaagaa aatatactta cctgaaattt aatcctaaat gaattaaagc    5340
aatataaact gatgcagcta ctaatttatt gattccctaa aaagcactac cattctacaa    5400
agctgcttac tatggcaagg actgaaagaa aaaaaaaaga attcaattta atcttcataa    5460
tgtgtttgtc tcttccctca aatccttaga tttttttcct agcagacagt tgagcattta    5520
ggggtagata gtgaattctt tgttagatcc tacaggaatc tttggttccg ttatggctct    5580
gttgtgctat gtactcttag aattctggga ggaaacttgt attttttcaga catatatatt    5640 tctattgagg gaaaattcaa tcattggttg aattaaaaat ttttaaacta tcactgacaa    5700
gtttctaaat actatttaag agattttacg tttattaaac tacagaatat agaaataata    5760
attgctaaaa atatagaaag tcccaagata atttacattt tcttggacat agtgatacag    5820
ttttaaaaag tataagctga aaagccatct ggactgtgtt ttggataaac atcaaacttc    5880
agttatgttt ctcaattaat agtatatttc aaagtgccta tttggttttt ctaaagaata    5940
taaatacatg tttcacaaaa ataattttt cagcttaatt ctttccttgt taaaaaatga    6000
agtagaaatt tgtttattca aatgccaatg atacaaatta tgtatctata taacaaacat    6060
ctttgaataa ttactatgta gggtttgtgt aagattttga attctttttt ttttgttctt    6120
aaggttcatt taatgccaca gacagagaac attccataaa agattaagat taattttata    6180
tgcaaaataa cttatatcta caggtataga ttatcactca aactgttaga agaaacagat    6240
attcattccc aagaatatag ttttggaaaa gaatgttact aaatgcacta ttttttggcta    6300 tatctatgta tagaatttaa agacatgcct tgattgctct tatgggggca gtgaatataa    6360 tttttttaaat ataaaagta tatcaaattt gggcttgttt aacagctagc aatttaacaa    6420
ttatttccct tttgcatact taaaaggccc ttaaaattat ctgaatcaaa gcaaaaaaa    6480 tattcattgc tccccaaact ttataccata gaacttttta aagactgttt aaactagtaa    6540
tcatttcttc ataactatta actaccattg aaccaatcca tctattaaga caacagtgga    6600
tgttgtcttt tttttttta acccaattaa aagaaaaaat ctgcttgctc agtctttaaa    6660
aagttgaact cagtcactag aacctgttaa gggggttagt tgttgtcctt ttactaacct    6720
ccctgaagca gtctttaat ttcttcatct tcaaataaat gaccatcacc accttcaatg    6780
aatttggtga ccttggtgac ctctgagagg atacatgttt atagcagaaa ttggtttata    6840
taacaaaata aagacagcag actttatgtc ataaataatg gcatctgccc aataatgaat    6900
tccagcccaa cactcgattc tttcacaaat tttagtgctg ttttctgaca tactaatatt    6960
cttataaagt tgttgaacaa aatactgtat aaaaaatatg actgccattt atgcttaatt    7020
ccttattctt gtgctttttt cttgttggta tggaaatgaa caatagattg agatagagta    7080 gaaacatgt agaatgttat tttagacttg tatatggata gcttaggtaa agtcacattc    7140
ttattttcct agaaatgctg accttcttgt aacaatttct tcagagtttc ttctgtttct    7200
ccacctccag tagaaatcct agtgtatttt atttcaggac ctatgagaag gacaatgaaa    7260
aaggtctaaa acagaagtag gcaaacttct tctgcgaagt gacagagagt aagtatttta    7320
cacttgtggg ccatgtagtc tgtgttgcca ttgttcaact ctgatacttc agtgtgaaag    7380
cagccttagg tattatataa atggatggga aagactgtgt tccgataaaa ctttatttcc    7440
ataaatgggt ggcacaagcc acacttgctc actaattgtt taaacaaata cttaaagaat    7500
agctgaatta aggattttcg gcgaatttta ggctaatttg gaccaactgg acgctagttt    7560
```

```
ggaagtctga tatgaggttt actgaaaata ttgatcaatt gctttgtata aacttgcttc    7620
tattttggca ggtagatgta cagaccttaa gattaatgga agctcaaatg aggaaatggc    7680
ttttcttcta gggtcctcta actcattaac aaacagtaaa gtgaaaatgg aatatcatat    7740
caatggtata tcatattaca tgtatgtatg catacatgta ataaaaacaa atgcttttag    7800
atttgtctac aaattttcaa ttcagagtaa aacatagatt acatatttag aataatatta    7860
tatctgccaa aatatgaagt aactttagta atcactatga aaatgacttg tttcttaat     7920 gattcttata tttggggatt aactataatt tgatctttat aatctaggca tagatccatg    7980
tatggaatta atggctacct gtaatgattc gttcttctcg tgtctctttt tcagttattt    8040
ccacaggcac tccatcaatg attttggtgt attttttaat aattggctct aaaagcaggg    8100
gaatacaaat gcatttgatt taccctcata ttgtgactat acatccataa gctagacatt    8160
gtaatgatta actatatttc tacaaatatt accatttaag attcaatcat aaacattttt    8220
agaacatatc ccccaaaaat catatcaata gggatctaaa aggtaatagc tatgtcctga    8280
atcttggttg agagagaggg ccatttgaca tcctaactct ccatgtcata cttgttttct    8340
ggatgtggaa taaatactta gtgagaatcc agggagttct atatcattgg aatgggagcc    8400
ctatcataaa tcctagtagt ggagtggctt attagacaga gacttataca atggtcattt    8460
tttcctactg tttctaatat ttcctttat actgacatta atgttacaat tttattccac    8520
aatcctcact tgtatatgca aaaatcatga cattttgttg ggcccagtga cttaatagat    8580
aaattaattc caactagatc cattaaaagc taactatgtt ttatttctga ccagctaata    8640
agaactcata gctgaggaaa taattcccac aattttttata aaataagaac taagagaaaa    8700
tatcagatgt tcaatatttc taaaccaaca ctatttcaaa ataatcacag cgaaggtagt    8760
cggccccagg taacataagg aacgcacctc catggatcac ttcagttatt gtttcacctt    8820
ctttaatcag tctgaattca ggttcacctt caattttgac ttttgttagt gtgggtcctg    8880
ggacattatt ttaggagaca aattatcatg ttaaaacagt cctttaaatt taccggaata    8940
ggacatttat ttcaacattc ggtgtgactc aactcaaatg tcaaagtggt ttcaggctct    9000
atgaaatcac ttttaaatat ttcccattgt cttcaaatta acaagagtt atgagaacaa     9060 atgatttagt ctgtttgtgt gctactaaaa ttactttcat ctgctttagc ttttaaacag    9120
atggataaat ccatctgttt attcgtagtt ataaagtatg attatgcaaa atattatatg    9180
tggctacact ttgcagatca tgcagtatgt acacatttgt gtttctctga taactggtgt    9240
agatcccact ttatcatact gatattgtct attactttt ccttattaaa atttttcatt     9300
taagttttaa aatcactcag taccttatat ttttgatcta gtgggtatag gagtgaacat    9360
aagaaagtac caaatgtata cctacccttta agatgctgaa tgtcaggttt tatgaggaaa    9420
ataatttgag tacttacctt ctgtatggga atgatacaca attaaccagt taatagttaa    9480
acagtccttc aaatgcaaaa gataaactag tgttgcattt gacttgcaaa atgatttgc     9540 taccacagaa aatcattttg aaggttagaa agctgcttac tacattagtt aattaagact    9600
gtttcacaga ggagtaagaa aaataagttc agtacattta actcatactg taatagcctt    9660
caatagtgga atgcaactgt tgcttgctta tctttgagag catttttttt tgcttgttca    9720
gaaattgtca atgtacatga ttccaaaac gaaaccagcc tagaacaatc caaaataatg      9780
aaaataaaag taagtttttt tgaaaccata agtatttcat gccataatat ttgatatata    9840
aggccaaggg atattgagca caaaacataa agccaggttt ttaaggtgcg gtaacttcaa    9900
aagaaaggac gcctaaggaa tttaagaacc aaaaatgcgt taataaaata tctaaatcaa    9960
```

```
tatttcttta gaaaagccaa actgaaattt tggaaacatc ctttatagtt aagctctata   10020
aaagaagaga ttttctcaaa attgttttcc tatttactcc caacacctca gaaagtaccc   10080
agcagaatag ctgctcaata actatttgtt gaattgaatt ttagctgatt tattcttaat   10140
tccaaaatgc tgttatgtat cttttataag agacacctta aaattgtgtc ctggagttta   10200
attcatttag taagaattta aaagtcatca ataaatctgt aattgttcaa atagtaagaa   10260
ggaaatgcca gtagcaatcc tggaagctgg accattgtaa attactacta agataaatat   10320
ttgtttcctt cattatgcta cacaggagtg taatttctga actcaagtta ttaatgagta   10380
ggtgacacaa ctccattttt catccatgtt ccctttataa gaagaagcca tgtagagatg   10440
acccgccagt atgatcttaa ctgaataaag attagtagga tagaatccta ctgacaaaga   10500
ttgaggagat aaataagttg aataaagaag cttcaaagga gaagaatctt tgaaaataag   10560
aacattggca catgtaaata atttcaggta aagaagctgt gcacaattat agtgcaaaat   10620
tttagggaat ctgattttta aaaacaggac aagatttgat tttaaaatca attgtattat   10680
caaagatcat tgtgtcatgt tttattacaa tgatcaagga acattttttc aacaaaactt   10740
tctgatttaa ttcttctta aaataccgaa ttgtcttcat cactatagaa agtcgattaa   10800
ataattataa ttatagtatt ttttcaaga aaaaacaag gatagatttc aaagaataac   10860
tcaattttaa gtctcaagaa taaatactaa tatagataac taattagcta ggaaataagt   10920
ttttacctat gtattttcag tgtataaatt taaattaatg acttacttta aaaaatatag   10980
ataaaagtat tcaagaagtt accttctcaa accaccaaaa gaaatagcaa aaccaaacat   11040
aagtataatt acagtttccc aaagattcca tcaaagatat aatctgttct cttttggaa    11100 gactgtttct agctttctta tagcacaaag gagataacta gttcttttct ctgggtaagt   11160
tgctacatta agatgcttat acatggaaat cttaaaaaat ttaaattgtg atccttggac   11220
ataattaaaa tacatgaaat gaagtaaca tcaaagatgt tgaagttggc taacatacat    11280
agtgggagta gagagaaaag taactgctta tttaatgttc tagtctgaaa catcaggaga   11340
gaatgtgtgt gtgtgtctgt attatatata tctcatgtat aatatatacg tctgtatgta   11400
ataatatgtt cagggctgga attaagtatt ttaaaaatca attcactgca taaactactc   11460
attttgtttt ataattctga tggtctaatt aaaaaaatatc tcatgcgtgg ttgtaatttt   11520
aaaagctttc agtaaacata gcttctatgc tatcttatgt tacacaatga aaaatgccta   11580
tacttttttt ttttggaaga gcttcttgca ctgttataag aaagaacatg tgggagattg   11640
caaacaaagc aacataaaga gtatacagcc tgtaggagtc tgactaaagt aaaaaaaact   11700
catgtctttg tttagtgagt atctgtatac taagttaatg caatgccaat tagattcaaa   11760
ttaaatcaag tacaagcaaa tgtactgaaa gtattaggaa tgcatcatct actttgctaa   11820
ataatttgca ctccgcattc tgcaattaca tgagcatgcc attggtataa tattggttat   11880
ataacattta acatgttagt ttttaaaaga atgtagatac attcatagag atcagtatttt  11940 ttacagatgt ttttactata aaaggaacca tgtataacat tgatttttac cttcagtttt   12000
gataataggc tgaagactgc cttcaatcac tttaattttt ggttccacaa ctttggttat   12060
aattttagtt gctgaaagta tagaaagtgg aacatgaaaa atatttacat aaaaacctga   12120
acaaaggttt tttttttttt tccttttctt ttttgtctct gtaggatact aaggcacagg   12180
atgtggtaat atgttcaggc agtcagatac aggaaatatt tatggtacat aatataaatat  12240 cttctcatgt ccaggtgttg aactctgaag tctagtgact tgaatttgat ctagtgaaat   12300
```

```
atatactcac aaagtgagga attatatcta gaaatctgta atttttaatt gtaccgctaa    12360
agcgctttac cttcttttgt acttcttgaa aatactggct gcattgcaac agaagacaaa    12420
tatgattaat gtcatgcaat tcataatatc ttaaattgca ttgctggatt ctttctcaat    12480
taaaagaaaa aatgaaagaa aaaggctttt aaaatgtttt tcatgcatct gataacagtg    12540
acatagaaag gaaaaaatga aacatagttc agaatactta aaagtaagaa taaatttcag    12600
ccagccagac atgagctcta ttcaacaaac atgatatgat cagtatttaa gttataggct    12660
aaaatgtctt taattttcag ctttgttatc actatccttt ttttttttta atttaaaggt    12720
atatatttta aacgtgtgtc gtctacctaa gtaagataat agtctttgaa ctaggtacta    12780
tgtttgctgt ttgggtgatg ggttcactag aagcctaaac cccagcatta ctcaatatat    12840
ccatctatca aacctacgtg tgtacccccc tagatctata ataaaagtaa attaaaataa    12900
attaaatacc agtcaactat ttggttgact ttggttgtac tgattaactg gaaatgtgcc    12960
tctgaagcca cacagccaga gcaactggct ttttgtcatt tctaatgaaa agccttgaaa    13020
gatggttcta ttagataacg ggccacactg aagctaactg tgcatctaga tcacatcaaa    13080
gcagtagagg tgagatgtta gcacagcttt ggtttctgca gttctcacct catgcttgta    13140
agatgtttag ctgtgtcaac ttttttgaatt aatgtgggtt cttagccttc atagaccctg    13200
tgtttcagcc ttattaggtt ttgtatttttg agatctcaaa ttgtgaagct ctaaaataaa    13260
acaaatctgt gtgtttaggt actagttcca caggtggtct tgccacagaa gaaccttttcc   13320 atgaaagtcg aatacgaata cacagggctc tctattgctg ctatcaaaat ggactaattc    13380
cttttagctt acattttttta catcatgtta aggaatttga cgttttggat gttcagctgg    13440
ttggtagttt tcatttcaat cttgattttc tgcagactta aatagttttg acaggtgaag    13500
ctctgaggat taaatattga ttttagcccct ctccaggtca aatgttccat atttgacaac   13560
ttataccaaa aacagcatcc ttccctcaa ctatacactt taaaatggat gttatttttgg    13620 ggatgaggat aatatgcagc aaaaaattat aggaatttta gaaacaagtc aacaacgaaa    13680
tataaaaata gaaaatttgg tttaatttat ctttacttct actttaaaat acttcttaat    13740
aacagcatac cgtctaagga ggagtaaaag aaacatctta cattggaatg taaatgttag    13800
agctgtttca aggcctctgg gtaggtaggg aaggaccatt gaacatgtgt gtcttaataa    13860
aatgtagctt atgctctgtg agtgaggatg taatttagta ggagaaaata attatatttt    13920
tgctcattgt aatcaagata ttgcattcac atatatagaa agtagtgaaa ctaagatgga    13980
taaagaaggg aagctaaaga aatgtagtgg gaatgtgtat atatatatat gcatatgtat    14040
atatttatac ctttgatgaa gaaagatgac ataacatgtc tgatgaatag agcccataag    14100
gattgcttaa ttttcagaaa acatattttt tacaagattg tattcccatg gtgaatcata    14160
actattccaa ttaaatcttt aatacagtgc tgagctggcc tgatcctgga attgcatgtt    14220
attattgcat aattgaaatc aacaacagca gcagacattt tgttttgctc cttacattgg    14280
ctttactcct tttccatatc tagtataaat cttaagggaa atttttcttaa ttaaataact    14340 ggatgctcat ggtataaaat ggaatgattt tctagccaga ataaatgtgg gtattgaagt    14400
aatgttttag ctactgatac actttgagtg tttaattaca gagccaaaac aaaatgaaaa    14460
gaatttctgc ttgaaagcta cagtgaaata aagaaagaga gaaagataa acagagaaaa     14520 agccatgatg gaaagatat actactagct acacttatga gaatgaaata ccctttatca    14580
ttgttaagta gtagaggttt aattttgata atctggttgt gtcagagatc aaagaaccct    14640
ggaatttgga aactttaaat ttgtcacatg gcagattttt ttgttccttt gtccaatttt    14700
```

```
ggatgggaga gttttrgaac tgccacctta taaacattgg tattcttcaa cacgtgcttc    14760
tcagcctgcc cttagatagc tcagggcttg agggtggcgt gaacaacaag tcttggctaa    14820
ggtcatttct gtgtccacac atctgaattt ttagatattt ctagagggtc ttttcgccat    14880
ctcttccctt tatatgtctt tttattttcc tggctctttg ccacgctaat attatatttt    14940
gctgtctttc tcatgtcata tcatttctgt ttttccaatg agtggggaag aagttcattg    15000
gagttgaagg ttatctgaga cctcaatcct tttttcaagt gaaatgagat tggccatagt    15060
ttggaattct aaataccaga ttatcaataa tctctgtaaa tacaaagaaa tgtattgttt    15120
tcttttttca taccttgcca cccaggtggc caatatttat tatatactta ctatagacag    15180
tcacggggat ttctttgaag gtgctaccac gaacaaactg aaaataaatg tttatattta    15240
gtaacatgaa aggtgatagt tgtgttaaca aaaccatggc accactttaa ttcttattaa    15300
agtaaaaata gtgaagctat tattacactt aatagaagtg aagtcctcat ataaatcatc    15360
ttccaattca atgctatcag gtcagagggc ataaaaatca ttggattcat tactcagaga    15420
tttaaaaatt atataataat taatccaaag ttaaatatat ttatgaaaca caattttatg    15480
tttcctgcta cttttacccc tacattgaaaa agaagaaaaa tattccgttc cctttaatct    15540
gtgatgagtg acaattttt ataagtgaat gttctttcct ttatattctg cagtgaaagt    15600
attgaatgat acaacgattt tagtcattta tgtaccattt tattttcta aattggactg    15660 taaacttttt gaataaagac atgtccaatt taaatacata ttttcataa cactttacac    15720 aatacttggt cctgagtagc ttttaataga tatttgttga acaaaaccat gaagaaatga    15780
tgccatttct ttacaggtgg gtcagtggta cataaacaac aaagagtaat ccaagcccag    15840
tacatactta cttattaatg cgtacatttc tagcctgtta tgttaaacct gtaatatatg    15900
ttctacatat tagaaataaa tcaagtaact tttaggctag gcgcggtggc tcacgcctgt    15960
aatcctggca ctttaggagg ctgaggcggg tggatcacga ggtcaggaga tcgagaccat    16020
cctggcgaac acagtgaaac cccatctctc ctaaaaatac aaaaaaaatt agctgggtgt    16080
ggtggtgggc gcctgtagtc ccagctactc gggaggctga ggcaggagaa tggagtgaac    16140
atgggaggcg gagcttgcag tgagctgaga tcatgccact gcactacagc ctgggcgaca    16200
aagcgagact ccatctcaaa aaaaaaaaaa aaaaagaaa taaatcaagt aacttttagt    16260
accttaattt ggatgtattt gattaattta ttaagtattt ccagcagttg atcatttcca    16320
acaggtgtgt ctatgaagag aaatattaaa tgaatattgg taagaaagca taaaataaaa    16380
atcgaggttc atattaaaaa aagacttagc ctatcaatga gttcaataat tacaaacctg    16440
ctggatagag gagtttatct acaacatgaa ttacaccatt tgttgtcatg atgtcagatt    16500
cttttgattt caattcattc accagaagtg tatcatttac ctatcaaaat aggaggcaat    16560
ttcaatgagg aaatttcatt aaggatgaat atttagataa cttaatgatg gatgaacact    16620
atcataaatt cattctagac aacttacttc tttcagaaag attttgcttc cttgtgtggt    16680
ctttaaaatg ttagtaacac caggttcaaa tccttttcca atgaaaactc ctggtgtcag    16740
gtgataaaga atgatgtttt gaagagcatt tttgtcccct aggggaaat atatgtttat    16800 ttttattgaa taatatgact ttttgataag gactaagaaa caaaacactt attagtcttt    16860 atcttttttcc atattgtact ttctcataat atcattattc tctcaagtag atatcgatgc    16920
tatttcaaaa catagttatt tcaattagcc taatcaaaat agaacccaac ttactgggag    16980
aaaaaaatct atttattttc taaattataa ctgttttctt ctttgtcccc tgattacatg    17040
```

```
gtctttaata gaaaccacat aagtgaacat ctagcccaac aacataacag ttcacagttt    17100
aagaacatta ctgagtgacc ctccacacat cccaagtgga cgaaataaaa ggaaactaaa    17160
gctaaccatg aataccagag aggggggcatt tttaaggcag acatctggac aggaaagctt    17220
gagaaagaag tgagatcctg aaatgaaagg gaaaatatct ggaattcact tccacttacg    17280
tatcagaatt tctttttctt cactagtcat tcccttaaaa gcatcattgg ttggcacaaa    17340
taatgtccag tctccaggtt gtgtcaggag ctcttcaag tctgcagctt caagtaggct    17400
gaggaaggtg ctaagtggga agaatgtata tgtattttgt cagatttaga tttaggtatg    17460
ttcacctaca gtgcatgtaa tagaataaga tccatgtatt gtggaaagca tgagagaact    17520
gctcatacat tttcatatgt ttcgaataca atttacctgt taaaagtttt atcatgaaaa    17580
atgactgaaa tatacaatac aattttaat ttttttcatc tgatttcatc ctataaaact    17640
tgacaaggtc acacataaca aaaagaagc attttatca tgtaatactc tacaagatag    17700
tctttgctat atataccatc aatttctaaa aactataaga aaaatgtcaa gaagtagttt    17760
agtctgttag atttgtttc acacatgaaa tcatataacg gtgtaccaga aagtagcagc    17820
gaaaacatat atcaattttg aaaacacttg tatgaacatt ttattctaaa ttccatttc    17880 aaccacatag gagactgaat gccttttggg ataccgccta tgaaacaaaa atatgccaat    17940
agctctcatt ctctgtggag gtgccactaa taggcttacc taaagcgctt atcttgtttt    18000
aacttttcat ggagggattt ctctgctggc ttgatgatct cgcggaatat gtgaatcgca    18060
ccgtttctcc cttgcttact ccctttctcc atgcatgaat tttcaatgca gacagcctag    18120
gaaaggaaag aaaggtatgg ggtgtcattt tccttgcttg aaatttcccg tatagatgta    18180
actacataat taagtttccg gatcggccct tctgagaggt tgcctggtgt ctgaggccac    18240
gggaacagct tcttcctct gttttcaatg gctcacacaa actcacaaga cacttcttat    18300
ctagccgggt ttttattaa aagtcaagct accttatgga tcaggcaggt aattttgtca    18360
ataaattaca aaagttccat ggaatcccac ttctacattt tttataattt ctattcagat    18420
ttgaactatt tctctagacc ctcttttggc caacactatc tgtaaggttt cctcacttta    18480
gtgcttttag tgatcttcac aaatatttac tttattttct tgactgtaag accctattca    18540
tcattgtaag tcaaatcatt gacatattca tagcttttg aacgaacgtg atatatatat    18600
acacacatat atttgtatat acaaaattta agtgcagca catttaatgc atacttaaaa    18660
atgtttggaa ttttgtagct gcagggagct gctgacatgt gccagattca gttctaggta    18720
atgcctgact tcctgtgaag tcttttagtt gtagctgtac gtgttatctg acaaatact    18780 gaacgtatca ttagttgaac tgtaattttg ataagcaata tttctataaa ttttcctgca    18840
gcaaaatgta tgttagggct gggtgcagcg gctcatgcct gtaatcccag cacattggga    18900
ggccaaagta ggaggttcac tggaggctga agtttgaga ccagcctggg aaatgtagca    18960
agaccctgtc tcaagaaaaa ttaaattaaa aaattaacta gggtgatgtt gtgcaccact    19020
agtcctagct actcagaaga ccgaggtggg agggtcccct ggagccaagg agtttaaggt    19080
tacagtgagc tatgattgtg ccactgcact ccagcctggg tgacagagtg aaattctgtc    19140
ccttaaaaaa aaaagtaca ttaaaaccct ttttagagt ccagaaatct ctatgtgcca    19200
ataaaggttt atcttgaaag ccattcaaaa gatattcaga tgctgactgg ttattttaca    19260
gtataagatc accttgcata tttgattcat tataatgaaa tgttttgaaa tgaaaaacat    19320
tttagtagag acagcatagt gctaacacat tgtatgtgta gtcaatgcag aaactaatca    19380
acaccttgta aaacatttat tatttcttat tgcaaacaat catcataaag aaaaatggtg    19440
```

```
tgtaggcaga gaacagaatt accttgaaaa ttgtaaagta ctctgcaaag gaaaagttta   19500
ttttaaaaaa tttactgctt tctggaattt aaaataattg atgctctaga atagaaagtt   19560
attcataatg aaacacatgc aaaatatcta tctgagtttt gaatacatag cacttgttgt   19620
ggactttgct cacagtcttt tcacccaagc tacccagttc cctgatgctt ctatgaatat   19680
ttactattag aaccacactc ataaaattct gtgaaatatt cattgaaaca gcattatttg   19740
acatgtcatt tgacagactt tttattttgt tgtgattcac ttactgtacg atatacgaag   19800
actctgagct gtttgcctcc gatggtttcc agtatttgcc cgttgtaaag ctcattaagg   19860
ccaactttta ctttcaatat gtgattctgc agaattaatt taaggaggcg ctgatccatg   19920
ctgagagtat catctgtaaa taaattcatt aagaaagagc attattttat ttagaaaaca   19980
ttgaagtttc tcccggtaag acagaatcat ataaacagat aatccctgac attattgata   20040
tcatggattt tgcactcata taatacatga atcaaccaaa tgctaaaaac taacaattca   20100
attcaccaag tagaaactct gtgacctatt gtattaaatg acaataatac agttccaacc   20160
agttcaatca atgagtttca cctctgtaag ggctacatag ttttatagtg gtcactggca   20220
aatgctaaac cttaatggtg gccaaggctt tgtctgataa ttagatatct gttagtcaca   20280
tgaaagaact actgatgaat cctttgtaaa ttaatcttga ttactggaaa gagaatcaaa   20340
gcaaacaacc tcttaaatat gggttattgt caaaacacat gggcaggatt attacaaaga   20400
agaaagtcag gatatctagg aattcaattt ttttgattaa tagttttttat atcacaattt   20460 agcatttgga aaaacaaaaa attgtgttac ctatttttaa ttaataaatg ttgcctaaca   20520
atttaaatat gtctgtgaaa tcattttcct gagaaaggtc gaaggttgca tgaatctgaa   20580
catggtctgt gaatagcaac tactaggtga aatatttata tatactattt tacatcatga   20640
tatggaagtg tataagtctc ttcattttat ttatttataa tttgacaccc ttactgtcca   20700
aattttgaga tgcaaaacac acctatttat ttctaaatat tattatgttg gtatcaaata   20760
aagaaatcag ttttatttttt ttagagatct gtcaatgcat ccttattgtg ctggaaatat   20820
tagattcaca gagaaactaa atatgctttt ttttaagttt cgtttttttt tttttttga   20880 gacggagtct cactctgtcg cccaggctag agtgcagtgg tgccatctgc ttcctgggtt   20940
cagttcaatt ctcctgcctc agcctcccga gtagctggga ttacaggagt gcaccaccac   21000
acctggctaa ttttttgtatt tttagtagag atgggttctc accatgctgg ccaggctggt   21060
ctcaaactcc tgatctcaag tgatctgcct gtcttggcct cccgaagtgc tgggattaca   21120
ggtgtgagcc accgcctg gcctgaatag tcttaattac aaattacaaa tttcactctc   21180
tgtaggctat tatccattat aatgaaatgt ttagaaatga agaacatttt agtagagacc   21240
atgtagtgtt aacacattgt atgtgtagcc aatgcagaaa ctaatcaaca cctcctaaaa   21300
catttattgt ttcttattgc aaacaatcat cataaagaaa aaaggtgtg taggcagaga   21360 gcaggaacaa cagtgtccag cacataccag aaaatgcatt attcacaggt gccagcaaag   21420
tgtattctcc atctggcctc agagcagatg ccaagcctaa ttgggccaca agatccgtga   21480
aggtggtttg ctgttttcca gccagctcaa taacttgttt ggctgaaaaa taaaccatca   21540
ccatcacaac aatgtcatca ttgctattat ctccatcatg aaactagtaa atcaattcct   21600
gactcttttc taatattgta agctatttac tgcaatgtca gtgtgataag acatcctcct   21660
cctccctaat aagagagttc cacttccatt ttttggtggg agttgataat cacgataaat   21720
ttcagaagga aaatatttttt ctgtcttcct actacatgtt tctttaattc tctattgttc   21780
```

```
atctctcatc tttctctcta tactgtgagt tccatagctt ttccatttat ccaaagctga   21840
ccatttggtt agatctttcc ttctctttcc aagaaaaact ctggcactgt gaaaacggtt   21900
ataaatatta gatgtcagaa accctagaaa gccaaagatt catgcatgga gttcccatca   21960
ctacactgcc tatctatgga gtgctcaagt agctcactat ttattgtgtt agtgctttgc   22020
atgccattct ttatactgca cattcatttt tcatggactt actctttgag acagcataat   22080
tagtaaatta cagtaagtaa aaaacaaaa acaaaaacaa aaaagttgc ttaccagaat    22140 caggaattag gacctgatca atcaaatgga tcacaccatt atttgtcaca atatcctttt   22200
tgttcaccat tttgattcca tttactgtta tactgtcacc gtcacatcct atctcaattg   22260
tatttccttc cagcgtctca aagactgctc ctcccataat agactcagaa cactggagag   22320
tatttaagat gtggtacttc ataagagctg gagaacacaa taaaaacagg tagctttcag   22380
atcaagggaa ataacatttg accctgaaaa gatgtgtttc actgtggaac taagtattcc   22440
ttaaaatgta gtaaaaccta aggattcact aacagcttta aaatcctatt tatgttctaa   22500
aagttttttc ctatcaacta taaaatagaa acagctcagc ttcgtaggaa taataagagg   22560
agatcagctt caggaaatga ttggtgcagt attagaaaac gtggtaggtt aagttccagc   22620
tatcataaaa aagtaactcc tgatgtgaaa gcaagaattg ttcctttcag aggaactttg   22680
actggcacaa gggctcacac ctgtaatccc aacactttgg gaggcctagg tgagaggatt   22740
gtttgaggcc gggagttcaa gaccatgatg agaaacacag caagatccct ctctaccaaa   22800
agagaaagaa aaggaaggcc tgtgaaattc caaaatacc aagagcagta tcttgtaata   22860
gctgctcata gcagaatatt tgtatataac atgtaatgag gtcgatagag gctgaggata   22920
agacaaatta tttccggaag gcaacttcta gaaagtaacc aaataaagat gattcattga   22980
aggacctctg gagggatcta tgcctcaact acattatatc tatcctgcat cctaaaattt   23040
tctcatctta aattggttaa atgtattttg ggataggctg agtaagtgaa gtatgcaagc   23100
acaatgtaaa acctatctga caacagcaaa gaagcttgga aagccaccaa attcttatgt   23160
gtatcagtaa ttagaggccc aagagaacca tacagttctc acaactcaat atcttttggc   23220
ataaatacag aattaaaagc attgcataac gtgcatacaa tattaaaatt tgatgatcta   23280
atatttcttt ccaacacctg ctaatccttc tgaatatcta ctacttattt acttgaaagc   23340
agtatgaaag aatgtgatct tgagagtatt cttattattt aagaattata ctctgcctac   23400 tctttaagg acttttggaa gacatagtac atctcagaat aaaaattttt ccctgccttt    23460
gcttattaaa actaatatta ttggtaagga ctagcctctt tttattccc ttctcagaat    23520 gctgggagac tccttagaga tgaagacatt aaactacctt cggaagccac tttgtctccc   23580
atgatccttt ctaggacacc tcgtggaagt ttctcaaaag cctcattggt gggagcaaag   23640
agtgtgaagt gaccgtctct tccaagggcc tccaatatgt ccgatgtgat ggcagctgcc   23700
tgaaacacaa atgtgctttt cagagacttt cacattgtaa atccagaaaa agattgcaac   23760
acacttagcc taggctgaca tgaaggagct gattcctaca ctatagaggt ttgttgttgt   23820
taaatcttca aaatattact ttttgacaca accatgtctt ttccaacttt cttcaaattg   23880
tgtttgcaag aatgggaatt ctgcccatgt ttatgggact gtagcaatat ccagcagtac   23940
atataataac agatgaacac gttctaaatg agctaaatac acgccagtca tgtgactaac   24000
cattcttact ctatcatgtc cacagaaata ttattatttc atatgagatg gtttcttctg   24060
tgtaaaatga aaatagtagt cctttcaaaa aatatgtgtt acatttttgc cagatttaat   24120
agcattttta ttgttttag attttgacag gagaagaaga gggatttcaa tgactcaaga   24180
```

```
caatctgctc ttggacttac tctaaaagat gaaaggtcat cttctgcttc aatgaagtct   24240
tgaattgagg taccaatttg tgtaagcaca cggtcaatga catggacaac accatttgtt   24300
gcaatctggt tcccatggat gattcgagca caattaacag tgacaaccta taattatttg   24360
gaaaaatcaa agtgctgaaa ccagagatac ccattgacca ctgagactgc aagcccattc   24420 ccagttttc atttatacta gtaaatgtaa catacaggaa actacattgt aaatgtaaac   24480
gctgtggatg aagatttaca tgttgttata tctaaaaaag aaactgtaag agaaaaggga   24540
accagttgag aacccaagtc aagtcatact aacatatct agcaacataa ggcaaaggtg   24600 ttttttcat ttaaattatt gcttttctct tttatgcaaa tagtcataaa cttttaatg   24660 tgggtcaatg aattaggtaa agaagtctaa tcagtcctaa aatttaagtt ttgagaggga   24720
gaaacaaata attattgtat agatataatt agttacatta caagaacttc ctaaaaattg   24780
tttcttcatt gacctctttc gtccctgaga atttggctgg ctgtggaaaa agtcctatga   24840
ccctgttggc agtttcccac aaaatctgat ccaaacacac aagtacttca gttagtacag   24900
tagctagagg gggagtaaaa gaacactcat tctttgatta ttcttttgc tactacgata   24960 aattatttca aacatatcaa ctactaaaat ttccttttct agaatacctg tctactgtca   25020
atgaactgtt catgtaattt gtcctttaca atcactcttt agtagaaatt aataaccaga   25080
ttggaaattt acatgcccta gatttggggg taaagtcata atatagcact taccttattc   25140
tcactaacat tttattattt tgtgagcat tatataaaaa gtatagacaa aattaaagaa   25200 ggtattttc ataagtgtac tttttactga taaaacttac cccattagga taatggttaa   25260
tgaaaagccc caaattgtta tacattgaag gaataatcat gccattttt aagtccttgg   25320 tcaacattct cttattaatc atgtgactat gtaaagcatt cagtaattca acattcacgt   25380
tgctctccaa acctctacgg atatcctagg aaaaattgca atgatagaaa ttcaatttat   25440
tgtggaacat tagtaaaagt cttacgatca ccctatttct actctcttgc tattttctca   25500
tttcattatc agatggtcat acaaaattga cataaataac ttaaaattat attattctaa   25560
ttggttaagg gattttgtaa gttcagatac ttacttaagg atcctgaatg tgatacagta   25620
cttagaacac aattttaaa gtgaatatgt tgatgaagag acaatcttga tataaataat   25680
aaaatgataa gaaagggaga tatgaaatta tcacatattt aaaatacttt aaatggcaaa   25740 caaagaaaa caaaaatgac attatatttg tatgcaacac ttaagtttta acagggttt   25800 catgtttatt ccataacaaa ttcaagaatt caactgtcct gtaccttttt atctatccaa   25860
cactatgtgt catattatgc tttactcaat gctatgggaa atataatgat aagtaaagca   25920 aaagtcaca actgtttatc atatagcagc aggtaaaagt agacagagta agatataggga   25980 cagagggaa aaatgctttc agggctccaa taagaaagaa cagctattcg gaagtagttt   26040
ggagatagac catgagattt aaatgaatag gaatggtgtg gtggtctttt aaatccagtg   26100
ctgagatagg gtgaatgcca agagagcaaa agttgtccag tttggttaat acacactttt   26160
atgtttctca gataatacta agaaatttag aagggtatgt gggacaataa cgtggataac   26220
tttaatgccc taagaggagt gaaataaact ggccataagg aaccactgaa gattttgtgg   26280
cattggaatt taatgattag aaccaggctt caggaaggtt gagtggtaat gtacagcaga   26340
aattagagta ttaggggat cactttagat gaaacatgag atgaggctaa cagcagtttt   26400
taagaattgg agaaggggaa ggtaaggatg gcttacaaat ttcaagtctg aacattgaca   26460
ctggtactgc caattgtggg gaaaagacaa caaaaaaac caattatta ttgggggaa    26520
```

```
agaaaattgc atatgtttta gataactttt gtttaaagat gcagatggta tatccaagga   26580
taaatgctaa gataaacaat agaaatattc tactgaggtt ccaagaagaa acaagtccaa   26640
acaacaagcg taggtttact gtttgtatgc actaaagtga tagttgaaac catgataagt   26700
gcatttaaag agcagagtca agtgctggaa gaaattctta taagttccat tcttttatt    26760 tttatttta cttttatta ttatactttta agttttaggg tacatgtgca caacgtgaag    26820
gtttgttaca tatgtataca tgtgccatgt tggtgtgctg cacccattaa ctcgtcattt   26880
agcattaggt atatctccta atgctatccc tccccctcc tcccacccca caacagtccc    26940
tggtgtgtga tattcccctt gctgtgtcca tgtgttctca ttgctcaatt ctttaaggca   27000
aggaagaaga tgagtcagca aaaggaactg gagaggtggt tagagatgcg gtgaaagaca   27060
accagaggag cgatttctat aatcaagcaa ttaaccacac agctagtgta gcaagataat   27120
gcctacagat atatacctac attttattat gtatatttca ctctagtaat aattatcaat   27180
tcatctccat atctagtaga aagtaggaat gtatttttat atcagtttta tagattcgga   27240
aattgagtaa taatttaagg cattgtaaat tagactgtgc acaaaagtct gaaaatcaaa   27300
tgtattttca catttcattt aactatccac atacatgtat acaaatttga caacctgaac   27360
atccatatat atacatataa ttaaacatac gtaataaaat attgctgtat aatactgctt   27420
atgataattt taaatttcag taggcttctt aacttacctt tctgttagac atgttatctg   27480
aaattacata catatcctca caaacaaaca ggaaagagga aaggagtaaa atagaatagt   27540 aagtgcccctt ttagctgatt cttgattccc cttcttaaaa aaattaaagt ataagtctcc   27600
tggagattta ttctatttac ggatgtatta agatatttta cttcccttaa taactcatcc   27660
ctttaggtat tctcatatat gtacaataga aagatataaa atttctacta atatccaagt   27720
taataagtca gttaaaatga aataacaata acagcaaaaa ataaatatat tgataaaaat   27780
aatgaattac agaatccaag ttgtcccaag cctcattact cggtgcaaag taagtgaagg   27840
atccctttcc ctcgatctcc tccctcagtt ttgaggcgtc agaatagcgc tgcgttgtgg   27900
tggctcccac gatgcccaga gtgccataaa catggtcaat gggcaaaact gaaataatca   27960
agaaatgaat cagtactggg gataatattc tcaggatatt attcataatc atttaaactt   28020
tatgctgtgt ttcccaagac atttagctaa taattttagc aatacaatta tatgaataat   28080
catttttata taaagttat cttttgagtg ctaaataata aaatgctact gaaaacatt    28140 attttacata tcctttgtgt tgaggaaaaa aaaatttaaa ctgtcatcct ggtttaacat   28200
ttaacctatt tagatctcaa tcctgctatg tcaataataa ttcaattata attcaatatt   28260
atctgttatt taaatctatc attttttatag atttgggtcc ctaaaaatat gtaggcctgc   28320 ttgtttttcat tacaatttct gggagcaaat gatttaaaat attcaatcct tccagattat   28380
ttctcccgaa cgtcagaaga aagattcatg aatgaatgtc agcctgaagg gatttatctg   28440
gtaatgtgca gtcaacttat ttttctgac cctatttatt tgaaaattag tataatttga    28500
ttaatagcat agaatcaatg gttattaaat ttgtgaatat ccttagattt ggtgacacaa   28560
ctattaagta taaaccagg attttaaag accctaaaaa gatggagaaa ttgagtcaaa     28620
atgaacaagg ttaaatttaa caaggttcca tgtaattcct atgcctaaat tgagaaaaac   28680
aaatcctaga gacctgactt aatagtgtat gtaaaaaaaa ctgtaatcaa ttttaattga   28740 ttctaaaattc aatataagct aatgatgtaa catggttacc aatgacatta tccaaagtgc   28800
aaggtgtccc caaatcaggt acttatcttg gtattgtctt aaatgctcag acccacatgg   28860
atggacttta aatatcagtc taggtttgta ttcagaagaa agattactgg actagagact   28920
```

```
ttctgtgggt tggtgttata atggggaggg cttcaaagtc tgtgtcatat taaaagaatt   28980
ggggatggtt agccagagaa tagaagactt tattcaagaa gagaaggtag ctggaggaaa   29040
ggtgtggtga ttggcatgaa atatctgaat ggctgccatt tcaaagagga aatagatgag   29100 ctatttttt tttctctagt tggcagaagt agaggaaacc aaatttcaat ataaagaata    29160
ttataaaatc agagctgttc aactagagaa gatgaagttt tgccaagtag ttgagttcca   29220
tgttcctaga caagttcaaa gaacaggatt ttgtaaagag ttttgttcct gaagggaagc   29280
tgaactaatt taaatttgtg actaagtttc tgttgtattg cccagcatcc agtgcatgag   29340
aaatatgctc ttatatttta tcattcataa attcatgatt aacacaaaaa taggagggat   29400
atatcttgga tttaggatgg tgctgaatac acacatacac aattggcttc tccacaagcc   29460
acctcaaccc tttctttgca tataattcct tatttaattc aaaaaattga gattttacct   29520
gctgggcagc ctttcattcc ttccattctc atataaccag gcaacattc atataacaca    29580 gtcctgtaca taggaagaaa attaatatta aaatgagaaa ctaaatagga tacatttta    29640 cataaatttg acaaaatatt tcacttattg acttgatttg ttgaggttct aaaaatcagg   29700 tttttttcc cccctgattt tttctttttt cttttgagac ggagtctcgc tctgtcgccc    29760
aggctggagt gcagtggcgc gatctgggtt cactgcaagc tccgcctctc gggttcacgc   29820
cattctcctg cctcaacctc ccgagtagct gggactacag gcgcctacca ccacgcctgg   29880
ctaatttttt gtattttag tagagatggg gtttcgccgt gctagccagg atggtctcaa    29940
tttcctgacc tcatgatccg cccacctggg cctcccaaag tgttgggatt acaggcatga   30000
gccactgcgc ccggccgatt ttttctatat ttctatgagt ttgatttctc actacagtct   30060
catgttacta tagaaaagtt ccataatgtt gatccagaag aacgacattt gggtcctagt   30120
tctactactt ggttgacatg tgaaccttga gcaagtcatt taatcaatag gagtccctgt   30180
ttccccaagc atttaacatg aatatagtag ctataatatc tactcacaga gtaattgtga   30240
atctcaaatg aaataatgct tttgaaatca ttttgtaaac taaaaatggc tagaaatctg   30300 cttaatata attggaaaca taagaaaata cattgaccca ttggagtccg taacatgcta    30360
tctcattgct agataaaata atgccatatt tggtttgaat tgttggtagg attattaatt   30420
gtattatatt atatataaac tttaaaatct ttttatttt gtaaaatttg ataaaaataa    30480
tctaagtaag tttattttaa tattagagtt tagtattcaa gaaagtggca tcctgtttaa   30540
agttaacgaa gtgtgttaag ttctataggc aataattaag gtaacagacc agaaaattca   30600
agatatcacg atatacaaaa aataagttta tctaatttac tatattttga gggaaaataa   30660
taatttaaaa ttatatataa ttgcttacaa aataaaaact gattatatta atgtataatt   30720
atattattaa tattataata taatcctaat ttttatttt tcgcatttca tagaaatttt    30780
tctggacttc atcatctaac ataggtagcc tatttaact caaattttac atagttactt    30840
atgtttcctt tcaaagaaa tataaaggta catgtaccaa acaattagaa ataggggat     30900 tattacaagt aaaaaataaa tgcacatcgt tttgtaattt ttaattgata aatatcatgt   30960
caaacagatt atgacaatta tagattaatt attttgcaat tcactaatta acatgaatc    31020 agcttattca aatgctattt cttttctggc ttttatcca gttgtcttaa ttgtattcaa    31080
gaagtatgaa tgaataaaat aatttagaca tgaaagagat cgccaagtat aagaataaaa   31140
tcttttttta gtatgataaa aatgataaaa gcaaactatc aagaagcaaa aattttaatg   31200
atataaaaga tgatttttata gagttgaata aaagtaaata aatgttttca aattgaaccc   31260
```

-continued

| | |
|---|---|
| tgctacacta agtaattatc taggatttgt agtctggttt ataaccttgg atcctcattc | 31320 |
| tttatttgtt aataaaaaat tcctggcatg aaatattggc ttaagaataa tagatagcta | 31380 |
| aaaatacaga caaaattaaa tgggaaatac ccacttcaag ttattctcta attttaatat | 31440 |
| agtttgaaga atagttggta ttggaaacat ataaaaggta tataggagcc ttatgcaaat | 31500 |
| cataatagag cctctaaata attttattta catgagctct tgtaaataaa tctaattatt | 31560 |
| ggatgtcaaa agattgatta acaattgctt atatattagc tttagcatat gttgtaaaca | 31620 |
| atttaaaaaa tgagatacaa atgtgcttag tccatagatt gataatactt acttgaagta | 31680 |
| aaatagtgaa tagaaaagga aatttaacaa aaaattatta ttagcaaatg ctaatatgac | 31740 |
| aagggtcagt cataatgtag agaattaatg cagtagatga gataaaattc cagcagttca | 31800 |
| ttgtaatatc atcagataat tgaacaatgt ggttatctct gagcggatat tttgaaaaga | 31860 |
| aaaaaaagc agttttttc agaagaacat ttatgctacc caaaactcaa tgttcccata | 31920 |
| tggtcagtag ggcaaaacaa gagtaaaaaa aatattgcta tacatagctc taaacatgag | 31980 |
| aaatttattt ttgttttcag aatagtatct aacatttcat gagatgccag ctaaaaatat | 32040 |
| cacagacatt ctctagagga agtttccaga atactatatt actagaccaa tatatatttt | 32100 |
| ggacaatatc ttgaccctag gaagcttcac gtttttcatt aggcctgctc agtttacttt | 32160 |
| tctcaaatcc ccagagcaac tgtcagctga aaggcaaaca tttctgtcat ctgatcataa | 32220 |
| agtcctgatg atatctctgg aaatttcagc agaagcaagc agatggcaga ccagtcagtc | 32280 |
| ttcctgtcaa tagtattgat ttctttggtt atttgaaatt agcatttaca tttatttcag | 32340 |
| tgcccagacg taactatgtt tttgaaaatg aatctacttt agaaaaataa gctaatacaa | 32400 |
| ttgaacaaag gagacactgt tacatttctg gttaaaaaaa aaaaaagcca ggcttcaaag | 32460 |
| tagtgatttt ttttttttta atggaaagca agaaagaatt ttggcatagc ctctgtacaa | 32520 |
| gccttgacat ctctcatata tttagatggt taaagtaaat ttatggcatt cttctctatc | 32580 |
| ttctaggaag gatgtaataa gcattctccc taacatttca gggtgaaggt cctttcttat | 32640 |
| ctagttaagt gtgcatttca aatatgcttc atggtatcca agaatataaa taacaaagag | 32700 |
| gaaaactcag agcctagag tccctactgg ggcctagctt gcagcatggc agagatcatt | 32760 |
| gtaacaactg attgcattat aattgtgtga atgactcaca agtctagcag aagtctgcac | 32820 |
| aataatagga ataatgttca ggtcaaaaga taacatcatg ttgaaactct attaagccaa | 32880 |
| tgagcaggag atggtcagca aagtcctctg gtgccctaga cttggttacc atgtggagat | 32940 |
| gcaacccagc taagcttaaa tgccttgtat acatggttct tacttagaaa taaagacaat | 33000 |
| cttgtgcatt tcaaataggc atctggtcac aacttccttt cctgtctaca tctatgcatt | 33060 |
| tgtttaaaag agtttaattt taagaacaat tgatattatg cattatggtt acttagtaat | 33120 |
| ttcacattta tcaattcatt ttattttctc agaaactcta taatatagct attaaatcca | 33180 |
| tgttttacag gtaagtctac aagaagttaa gtgattccat atttagtatc tttttttttt | 33240 |
| tttttttgag acagagtctc actctgttgc ccactcggga gtgcagtggt gccatctcgg | 33300 |
| ctcactgcaa cctccacctc ctaggttcaa gcgattctcc tgcctcagcc tcccaaatag | 33360 |
| gtgcctgcca ccacatccgg ctaattttg tatttttttt tactagagat ggggttcacc | 33420 |
| atgttggcca ggctggtctc gaactcctgg ccacaagtga tccacctgtc tcagccccc | 33480 |
| caaagtgctg ggattacagg tgtgagccac cactcctggc ccatgtttag gatttatacc | 33540 |
| aatattatta acttagaaat aagtttctaa taaattattc cacccgaact tagggtaact | 33600 |
| gaattttaat gctgatgtat taagcaggtt cttcctgggg tcttttgatt ctcaagggat | 33660 |

```
ccttcactga gggtggactt caaattaata ggaagcagga aggagccact tgcactgttt    33720
tcttgactgg ggatgacacc taaacctttc tgattgcatt acttgcccta tttatgactg    33780
gtctccctca ttgtaaaata aagactttgg atcacaggag tggttcttga ccttaataag    33840
tccagagtgt ttattacttt tttccaccaa tatttattgg taaaataaac cagaaggcat    33900
gtctattaag taataaataa tgctttcaaa ttttaagcta atcagtgaaa catatgttaa    33960
aacataatca tcctttgggc tattgagata ttaactataa tgatgagctt ccgttatcac    34020
cttgtggacc tctgggatg gagcatcttg aacggagaat cactggatta aataaagaga     34080
taaaactcaa gtatttttta actttaaact ttgatgaaaa ctctccggta aactggaata    34140
ctttagacaa tttccaaatg actagagaca acattaact tttgcctca gaaactctga      34200
tattttaaat cagtttgttt ttctggccca cttttttata aaatgaggaa actaagtcac    34260
agaggttaag tgacttgcct aagataaaag agggccaaac caggagtaga aacaacatca    34320
tttactcaca cggattctat acccaatcct gagccatgtg atctgcttcc ttctggcctc    34380
catgtcacat ggattcagga agaaatctga gttctaatag taatattgga gatgcaggga    34440
gaacttcttt attcacgtat gtattccttt cttttcttta aataactctc acaattttgg    34500
tcagtatttt caagaagaat ggtgtgtaca cccagtgggaa ggcatataca tcatgatgtt   34560
gttttttggaa ctgacatatt atgaaaaaaa aaagagactt acgttttctg tccacagatg   34620
gacttttat accagttctt acaagtgctg aagtatttct ttttggtgcc caaaatctgt     34680
tgaagggcac agacatttgg gctggaggat agagggaaag gaaaaaagtt aatgtcctaa    34740
taatgactag ttttttcgtat ctaaagattg gttgatagaa gaaaatgttg agatgtggat   34800
ttgatatcca aagacatgat tctagccttg cacaaatcta attattgaca caatcctact    34860
gaattgttga aaaaccgaaa gtctacagga ggtggcaggg agagagagaa aaattataca    34920
tttctgagag taaaatacaa gcttttcaaa aagttaacca actaggacta ttcaaacagt    34980
atgaacgtaa ttttatttct atgtgcctta ttactttaa tggtagataa tctactgacc     35040
cttttaaac caagcatgtg ctcatttgga ggatggccat aacttcaggg ctctctggaa     35100
caatgagagg tcagagagca aaagagacaa ggtttattat gtacacagac actatactct    35160
gtaatttct aggtaagtaa tcacagaagt aaatgtgcta aaattaactt tgaaacaata     35220
tggttgcaca aaggagaatt tatcttttg aatggaagta acagatcaga acatcctctg     35280
tcacaatttt aaggttcccc ttcccctctt aaagggacag aagtcttttt tcactgtaag   35340
tcaaagaagc ttgtgaacat tatgaaaatt cctgtgaggc ataggaagaa gtgccaagat    35400
ccgcttaaaa aattataaat ggttggataa gttacaaaat tatgtgtaat tttaaaaatg    35460
cttagttgta gttgcattag ttctataaaa tataaattac ctttgcaaat tttacagaat   35520
tcagagttta aaagtaactt aaatgcttca aagaattcag agaactagtt acattaccca    35580
gtatttaacc ttcatatgta atttaaataa aatttctct aacatcatgt gagatatttc     35640
aatgctgttt gcatacatat gatagttcct aacaatagat ttttaatttt tgaaaactca   35700
atttcagatt tttggaagaa aataaaaaca taaataaatg gaattataaa agaatgccca   35760
gctaaattgt gttaattaga ttagaattat ataacatttc ataagaaagc aatttatattc   35820
aaggtattta gagagcaatt aagtcttaaa gcttaaaagt gcatagataa atcacagaat   35880
actcacattt tccttttttt cctattactt tataataatt aggaaaaaaa accctgaggc    35940
atatatgaga aactttatgc atacttgaac atctaacaag ctgaggaaaa agaaaaatgg    36000
```

-continued

| | |
|---|---|
| tttataaaac caaaccactc acttaccctt ggtcccgacc cctgatacga ctatgagcca | 36060 |
| agatcttgtc ataatgattg ttggcgttta tagggttaac aataagcagc aatagtagag | 36120 |
| aaaacatggg taaaaaggga atcatcttga gtctctccgt tgcagttagt ccccgaagag | 36180 |
| aactggcagt gggctttgga gagctcagaa tttatataca tgtcagagtt gtgggaggga | 36240 |
| acactgcatc aacctgagag tct | 36263 |

<210> SEQ ID NO 29
<211> LENGTH: 11043
<212> TYPE: DNA
<213> ORGANISM: Homo sapiens
<220> FEATURE:
<223> OTHER INFORMATION: KLK6

<400> SEQUENCE: 29

| | |
|---|---|
| tcataataaa attcattctt tattgagtgc atggtggccc aggtgctatt ccatgtatgt | 60 |
| cataggtgtg aaaccttaaa tctttccaac agccactgcc ttatggagac tgtatcatcc | 120 |
| ttatcttcat cttacaggtg agaaatctgc agtgaagaaa ggtacatccc aaggggacac | 180 |
| cgacagtaag cagcggagct gggattccag acacgtggct gggcctctgc aggaagaaat | 240 |
| caaacgtgtg aagggttggg ggagaggaga tgcctagaag ggattttcct gtattctctt | 300 |
| agtggtgggg gtaagaccga ggacccaagt cctcactcat cacgtcctcc ccagtgatgc | 360 |
| aaggatggag ctggggtaaa accagggaga atcaggaccc tcacgtcgct gcgtttatta | 420 |
| agcatcaggg tcagagctgg gcaggagagg aggggaggca aggtctaggt gagagacgtt | 480 |
| ctggaaccag ccagtggggt ggtaggtcgg gaggtagatg tcacatgtca gggtcacttg | 540 |
| gcctgaatgg ttttttggat ccagttcgtg tatctgcaga cgttggtgta gactcctggc | 600 |
| ttctcctttg atccacaggg gatgttaccc catgacacaa ggcctcggag gtggtctcca | 660 |
| cataccagcg acccccaga atcaccctgc aggaaagagg gagaaagtca gatacagata | 720 |
| gaaacccaga gactgtgtgt gtgtgtgtgt gtgtgtgtgt gtgtgtgt gtgtgtgtga | 780 |
| cagagagaga ggtagaaagg gacagaggta cttactgaaa gatggagaga aagactcagg | 840 |
| gacagagaga cagagagaga gacagtaaga cacacaaagg cacagagaga gaatggtaga | 900 |
| gagagaataa aggagactca aagacacaga gataggaatg ccaagatgca gaggaacata | 960 |
| gagagcaaga aagagaaaca atttaagaat ggagactgag aggtgtggag agaggcagag | 1020 |
| gtgtagagac cgatggagag agaggaggag gaagaggaga aggaggagga agaggagaag | 1080 |
| gagaggagga agaggaggag gaagaggagg aggaggaaga ggaggaggaa gaggagaagg | 1140 |
| aggaggagga ggaagaggag gaggaagagg agaaggagga ggaggaagag gaggaggaag | 1200 |
| aggaagaa ggaggaagaa gaggaggagg aagaggagga ggaggaagag gaggaggagg | 1260 |
| aagaggagga ggagaaggaa gaggaggaga agaggaggaa aaggaggagg aggaaaaggg | 1320 |
| ggaggaggaa gaggaggagg aggaagagga gaacgaggag gaggaagagg agaaggaaga | 1380 |
| ggagaaggag gaggaggagg gggaagacga ggaggaggag ggagagaggg ggggaggagg | 1440 |
| aggggggagga ggaggggag gaggatgggg aggggagga ggatggagag ggggaggagg | 1500 |
| atggggaggg ggaggagggg gaggaggaga cgataagacc caggtgggag aggtagggag | 1560 |
| ggcccaggga gagatatgcc tggcactatt ctgtccaggg acacctctcc acctcgtgtc | 1620 |
| ttgaggacag tctcgcccac ctgccctttc tttgcgtcca acttgctatg tatcgctttc | 1680 |
| cctgtctctg tccctgtttc tgcctgtgtc tccgtttctg cctgtgtctc ccccttggtt | 1740 |
| ggtctctgca catccctcag tgcattagtc attctggcat aaagaggaga gcctggatgg | 1800 |

```
atgacaatgg aggaaaccca agttaaagta ttcgggaggg agtcccctttt cccagctag    1860 tgtctccctc ctccagagcc tggtcgtttc tgagcaggac tcgtgggggc tctgtttgag    1920
gaaggacagt cccctcacac catctgcttc cttactactt ctctttggtt cttttttgttt  1980 ttagacagag tctggctctg tccccaggct ggagtgcagt ggcgtgatct cagctcactg    2040
cagcctctgc ctcctgggtt aagcaattc tccagcctca gcctcccgag tagctgggac     2100
tacaggtgtg tcccaccatg cttgcgtaat ttttgttttt tggtttttttt ttgagacgga   2160 atcttgctct gttgccaggc tggagtgcag tagcatgatc tcgactcact gcaacaacct    2220
ccgcctccag gttcaagtga ttctcctgcc acagcctcct gagtagctgg gactacaggc    2280
gcctgccacc acgcccagct aattttttgta tttttagtag agatgaggtt tccccatatc   2340
ggccaggctg gtctcaatct cttgacctgg ttattcaccc acctcggcct cccaaggtgc    2400
tgggattaca ggcatgagcc actgtgccca tcctaatttt tgtatttta gtagagatag     2460 ggtttcacca tgttgatcag gctggtctcg aactcctgac cccaggtgat cctcctgctt    2520
cggcctccca aggtgctggg attacaggca tgagccactg tgcccatcct aatttttgta   2580
tttttagtag agatagggtt tcaccatgtt gatcaggctg gtctcgaact cctgaccca    2640 ggtgatcctc ctgcttcggc ctcccaaggt gctgggatta caggcatgag ccactgtgcc    2700
catcctaatt tttgtatttt tagtagagat agggtttcac catgttgatc aggctggtct   2760
cgaactcctg accctaggtg atcctcctgc ttcggcctcc caaagtgccg ggattacagg    2820
catgagccgc tgctcctggc ctctctggtt cttgatcccg cggcctccat ccttgtctct    2880
gcacttcctg tctctgctgg ctgtgtcttt atatctctgc atatccctga ctgtgtctct    2940
gtgtgttgaa ctaagtctct tcttttcaag gcttgggttc tccctcagcc tgtctctatc    3000
tgtctctgta aagctctctt ttggcctgtg tctctctctt cctgtgtctg gccatgtttt    3060
tgtgacttcg tcctgtccct ggctgtgtaa gtggcagatc cgggtcacct cacctggcag    3120
gaatccttcc cgtacttctc atccccagca cacaacatgt tctgggtgat ctggccaggg    3180
taggcatgct cacactcctc acgggacacc aggtggatgt atgcacactg gatggtgtca    3240
gggaaatcac ctgttagggg agagatgggc cagactcagc ccaggccttg cactcccctc    3300
atcctcccca gtcaccccc aaccccctata gtcctccat cctctattgg tccctctttt      3360
ctattggcac ccctcttcct gtttgtctct cattcttaca tctcattacc atcgtccctg    3420
cctcctaatt ggtccctctt tctatcattc ttccccccca ttggctgtct tcctcattaa    3480
tagtctcttc tccaggagtc ctcatttcct attggttttc cttttctctt aggtccctcc    3540 tccactttc tctcttccac tggtcccacc ttcttcagta gtttcagttg acctggagga    3600
ctcttcctct gttacgccct cctctactgt acccctcctg atcagtagtc cattcttcat    3660
tggacacttc ctgcccattg attcatcttg attggtcact ctgtgaccat ggtcttttc    3720 ctaactggcc atgccctctc ccattggttc ttcctttcta ttggttcttc atccaatggt    3780
ccacctccat cattggtcct tttctaactg tccccaccct ccctcatgga tcctcccttt    3840
ctattggccc ttcctccaat ggtctacctt cctcattggt cctttcctaa ctggccctgc    3900
cctccctcat tggctctctc ttcctattgg tctgcttccc tccttggtcc tttttctaact  3960 ggcctcacca tcccccactg gctctcccttc ctattagcc cttcatccaa tggtccacct    4020
ccctcattgg tccttttcta acttgccgca tcctccccca ttgtctctgc cttcccactg    4080
gcccttcatc caatggttca cctttcttat tggcccttca cacacaggcc caccttcatg    4140
```

```
gatcctgctg atctattgga cctgttttt cctctagtga ctcctctgga ccattgatcc    4200
tttcccctta gtccctcttc catcagctat accccattc actgtctcaa ttcacatcct    4260
tcagttggct tttgtgcttt attggtttct cttcttccat cagttccttc tccattattc    4320
cttcctgctg ttcaatgaat cctgatcagt ccccttgac ctttgacatc cttcctgatt    4380
agcatctccc cactgacctt ccctctttat tgaaccttca tcttatgttc catctctccc    4440
atgctattca cccattggtc tacattttcc attggctgtt cactcactgg cccagctccc    4500
aaattcactc tccctccccc ttgaccttc tcccattgaa accctgtccc attggtcctc    4560
accattagcc catcttccca tggcccctca ccaattttcc cactcccat cctttggcac    4620 acttccccaa gtagccagta gcctgctccc caccagcctc ccactactga ccatctgctg    4680
tcttgcccca gcccaggatg tggcagctgg tggtgttggc tgagcagtcc ctctccaggg    4740 gaagggctg gatgagttca gagagtttgg ctgggcgtgc caggcgcaac agcatgatgt    4800
cctggtcatg gctggcggca tcatagtcag ggtggatcac agcccggaca acagaactct    4860
gctcctggga actctccctt tgccgaaggt tatgcttccc caggaagacc tgaagattcc    4920
tgggaaggaa gagggctggg tctcacctgg agcccttggg ctgcagttga ggcttcagag    4980
agggctggga agtcatgaat cgctggcctg ctcctcccac agtcttcccc agctgggtaa    5040
atggcaattc catcctttca gaataatctt gggggctatt cttcactctc tttatttcat    5100
gccctacatc caagctgtcc agaattcctt ttgcctctct gaagcatatc cagaatctgg    5160
ccacatctca cctttcccac ggctaccatc ttggtttgag ctgccttttc acttcctacc    5220
tgaactagag cagtagcctc ctcactgggc tccctgctct gtctctggtc ccccacagtc    5280
catcctccac aaagcaacca gagatatttt aacaatgtaa gttggtcctg tgcctcctct    5340
gctcagcccc tcctatgact cccatctcac tcagaatcaa agccaaagtt ctcaacgtgg    5400
cacaccaggc cttgcaagca ctgccccatc atctcacaga catcttctcc tcccactctc    5460
cccttctctc cctctgctcc agccaaacgc tggcttccct gtcttgcctt gaacacaata    5520
gtgatcttcc cacctcaggg cctttgcact gctgttccct ctgccagcaa gtctgtcctc    5580
caagtatctg catagctcac tccctcactt ccttaaatg tcgcctctca gggaagcctt    5640
ccttagttgc ccaattaaaa tacaaatacc tgttagtagg caattcctat ctccctcccc    5700
tgctttctgt tccaccagag aacctatcac aatcatccga cctgctatat atttattgtt    5760
aaatatttac tcattgtgtt atttctcctc cttgcagagc aatgctgtcc actaaatgct    5820
acgatgccat gatctcgatc tgcactgtcc agaggtggct gggggaacca caagctacag    5880
gtggctgctg agtacttgaa atgtggcttg tggattttcc atttcattaa tttcaatgta    5940
atttgctata tgtggctgat ggctaccata ttagacagtg cagctctagg atgtcaagat    6000
ggggattttt gttctattca gatatagtat ctccagtgcg ttgatcagca cctggcacag    6060
gataggtgtt tgatacatat tcctgaaaca gagagtcact cccttgctca gacatcaccc    6120
atggctcccc attgtcctaa gaataaagcc tgggctcctc cacttggcac tggagcccct    6180
gtgtgatctg gctgtagtca ctttccaacc ttatctccca gcaccttctg cccccccagtg    6240 aacgggaaat tttattttct gagaatactc aagacggttc tcacctcagg ggtgttatca    6300
cagcctttcc tctgccctga acattccttt tcccatcttc atgcctccgc ttggatttta    6360
tctcattaga aagtccttcc tgaccctcct ccatctaaag taggtacccg tattctttc    6420 cttcataatt tgtaattata tggggttttg aagggtttgc ttcttttgtt tgtttgtttt    6480
tttgagacag ggtctcgctc tgtcacccag gctggatctg cagtggtgtt ctgtagatca    6540
```

```
cagctcactg cagctttgta ctcctgggct cgagtgatcc acccgcctcg gcctcccaaa    6600
gtgctgggat tacaggcatg agccaccacg gccagcccaa tttgctgctt ctttctttcc    6660
tttttttttt tttagacaga gtctcgctct gtggttcagg ctggagtgca gtggcgcgat    6720
ctcggctcac tgcaacctcc gcctcccacg ttcaagcaat tctcctgcct tagcctccca    6780
agttgctgga attacagaag cccaccacca cgcctggcta atttttttgta ttttcagtag    6840 agacagggtt gagccatgtt ggccaagctg gtctcgaact caggtaatcc acccacctcg    6900
gcctcccaaa gtgctgggat tacaggcgtg agccaccatg cccagccctc actttgcttg    6960
tctgcacctt tctgtccttg tgctcccgag ggcagggatg acgtgtgtgt cccatccatt    7020
gctgaatctc cactgcccaa ctcgaatgtg gcacttagca ggtgctctta gtcaatgtac    7080
atcaaaggaa tgaatgatgg tggtgagagt catccaaggt ctccttgggg tcaggggaac    7140
caccccaggg attgtcactt gctatttccc tgcacctcag tttcctcatt tgcaaaatgg    7200
tgccaagagt cccttgtggt gggcattcca ggaaaggtgt gtacatggtt tcactcagca    7260
cctgattggt agttagcatc aaacaagtgg cagctgtcgt gaatctgact agtgaggatc    7320
agcgcccagg gttttttgtcc tgggccctcc agctcctcca actatgccag ctttttggat    7380
gatctcatct agtcccatgg ctttaaatac acctgtttgc tgacgatgcc ttcattttaa    7440 cctcagccc tgacctctcc tctgagctcc agagtcctcc ctggcctccc tgctgggaca    7500
tctccccggc atctccaact catcgtggct aaagcaaaat gtcagatgct cccctgccta    7560
cacccggcct gtttctcttt ccctctccca caactcagag aaagacgtgg caaaacaccc    7620
agttgttcag gacaaataca cggaagccag ccgtgcttct tcctctccct cctgttcctc    7680
gttgccagat tctgctggct cagtctcaga attccacatc caagatatt caacatccct    7740 ccatcccac tgcgaccgcc tgggttcaag ccaccctcct atgtcgccgg atgaaagcaa    7800
cagcccccac gtgggcctcc ctccctctct cttgcccaga ccacgttcca cgtggtagcc    7860
agggtgcttg taaaaatgta aatcaggctg ggtgtggtgg tggctcatgc ctgtaatccc    7920
agctctttgg gagggcgagg cgggcggatc acctgaggtc aggagttcga gaccagcctg    7980
gccaacatgg tgaaaccccg tctctaccaa acatacaaaa attagccagg caaggtggtg    8040
cacacctgta atctcagcta cttggggtgc tgaggcagga gaatcgctgg aacctgggag    8100
gcagaggttg cagtgagctg agatcatgcc actacactcc agcctgggtg acagagcgag    8160
actgtgtctc aaaaaacaaa caaacaacaa aaacaaaact gcccagtggc ttcctactgt    8220
gctcagaatt aaatccaaat gcccatcacg ccctgcaggt cccaaaatga tccaattccc    8280
ccattagaaa gtaagttcag gaaaacagca attttgcttg tttttttttg ttttcttttt    8340
tttattttct tttccactgc tatgcccgca gggcctggca cacattaagt actcaattaa    8400
gcaacagccg aatgcacctg gctatcagat ggcctcgtgc tgggatgggg gggatgccta    8460
tgtcacctcc tgcctgacat ctataagaca ccctcagggt tcagtcgcat ctgctgttca    8520
tttacagtgt agactcacgg tttttgcag tgggcagctg tgaggaccca cagtggatgg    8580
ataaggaccc caccacagag caagtggccc gaggtgtaga gggcagcttg gtaggggtga    8640
gatgtcttgt cgcagggtcc gccatgcacc aacttattct gctcctctgc ccaggctgag    8700
ggagagaaga tctgagtcag agaggagttc tggagaaacc aagcgcatcc ccctcaacat    8760
gaactccagt caagattggt caggtgcagt ggcttatgcc tgtaatccca gctgaggcag    8820
gaggatcgct tgagcccagg agtttgagac cagcctcggt aacacagtga gacctcatct    8880
```

```
ccacacacac acacacacac acacacacac acacacacac aaattagcag ggtatggtgg    8940
catacgcctg tagtcccagc tacttgggag gctgaggtgg gagggtcact tgagacccaa    9000
gagttcaagt ctgcagtgaa ctatggatca tgccactaca ctccagcctg ggtgacagag    9060
tgagaccctg tctcaaaaaa aaaaagcttc tctgtatttc cactcccaaa cttaccccat    9120
tcccattaca aacccaactg tatcccctat tcccgggctc tctccaactt ccaacctac     9180
ctcctacctc ttctatgttt agatccccat ccctaaagcc aacccaccc caaaccctca     9240
tatcttcaaa cccacctccc accaccctcc ctatctgtat tccccaccct tagcctaatc    9300
cccaacgtct tcctcatttc aaagctcccc caccccaacc ctgtgcatat ccccatcccc    9360
aataccagcc tcttctccat caacaagccc aaccctgtct gcaagcctcc cccatccaaa    9420
tgcccttttcc ccacctgcag caatcagact cagcaccacc atcagcttct tcatggccgc   9480
tcctgagagg ggaagccaca tggtccatta gtcactgcct cgaccctccc ccatccctc     9540
tgtctgctcc ctctgcatcc tctccttcct tcctggcctg ctatggtctc ctgccttgac    9600
ctctgtcctt cccatctagc ctcctgattt attcttcctc agcccacatc ttccatcaga    9660
ggatcccacg aaaacagtgc caaagagaat tcagaactac gtccactggt ccagtaaccc    9720
atggtgagat tctgattaga tctttctact ttcttgggca ctgatttgcc ttcctgtcga    9780
caggagaggg ttaccctagg gggccctagc gttcttcctc tgtatgggag ttttcctcgg    9840
agcctggctc tgtgcgcaat ggccacccac cccgcccacc cggcaggttc tgtgatgtct    9900
gtgatctcac ctgctgcagg cctccgggct ccggggattc ttgagtcggg ggaaggaaca    9960
gctttgagac gaggaggcag aaagagttag aaatgcgggg agccgtgagg agagaagaca   10020
ctcagatgca gtggcagagc caagcggagg acgcagggcc cgcagagccc agggctgcag   10080
ggactgccag acacacaccc ccagctccca ggcctccctg gaagaggctg gttctgtccc   10140
cagatgcttc tggaacgtcc ttttaacccc tgtctctcag gtccctgagc caggagactg   10200
gctacaccct tttcctcctt acccaggcct cccacacaca ttcctcccgc ccccacgctc   10260
tgctcttggt gaccctgac caggcctcca gggaagggag cactggtccc tgagtgcagt    10320
gagggcctgg actcctgggt ctgagggagg aggggcttgg gggcctggac tcctgagtct   10380
gagggaggag gggctggggg cctggaccct tgcgtctgag ggaggagggg cttgggcct    10440
ggactcctgg gtctgaggga ggaggtgaga acttggactc ctgggtctga gggaggaggg   10500
gctgggggcc tggactcctg agtctgaggg aggaggtggg aacttggact cctgggtctg   10560
agggaggagg ggctaggacc taaactcctg ggtctgaggg aggagggct ggggcctgaa    10620
tctgaggcag aggaagttct agtcggctca gtccttagac ctccgggttt tggagaaaga   10680
aagtgtctga agacaaattc cggcctctgg ggcaagcaga tggtgcccca ggcctccctg   10740
cacccccagc actctctgtg ccacccaggg acctgcaggc cctcactccg ggctctagag   10800
ccctccggca ctgggaagca gcctgccag gttcagtgcg gttggggtga ctcacacacc    10860
tgcccgtagg tccctctgtg tgctgcctgc cgacctctgt gtcccagga gagagcgagc    10920
cagccagccg gggagacagc tacagcgtgt gtcaccacac tggccccgc ccctgccccg    10980
ggctggggag caggcccagg cgcgatgggg aaagggccca ggaacaatcg ggctttgtcc   11040
gcc                                                                 11043
```

<210> SEQ ID NO 30
<211> LENGTH: 35634
<212> TYPE: DNA
<213> ORGANISM: Homo sapiens

<220> FEATURE:
<223> OTHER INFORMATION: MUC2

<400> SEQUENCE: 30

```
caacccacac cgcccctgcc agccaccatg gggctgccac tagcccgcct ggcggctgtg      60
tgcctggccc tgtctttggc aggggctcg gagctccaga caggtgagag agcagacaca     120
ggggtctggg gcctggcaga gtgtcctggg ggcagggcga ggcgggcggg caagtcgcgt     180
ctgggaggag gagctggtcc cagagtgcag cctgcgcggc tctgctgagg ctcctggccc     240
gggttggtcc ctggaagccc ccggccctgc tgactttcaa ggagctggaa ggtcggggct     300
cccctgctat tcctttgggg ttgactgccc gacgacagtg tgggtcttgg ggccagcacc     360
aggtggaaac agcaggtcag gccccagtga actgggtcat tgtccatagg ggaggaaggg     420
gtggccagga tcccaccaga aggccccatt ctcaggtggc agagacccctt gaagagttgg     480 ggcagcacag cccttgctgg ggagcgggt gcccagaatg ccctctccta catcccgctt     540
ggcacccggc cgcactcctc accaggccgg gggtagaagc cctgagaccc ctgtggtggg     600
gtgaccaagg cccagcagag ggcccgagga taggaaggaa cctttcccgg ccaggggccc     660
tgtgctgggc tcgaagctgc ttccaggtgc ttcttcaggg gccttctctc gagggtagct     720
tgggcagcct tccccctccg gggccactca cccctcattc ccgctgctc cctcagaggg     780 cagaacccga aaccacggcc acaacgtctg cagcacctgg ggcaacttcc actacaagac     840
cttcgacggg gacgtcttcc gcttccccgg cccctgcgac tacaacttcg cctccgactg     900
ccgaggctcc tacaaggaat ttgctgtgca cctgaagcgg ggtccgggcc aggctgaggc     960
ccccgccggg gtggagtcca tcctgctgac catcaaggat gacaccatct acctcacccg    1020
ccacctggct gtgcttaacg gggccgtgtg agtgtggtcg gtggcacccc tcccacatcc    1080
tagcaacggg ggctgatgtt tcccaaaggg atattccttg tagccctaga agacccccttc    1140 cgccccagca cacagctcag gagaacagcc ttgaggttg ggttcaggtc actaattcat    1200
tcaacaaaca ctgatgagcc cccaccattc cccccatagg caagggggtttt cagttatccc    1260 tttgcctgtg tgtccctgac agcccctccc ctcggagccc accaggctcc ggacagactt    1320 ggcaccctg gaggctgcat gtctctggtc ctgtgcatgg agtggccgtg tgtgccctcc    1380
ccaggctaga gttacagaag ccggtgcagg gggctgtggg accccttcc ccatccccag    1440 ctattgctcc cctattgtct ccagaacaat gaggccctgt aagtgcgttc ccatccagcg    1500 cctgccctc ttctgcctgg ggatttagtt tcctgcaagg cgccccagca tgggcatggg    1560
caggcgggtg gaggccctca ggcatgggca tgggcaggcg ggtgggtaga ggccctcagg    1620
cgtgagtgcg ggcgggtggg tggatagaag ccgtcaggca tgggtgcagg cgggtgggta    1680
gaggtcctca ggtgtgggca tgggcaggtg ggtgggtaga ggccgtcagg tgtgggcgcg    1740
ggtgggtggg tagaggccct caggcatggg tgcaggcggg tgggtgggta gaggccctca    1800 ggcgtgggc cggtgggtg gatagaggcc gtcaggcgta ggtgcgggcg ggtgggtaga    1860
ggtcctcagg tgtgggcgca ggtgggtggg tgggtagagg ccctcaggca tggcacaggt    1920
gggtgggtag aggccctcag gcatgggcgc aggcgggtgg gtgggtaggg ccctcaggc    1980 atgggtgttg gcaggtgggt gggtagaggc tttcaggcat gggcaggcag gtagaggccc    2040
ttgaggaccg aggcacagag gctggggtga gtgcctctac ctggaccagc aagggcact    2100 ggcaggaggt gggtagggc ccctgacgtt tcaggggca gctgggggg ctctgggggg    2160 tttgggaccc catggggga tgttccacca agcagggggc ctggaagggg gctgggcagc    2220
```

```
ctggtcctcc ctcctctccc aacctggtgc cctcagggcc tctgagggg gaccctgccc      2280
aggaccgtgc cccgaggagg gagtggagag gaggggcgtg caggcaggag gtggctctgc      2340
cggggaagcc cggccagcgg agatggacag gtgctctttg gccactgcct atgtccctcc      2400
accccagagg ccggccaagt tggtgatccc agggcaggag ctgggcctgg cagagccatc      2460
tccaccaccc caggtgccca gcttcagtcc cctctgggcg gcggggtccc gggaggacaa      2520
gctggggcgg gggggcctgg gtggtggacc caagagtgac cccgatgtgc ctccgccagg      2580
gtcagcaccc cgcactacag ccccgggctg ctcattgaga agagcgatgc ctacaccaaa      2640
gtctactccc gcgccggcct caccctcatg tggaaccggg aggatgcact catggtgctc      2700
aggggtcccc ggactcgtgg ggctggtggg ggctccgtca ggcctctggg cagacccaa      2760
gggagggcag ggagggcagt gctctgaccc ctcaccgaga gggcatgggt ggggcagggc      2820
ctcggcagcg cagggcgtcg gtgctggact tggggggcag cagcagaagc cgacctggcc      2880
ctgaccccc caggcctcag ccttccccca aacgcactcg gcttctcagg gacctgccct      2940
gccaggccgc tccctggctg ctgaccccag ccttcctgcc ccaccttcct ctggctcaaa      3000
caagccacga gtcttggggg ttcctggcgg ctgtgggccg gcgggaggc cagctcacct       3060
gctccctccc gcaacagctg gagctggaca ctaagttccg gaaccacacc tgtggcctct     3120
gcggggacta caacggcctg cagagctatt cagaattcct ctctgacggt gaggcccgga     3180
gggcttggag gggggcagggt aggctacggg ccccaggag ccctagctga agggccgtgc     3240
atccccaggc gtgctcttca gtccctgga gtttgggaac atgcagaaga tcaaccagcc     3300
cgatgtggtg tgtgaggatc ccgaggagga ggtggcccc gcatcctgct ccgagcacgt     3360
gagtcccctc ggtccggggt gggggtcctg gcggagctgg cctctgaata gcatgctcac     3420
cctgcgtctg tccccagcgc gccgagtgtg agaggctgct gaccgccgag gccttcgcgg    3480
actgtcagga cctggtgccg ctggagccgt atctgcgcgc ctgccagcag gaccgctgcc    3540
ggtgcccggg cggtgacacc tgcgtctgca gcaccgtggc cgagttctcc cgccagtgct    3600
cccacgccgg cggccggccc gggaactgga ggaccgccac gctctgccgt aagcccggc     3660
gccttgtggg caggggaccc cagggagacc ccacgctggt gctttcccca agcccggtg     3720
ggagctgtgt ctgtgccggg caccttgagc tggggggaca ctcaccgcac cgggcacctt    3780
gagctggggg aacactaacc gtgccgggca ccggagctg gggggacact caccgtgccg     3840
ggcaccttga gctgggggga cactcaccgt gccgggcacc gggagctggg gggacactca    3900
ccacgggcac cgagagctgg ggggacactc accgtgccgg gcaccgggag ctgggggac    3960
actcaccgtg acgggcaccg ggagctgggg ggacactcac cgtgacgggc accgggagct    4020
gggggggacac tcaccgtgcc gggcaccggg agctgggggg acactcacca cgggcaccgg    4080
gagctggggg gacactcacc gtgccgggca ccttgagctg ggggacact caccgtgccg     4140
ggcaccggga gctgggggga cactcaccgt gccgggcacc gggagctggg gggacactca    4200
ccgcgccggg caccggagc tggggggaca ctcaccgtgc cgggcaccgg gagctggggg     4260
gacactcacc acgggcaccg agagctgggg ggacactcac cgcgccgggc accggagct    4320
ggggggacac tcactgtgac gggcaccggg agctgggggg acactcaccg tgccgggcac    4380
cgggagctgg ggggacactc accacgggca ctggagctg ggggacact cactgagggc      4440
accgggagct gggggacac tcactgtgac gggcaccgag agctggggg acactcactg      4500
tgacgggcac cggagctgg ggggacactc actgtgacgg gcaccgggag ctgggggac      4560
actcaccgtg ccgggcaccg ggagctgggg ggacactcac tgagggcacc gggagctggg    4620
```

```
gggacactca ccgtgccggg caccgggagc tgggggggaca ctcaccacgg gcaccgggag    4680 ctgggggggac actcaccgtg ccgggcaccg ggagctgggg ggacactcac cgtgccggc    4740 accgggagct ggggggacac tcactgaggg caccgggagc tgggggggaca ctcactgtga    4800 cgggcaccga gagctggggg gacactcact gtgacgggca ccgggagctg ggggggacact    4860 cactgtgacg ggcaccggga gctgggggga cactcaccgt gccgggcacc gggagctggg    4920
gggacactca ctgagggcac cgggagctgg gggacactc accgcgccgg gcaccgggag    4980 ctgggggggac actcactgag ggcaccgaga gctgggggga cactcactgt gacgggcacc    5040
gggagctggg gggacactca ccgcgccggg caccgggagc tgggggggaca ctcaccgtga    5100 cgggcaccga gagctggggg gacactcact gtgacgggca ccttgagctg ggggggacact    5160 caccacgggc actgggagct ggggggacac tcaccgcgcc gggcaccggg agctgggggg    5220
acactcactg agggcaccgg gagctggggg gacactcacc gtgccgggca ccgggagctg    5280 ggggggacact cactgagggc accgggagct ggggggacac tcactgaggg caccgggagc    5340 tgggggggaca ctcactgagg gcaccaagag ctggggggac actcaccacg ggcaccgaga    5400
gctgggggga cactcaccgt gacgggcacc gggagctggg gggacactca ccacgggcac    5460
cgggagctgg ggggacactc accgtgacgg gcaccgggag ctgggggggac actcactgag    5520 ggcaccggga gctggggggga cactcaccac gggcaccggg agctgggggg acactcaccg    5580
cgccgggcac cgggagctgg ggggacactc accacgggca ctgggagctg ggggggacact    5640 caccacgggc actgggagct ggggggacac tcaccacggg caccgggagc tgggggggaca    5700 ctcaccgtga cgggcaccgg gagctggggg gacactcacc acgggcaccg ggagctgggg    5760
ggacactcac cacgggcacc gggagctggg ggacactca ccacgggcac cgggagctgg    5820
ggggacactc accgcgggca ctgggagctg ggggggacact caccacgggc actgggagct    5880
ggggggacac tcaccacggg caccgggagc tgggggggaca ctcaccgtga cgggcaccgg    5940 gagctgggg gacactcacc acgggcaccg ggagctgggg ggacactcac cacgggcacc    6000
gggagctggg gggacactca ccacgggcac cgggagctgg ggggacactc accgtgccgg    6060
gcaccgggag ctggggggac actcactgag ggcaccggga gctggggggga cactcaccac    6120 gggcaccgag agctgggggg acactcactg tgccgggcac cgggagctgg ggggacactc    6180
accacgggca ccgggagctg ggggggacact caccgtgacg ggcaccggga gctgggggga    6240
cactcaccac gggcaccggg agctgggggg acactcaccg tgccgggcac cgggagctgg    6300
ggggacactc actgagggca ccgggagctg ggggggacact caccacgggc accgagagct    6360
ggggggacac tcactgtgcc gggcaccggg agctgggggg acactcacca cgggcaccgg    6420
gagctggggg gacactcacc gtgacgggca ccgggagctg ggggggacact cactgagggc    6480 accgggagct ggggggacac tcaccacggg caccgggagc tgggggggaca ctcaccacgg    6540 gcaccggaga ctgggggggac actcaccgtg ccgggcaccg ggagctgggg ggacactcac    6600
cacgggcacc gggagctggg gggacactca ccacgggcac cgggagctgg ggggacactc    6660
accgcgccgg gcaccgggag ctgggggggac actcaccgtg ggctgagagc ccttctcggt    6720
gcacttcggg gtggagcggc tgctgtgccc cagcctcacc ctcactgcgt ggcctctgcg    6780
gttccagcca agacctgccc cgggaacctg gtgtacctgg agagcggctc gccctgcatg    6840
gacacctgct cacacctgga ggtgagcagc ctgtgcgagg agcaccgcat ggacggctgt    6900
ttctgcccag aaggtgcgtg tggaggatgg ccccgccctg gcactgccca ccagatgaga    6960
```

```
ggcagccctg gcctggggtt ctcgcctgcg ctgagggac  ggctccgctg gtggtgggg   7020
gcagcggcgg cacagaagtg cctctccctc cacccgatac cggggagaa  ggggcctcgg  7080
tgtgaggccc ttcccaaagg gtggcttcag ggaggccggg aagggggctg ccttcctggt  7140
tatcaccctg gggacagacc tcctcctgcc cggccctgg  cctggtgcct gaggcctttg  7200
ggagcagctc gattgtcagg ggcaggaagg tggcctggag gctggacccc catggccaga  7260
ccccaaccca gggaccaggt ggggaccgca ggcgtcagca caggggacca gtggtgcctg  7320
cgggtgggag gcctggctgg cagcccctcg gtggggattc tggctctttc tgagccagcc  7380
ggggtgacat cgcctccctg gctgtcccag gcaccgtata tgacgacatc ggggacagtg  7440
gctgcgttcc tgtgagccag tgccactgca ggctgcacgg acacctgtac acccgggcc   7500
aggagatcac caatgactgc gagcagtggt gagtcccggg gccagggctg gcacagcag   7560
aggctggggc ggctgagccc tgaccctgtg ccccgctgcc aacagtgtc  tgtaacgctg  7620
gccgctgggt gtgcaaagac ctgccctgcc ccggcacctg tgccctggaa ggcggctccc  7680
acatcaccac cttcgatggg aagacgtaca ccttccacgg ggactgctac tatgtcctgg  7740
ccaaggtagg ctgcccaggg tctggggcat ggggcagagc tggggctggc atccaggccc  7800
ttggctgtcc cggggtgggt gggctggctg tccctgaagc agagggtgcc tgtgggctgt  7860
cctggggcag gtgaccatgc ttctgctctc tggctggaga ataagaagca ggccttcctt  7920
tctaagccac tgccgggtcc tagggtgcag ggtgctgccc gtcccggccc tcagcagctg  7980
cactgcctct tgccccatca cagggtgacc acaacgattc ctacgctctc ctgggcgagc  8040
tggcccctg  tggctccaca gacaagcaga cctgcctgaa gacggtggtg ctgctggctg  8100
acaagaagaa gaatgtgagt ggtcctgccc cctccttctg gagccccagg tccccgagg   8160
ggggcccttc tcagccctga gcaacctcgg ccttccctgc aggtggtggt cttcaagtcc  8220
gatggcagtg tactgctcaa cgagctgcag gtgaacctgc ccacgtgac  cggtgagttg  8280
cgccccaggg aggggcccgg gcccttcgag ctccactggg cctgcagtga ttcggacagt  8340
ccagccacct cggacccagg aggctgggtg ggaaggttcc acgggggag  ggtccctgcg  8400
gcacccagca ggctccgtcc tgggtcctct gctggagggg gtggtgggag ggtgacaccc  8460
tcccgctgct cacctgggcc aggcaggtcc cgggagcccc gcccctcgcc atgcccctta   8520
ccgtgtccct catcgtgccc ctgcccacag cgagcttctc tgtcttccgc ccgtcttcct  8580
accacatcat ggtgagcatg gccattggcg tccggctgca ggtgcagctg gccccagtca  8640
tgcaactctt tgtgacactg gaccaggcct cccaggggca ggtgcagggt aagtggcccc  8700
accggggttg ccccaacaaa ggcccacagg ggggcctgct agccccagac tcttcccaac  8760
cctgtcctgg cccctcaggc ctctgcggga acttcaacgg cctggaaggt gacgacttca  8820
agacggccag cgggctggtg gaggccacgg gggccggctt tgccaacacc tggaaggcac  8880
agtcaacctg ccatgacaag ctggactggt tggacgatcc ctgctccctg aacatcgaga  8940
gcggtgaggc tcggcaacac gggcgccccc acctagcgtg cctagggtac ccggcccatg  9000
gcctggaagg gcagacgggg ctcccagcag gaagcatggg tggtgagggg cagaagtgag  9060
gtggctctcc tccagggca  gcccggcccc tgctgcttcc tgctgtggct agtttatggc  9120
ggccatggtg gcagcctgcc aggtgacctg gaagagggcc tgggctggtc cctacctgcc  9180
ccgtcatgtc caggatgctg ggcccttggg ggtgagagac gggaggtggt gggtgccctg  9240
caggggtttc tatctagcca ggagctgcct ggaaatttga ctcacgggga ggaagggcc   9300
tgggcatcgg tgcacagagg gaaccatatc tggggcctag gcagccaggc agcagggccc  9360
```

```
aggggatctc acgggggtcc cgggccccgc tgaagttccg atcccccact ccccagccaa    9420
ctacgccgag cactggtgct ccctcctgaa gaagacagag accccctttg gcaggtgcca    9480
ctcggctgtg accctgctg agtattacaa ggtgggtggg acccacaccc ccaggccccc    9540
atgccatcaa ggtggactca gggcaccccc agcccccat gccaccgtg aggtggactc     9600
agagcacccg gttgggccca ctggttgctg tgtgtgcgtg tgagcttgcg tctgtgagcg    9660
ccaggccaca ctctgcctcc ctgcctcact gcccgtccac cttgctctgt cgcccagagg    9720
tgcaaatatg acacgtgtaa ctgtcagaac aatgaggact gcctgtgcgc cgccctgtcc    9780
tcctacgcgc cgcctgcac cgccaagggc gtcatgctgt ggggctggcg ggagcatgtc    9840
tgcagtgagt gccgtccccg tgggctgcat cctggggatg gggtccgggc tttgagctcc    9900
tgggacgggg ctgggggccc tgagcacggg tggtccaggg agaggggttg gcccctgca    9960
gccacggacc aggctccagc ttcgtcggcc ggtggtagca ggaaaccagc aactcctata   10020
gcaaggggcg gccacgtagc aggggcagaa cctggggtgg gcctggagct gtggcggccg   10080
agtgtgggag tgggtcccag agtgtgcact ccctggcccc ctggccaccc tggggatggg   10140
agctgggcgt ctggctcttc ccgtccctca ccaccacccg tggtcctctg cagacaagga   10200
tgtgggctcc tgccccaact cgcaggtctt cctgtacaac ctgaccacct gccagcagac   10260
ctgccgctcc ctctccgagg ccgacagcca ctgtctcgag ggctttgcgc ctgtggacgg   10320
ctgcggctgc cctgaccaca ccttcctgga cgagaagggc cgctgcgtac ccctggccaa   10380
gtgctcctgt taccaccgcg gtctctacct ggaggcgggg gacgtggtcg tcaggcagga   10440
agaacgatgg tgggtacctg ctcggggtc aggtgtggcg tggggcggg ggaactcctt    10500
ctgaacctgc cccaagcgga gacctgggag tctctacctg ggaagctga gacacccaag    10560
gctgaggggt gcctggggtg ggggcgctg agaggcatca ggctcacatc tgcggggaag   10620
ctgctggctg tctgtggccg tcctgcatgg gccccgctca tccctggcct tttccacagt   10680
gtgtgccggg atgggcggct gcactgtagg cagatccggc tgatcggcca gagtaagtgg   10740
cactgccccg gccaccccte cccagccacc cctccctgcc tgccctggcc acctccccg    10800
gccacccctc ccgggcctgc ctgagaccct cagcttcagc tggagctgag gtggcccctc   10860
cgtcccacag gctgcacggc cccaaagatc cacatggact gcagcaacct gactgcactg   10920
gccacctcga agccccgagc cctcagctgc cagacgctgg ccgccggcta tgtgcgtgtt   10980
ggggggcgctg ctgtgggcgg gcagggattc ctggctggct gagcctggct cttgtgctgt   11040
gccccgcta gggtctgggt gccgagtcct gaggacgcag gccctgttga tgctgtccct   11100
ggccctggga gggaagtggc agcctgtgag ccactggggc acaggggcca gtgtagggcc   11160
cttggccgg agcctcacc agtctcactg ccctgtggcg ggcccaaggg gagggaagcc    11220
tgagcccagg ccaggggag tggtgggagg tctgggacat gacagagact gcatggtcag    11280
gcctttcctg gttgcacatc caatcctgac cccaggagg gctgcagcct cacctgtcca    11340
cccctgaacc ccactctctg gctgtcccca gtaccacaca gagtgtgtca gtggctgtgt   11400
gtgccccgac gggctgatgg atgacggccg gggtggctgc gtggtggaga aggaatgccc   11460
ttgcgtccat aacaacgacc tgtattcttc cggcgccaag atcaaggtgg actgcaatac   11520
ctggtaagct ggcccggcct gtcctggctg cctcccaggc ccacgtgct ccgcagggt    11580
ggccactgga gagcggtcca aggggcaagt gcctctcctg ggggttccgc ctgggtcttg   11640
cgagatcctg tggtggcccc tgtcccacgg gcagggtggt ctctcatgtc aaccgctggt   11700
```

-continued

```
cttgaagcca tggggaagg  gacatttgga gccacttttg gggcctgcag gtgtcctgtg   11760
tgggaggcac agggagctgt ctgcacggtg cccagggtct cctccagcca cccatgagca   11820
ggtcctgggt cccttcaggc tcctctcctg tcctcctcag cacctgcaag agaggacgct   11880
gggtgtgcac ccaggctgtg tgccatggca cctgctccat ttacgggagt ggccactaca   11940
tcacctttga cgggaagtac tacgactttg acggacactg ctcctacgtg ctgttcagg    12000 tgtggtcacg ggcactgcct ggtcgggctg cttatggtca gggaccctct gcctgcccca   12060
agtgcagtgc ttagctcccc gagaaaccct gagacttggg aaggccggcc tttcctcagc   12120
cccagacccg cacctgcacc cgcaggagga ttcgttcttc tagccagggc tgggtagggg   12180
tggtaaaacc cctctgtact gcccagttct gtggttctcc tctgggtcct cctccgggtc   12240
ctcctccggg tcctcatctg ggtcctccct cctctggcct cctctgggtc ctccctcctc   12300
tgggtcctcc tctgggtcct cccctcctctg gcctcctctg ggtcctccct cctctgggtc   12360
ctccctcctc tgggtcctcc tccaggtcct cctctgggtc ctccctcctc tgggtcctcc   12420
ctcctctggg tcctcctcca ggtcctcctc tgggtcctcc ctcctctggg tcctcctctg   12480
ggtcctcctc tgagtcctcc ctcctctggg tcctcctcta ggtcctcctc tgtggtcctc   12540
atttgggtcc tcctctgggt cctcctctgg gtccttctct gggtgcacaa ggtgggtgca   12600
ccagccatgg ggactgaggg cacctgtttg gggagctgag taaaggccag ggctaggccg   12660
ctgcccgcgc ggctctccag atccaaatcc cacagccctt tgaggcaccg tgatccccag   12720
ggacagggga caggcctgca gcagggtcag gtccttggat gggccaggcc agggcctggt   12780
ttgtctgctc agtggctgtg accctgccaa ctggggcggg tgtgccccgg acacctggg    12840 gtccagctgt cctggctgac cttgccctcc tggcccccag gactactgcg ccagaactc    12900 ctcactgggc tcattcagca tcatcaccga gaacgtcccc tgtggcacta cgggcgtcac   12960
ctgctccaag gccatcaaga tcttcatggg ggtgagtgct gctggccctg ggacgcgtg    13020 agccctgcgg gaccctcaga ccagccagtg actgggcctc tcctccgggc agaggacgga   13080
gctgaagttg gaagacaagc accgtgtggt gatccagcgt gatgagggtc accacgtggc   13140
ctacaccacg cgggaggtgg gccagtacct ggtggtggag tccagcacgg gcatcatcgt   13200
catctgggac aagaggacca ccgtgttcat caagctggct ccctcctaca aggtgggctg   13260
cctcccgtcc tgccctgccc cctcctggcc agccccccac ccctgccct  ggtgtttgca   13320 ggacaagccc ctgtcctccc tccagcccct ttttggagcc cctgtgatgc ttgtctcttg   13380
cagggcaccg tgtgtggcct gtgtgggaac tttgaccacc gctccaacaa cgacttcacc   13440
acgcgggacc acatggtggt gagcagcgag ctggacttcg gaacagctg gaaggaggcc    13500 cccacctgcc cagatgtgag caccaaccce gagccctgca gcctgaaccc gcaccgccgc   13560
tcctgggccg agaagcagtg cagcatcctc aaaagcagcg tgttcagcat ctgccacagc   13620
aaggtgggct ggccgggcca tggtggggca agtaggcaga ggagggctgt aggtgggctg   13680
tgactgtggg ctggggccat gggcggggcc gactgtaggc agagcaggc tgtagggggc    13740 ctgtgactat aggccgggc atggcgggc taactaggca gagcagggct gtaggtgggc    13800
tacagctgtg ggcggggcca tgggcggggc cgactaagca gagcagggct gtaggtgggc    13860
tatagctgtg ggcggggcca cgggcgggc cgactgtagg cagagcaggg ctgtaggtgg    13920
actatagctg tgggcgggc catgggcggg gccgactgta ggcagagcag gctgtaggt    13980 gggctgtggc tgtgggcggg gccgactagg cagagcgggg ctatgggctg actgtggacg   14040
tggtgagggt gccgtagagc atgctaatga ccagggcgtg gtcatagcag ggtagggtct   14100
```

```
tgggtgctcc tggggctggg gggcttctcc acatgctccc cacaccttca ggagtcgccc    14160
tgctgcgtca cgcaccacac ggcgcttgtc ctccagcttt ggctctggcc gctgcctcct    14220
ttggtcacat gaccgtataa tcggcctccc ctctgagacc ctgggctgga ccccggcct    14280 ccctctgcct ccccaggctc agatattcac ccggagggag aaaggacatg tgtcccccat    14340
gcccacacat ccccagctac aggcagctgg ggaggacggg ttctaggatg gccatgttac    14400
agctgaggat gcagaggggt tgggtgatgg gtctgcacag ccacggcggg acaggtgtct    14460
ctggaccctc tccccaaggt tggccctgcc ggggccctgg ctggctggtg ctgggtaatg    14520
tgccctgtcc caggagcagg gccggcctca gggtcctgag ctccagggca ctggggaagt    14580
cctggctcca tgagggcagc acgggcccag acagaccagg ggtgttctcc ccaggtggac    14640
cccaagccct tctacgaggc ctgtgtgcac gactcgtgct cctgtgacac gggtggggac    14700
tgtgagtgct tctgctctgc cgtggcctcc tacgcccagg agtgtaccaa agaggggcc     14760 tgcgtgttct ggaggacgcc ggacctgtgc cgtaagagcc tgcccgaact gcactcaggg    14820
ccgggacggg ggctgggagg tgctgtattg cgggccgggg tgacactcct tgtccatcca    14880
ggtgatgggt gtgcatcacc caccctttcc ccgacttctc cagtgtcctt ctttggggcc    14940
ctgtgggacc cgggttggca gagcaagctt gatgcgtctg cgtcccagcc cccgacccca    15000
gattcgccct caccccggcc caggcctgag ccctcctgcg tctgaccctg gcctgtctc     15060 ccccaagcca tattctgcga ctactacaac cctccgcatg agtgtgagtg gcactatgag    15120
ccatgtggga accggagctt cgagacctgc aggaccatca atggcatcca ctccaacatc    15180
tccgtgtcct acctggaggg tgagcagggt ggggcgggct tcagcggggg tgatggccga    15240
ggggcctgga ggctgagtgg ggcagccctc gggagaggca acagtccact ggcctggagg    15300
gtgagccagg cggccctcgg gggaggctac ggccgacggg cctggcactg tggggctgaa    15360
ggctgatgtc tggagaccca tggggacacc cggagggagg cctgaccctc agggtaccca    15420
cagcccaggg cagccaggct ccccttgctg caggatcagg agggaagcag gctatcgtgg    15480
aaactgggag tggcagggt gggaggtgct gaggttcgtg cagagcaggg cgggttgggg     15540
agcatttcag gcacaggtca ggggaggccc ctgccgggtc ctggtgtctg agctgagaac    15600
cagtgacgtg aaggagggac tggtgggaag tttgggagga gtatcccgcc atgggagagg    15660
aacatgggtc ttgggactca gggctgctcg gggggcccga tgagactggg cagggctcct    15720
cagcaggcag cgttcagggc tcagtggggt ggggagatcc aggccctgcc tttccaatcc    15780
ccggccttcc cagaggggca tcctgcagag aagggcctgc cagggtaggg acggtgggtg    15840
gggtgtggtg gactgcggtg gtcccaaccc tatgccctgt gtccaccagg ctgctacccc    15900
cggtgcccca aggacaggcc catctatgag gaggatctga agaagtgtgt cactgcagac    15960
aagtgtggct gctatgtcga ggacacccac tacccacctg gagcatcggt tcccaccgag    16020
gagacctgca gtcctggta cctaagccca cgtggcaggg ggcctggggg agctgcacat     16080
atgggcacat gagtacacac acacgtgtga gcacacagtg tacacagtac acagacacac    16140
aaccgttcca catgggtgca catgcacaca aacgcacaca gcataccacg tgcatacaca    16200
cggtcacatg catgcatggt gcacacatgc acacatgaat ggatgccaac atgcaggcac    16260
acacagtcac acatgcacac agcgcacaca tggacacatg cctagacgca gatacccagg    16320
catacactca cggttacaca ctcacgcaca tatgcatgga tgcagacacg caggcacaca    16380
cggtcatata gtcatacacc acatgcacac atgcacagac acccaggcac acacagttac    16440
```

```
acagtcacac atgcacacat gcatggacgc agacacgcag gtgcacacac acatgcacag   16500
tgcacacatg tacacatgcc tagacacaga tacccaggca cacacagtca cacatgcatg   16560
gacacagagt cacatgtgta cacatacaca cgtgtggaca gacataggca cagtcacgtg   16620
cacacatgca ctcacactca gtcacacatg aacatgtgct cacatgcatg gacactgaca   16680
cgcaaggaca cacagtcaca catgcacaca tgcatagaca cagacaccca ggcacacaca   16740
gttacacagt cacacatgca tggatgcaga cacgcagtca cacagtcaca catgcacaca   16800
ctgcacacat gtacacatgc ctagacacag atatgcaggc acacacacat agtcaaacat   16860
gcacacatgc atggacacaa agtcacacgt gcacacatgc acacatgcat ggacagacac   16920
aggcacacac agtcacgtgc acagatgcac tcacagtcac acatgaacac atgctcacat   16980
gcacagacac tgacacgcag gcacacacag tcacacatgt acacgtgcct agacacagat   17040
acccagacac acacaattac acagtcgcac agtcacacat gcatggatgc agacacacag   17100
gtacacaagg tcacacagtc atataatgca cacatgcaca catgcataga tacagacacc   17160
caggtacaca ctcacggtga cacagtcaca catgcacaca tgcatggagg cagacacaca   17220
agcacacaca gtcacacagt cacacatgca cacaggagcc aggctacaga ggtaccagtc   17280
cctcactgcg gcggggggtc ttctgttctc atcccatcct ctgggtctgg ctttttcctt   17340
cctctcctcg cccctgctct gttcccacag ttacaaccca gtgggggggct cttccggagc   17400 tggctttggg gcagtgcctg ggggcttttgg gctcggtact agccacatgg ggaagctggg   17460
ggtctgagca gcgtgggcgc gttgtcagtg gagtgggact tgtagccatg tgcttgcttt   17520
gcagcgtgtg taccaactcc tcccaagtcg tctgcaggcc ggaggaaggt aagctgccct   17580
ctgctgccag ccctgcggtg gccgggccca tcctggggaa gcctgtgggg ccttggatcg   17640 gtgggggtg ctggtctcct cctgggctct gcccctttgg tccccccca gctcagaccc   17700 acctccgatg tgtatcagcc ctgggggct gctgtgaccc attttgtttc ttctggggtg   17760
tcggtgtcct gtgggggaatt tccgtcaccc tctcccgtga tccagcttct gcgttctgat   17820
gagattccct ttattcaaag agaggggctc tgggacgggt gcagtctcac tggagcatttt  17880 cttagctgct tgtgggggct cgggcacacc tggccttctt cctatcttgc tcctgatgag   17940
gtgattcttg gcctcaccct caccccccagg aaagattctt aaccagaccc aggatggcgc   18000
cttctgctac tgggagatct gtggcccaa cgggacggtg gagaagcact tcaacatctg   18060
ttccattacg acacgcccgt ccaccctgac caccttcacc accatcaccc tccccaccac   18120
ccccaccacc ttcaccacta ccaccaccac caccaccccg acctccagca caggtaaggc   18180
cccctggttc cctccatgct tcctcgggct ctcaccttcc cctgcatcca gcatccagca   18240
cagagggctc tttcggggc aggccccggc ctggtcagc caggctgtga cccctgcaca   18300
ccagctgcag agtgaggtga cagtggcatt cctctgcact gaggtgtgag ggggcctgcc   18360
ctggctcccc tggcctggtg cattgagata gtagcatcct gaccacatcc caagcccag   18420 accacagtgg aggatcacct ggggagattt ctgaaaacca gcaggaaact atccctaagg   18480
gttagagaaa ttttcttatg ttcccctgcg tttgttctgg ttgaaatcct agctaccact   18540
gaacaagcca ccaggggtat gatagccaca gaaaaagaa acttttttta aaaaggcaa   18600 gattttaaaa gatcttgaac tatataatga tatcctcttt tcttcctgct ttattgcagt   18660
tttatcaaca actccgagta agtgacggta atgatattca tgatgacaag cagggtggga   18720
ggagcgaagt cttataaaat cacctgcagg atgcttcctt cagggcccag atgtgaggct   18780
ggcggggctg gactcctctg cttatggacc aaagatggat gtattttggc cacttcattc   18840
```

```
atggtttgct gaggccaggg gctaaagtga gacctgattg gctgtcggtg acaatattgc   18900
tggttaagag tggagacaaa gcccttccg tcacacttcc ttactggaat gggaagctct    18960
cttgttattg attctttgaa aaaaagtat tgaaaatagc tgaggaaagg gtccatcaca    19020
cccaggtgtg ccctgggtg gccccgtctc tttgggctca ggttttcagt tgcaaaatga    19080
ggatggaagt ggtgtccagc cctgagctct ctggccctgc actctggttt tttggcaatg   19140
acagggaaaa gagagattgc agctggggga tggtcatgga ggtccctggg tcctctgaat   19200
cctggtggct tcctggaggt gcctctcccc aggtgtgaga gacaagaact tggttttgct   19260
tccctagagc tgtgctgcct ctggtctgac tggatcaatg aggaccaccc cagcagtggc   19320
agcgacgacg gtgaccgaga acatttgat ggggtctgcg gggcccctga ggacatcgag     19380
tgcaggtcgg tcaaggatcc ccacctcagc ttggagcagc taggccagaa ggtgcagtgt   19440
gatgtctctg ttgggttcat ttgcaagaat gaagaccagt ttggaaatgg accatttgga   19500
ctgtgttacg actacaagat acgtgtcaat tgttgctggc ccatggataa gtgtatcacc   19560
actcccagcc ctccaactac cactcccagc cctccaccaa ccagcacgac cacccttcca   19620
ccaaccacca cccccagccc tccaaccacc accacaacca cccctccacc aaccaccacc   19680
cccagccctc aataaccac cacgaccacc cctccaccaa ccaccactcc cagccctcca    19740
ataagcacca caaccacccc tccaccaacc accactccca gccctccaac caccactccc   19800
agccctccaa ccaccactcc cagccctcca caaccacca caaccacccc tccaccaacc   19860
accactccca gccctccaac gactacgccc atcactccac cagccagcac taccacccctt 19920
ccaccaacca ccactcccag ccctccaaca accaccacaa ccaccctcc accaaccacc   19980
actcccagtc ctccaacgac tacgcccatc actccaccaa ccagcactac taccccttcca  20040
ccaaccacca ctcccagccc tccaccaacc accacaacca ccctccacc aaccaccact    20100
cccagccctc aacaaccac cactcccagt cctccaacaa tcaccacaac caccctcca    20160
ccaaccacca ctcccagccc tccaacaacc accacgacca cccttccacc aaccaccact   20220
tccagccctc taacaactac tcctctacct ccatcaataa ctcctcctac attttcacca   20280
ttctcaacga caacccctac tacccatgc gtgcctctct gcaattggac tggctggctg    20340
gattctggaa aacccaactt tcacaaacca ggtggagaca cagaattgat tggagacgtc   20400
tgtgaccag gctgggcagc taacatctct tgcagagcca ccatgtatcc tgatgttccc    20460
attggacagc ttggacaaac agtggtgtgt gatgtctctg tggggctgat atgcaaaaat   20520
gaagaccaaa agccaggtgg ggtcatccct atggccttct gcctcaacta cgagatcaac   20580
gttcagtgct gtgagtgtgt cacccaaccc accaccatga caaccaccac cacagagaac   20640
ccaactccga caccaatcac caccaccact acggtgaccc caaccccaac acccaccagc   20700
acacagagta caaccaac acccatcacc accaccaata cggtaacccc aaccccaacc     20760
cccactggca cacagacccc aaccccgaca cccatcacca ccaccaccac tatggtgacc   20820
caacaccaa caatcaccag cacacagacc caaccccga cacccatcac caccactacg    20880
gtgaccccaa cccaacacc caccagcaca cagagaacaa caccgacatc catcaccacc   20940
accaccacgg tgacccccaac cccaacaccc accggcacac agaccccaac cacgacccc    21000
atcaccacca ccaccacggt gaccccaacc caacacccca ccggcacaca gaccccaaca   21060
acgaccccca tcaccaccac caccatggtg accccaaccc caacacccac tggaacacag   21120
acccaaaccc caacacccat caccaccacc actacggtga cccaaccccc tacacccacc   21180
```

```
ggcacacaga cccaacatc gacacccatc agcaccacca ctacggtgac cccaacacca   21240
acacccaccg gcacacagac cccaaccctg acacccatca ccaccaccac tacggtgacc   21300
ccaaccccaa cacccaccgg cacacagacc ccaaccacga cacccatcac caccaccact   21360
acggtgaccc caaccccaac acccaccggc acaaagagta caaccccgac atccatcacc   21420
accaccacta tggtgacccc aacccacca cccactggca cacagacccc aaccacgaca   21480
cccatcacca ccaccactac ggtgacccca accccaacac ccaccggcac acagacccca   21540
accccgacac ccatcaccac caccaccacg gtgacccca cccaacacc caccggcaca   21600
cagaccccaa catcgacacc catcaccacc aacactacgg tgaccccaac cccaacacca   21660
accggcacac cgagtacaac cctgacaccc atcaccacca ccactatggt gaccccaacc   21720
ccaacaccca ccggcacaca gaccccaaca tcgacaccca tcagcaccac cactacggtg   21780
accccaacct caacacccac cggcacacag accccaaccc cgacacccat ctccaccacc   21840
actacggtga ccccaacccc gacacccatc tccaccacca ctacagtgac cccaacccca   21900
acacccaccg gcacacagac cccaaccatg acacccatca ccaccaccac acggtgacc   21960
ccaaccccaa cacccaccgg cacacagacc ccaacaacga cacccatcag caccaccacc   22020
acagtgaccc caaccccaac acccaccggc acacagaccc caacatcgac acccatcacc   22080
accaccacta cggtgacccc aaccccaaca cccaccggca cacagacccc aaccacgaca   22140
cccatcacca ccaccacac ggtgacccca accccaacac ccaccggcac acagagtaca   22200
accctgacac ccatcaccac caccaccacg gtgacaccaa cccaacacc caccggcaca   22260
cagaccccaa ccccgacacc catctccacc accactacgg tgaccccaac cccaacaccc   22320
accggcacac agaccccaac cacgacaccc atcaccacca ccaccaccggt gaccccaacc   22380
ccaacaccca ccggcacaca gaccccaaca acgacaccca tcagcaccac caccacggtg   22440
accccaaccc caacacccac cggcacacag accccaacat cgacacccat caccaccacc   22500
actacggtga ccccaacccc aacacccacc ggcacacaga cccaaccac gacacccatc   22560
accaccacca ccacggtgac cccaacccca acacccactg gcacacaggc cccaacccca   22620
acagccatca ccaccaccac tacggtgacc ccaaccccaa cacccaccgg cacacagacc   22680
ccaacaacga cacccatcac caccaccacc atggtgaccc caaccccaac acccaccggc   22740
acacagaccc caacatcgac acccatcacc accaccacta cggtgacccc aaccccaaca   22800
cccaccggca cacagacccc aacccgaca cccatctcca ccaccactac ggtgacccca   22860
accccaacac ccaccggcac acagacccca accatgacac ccatcaccac caccaccacg   22920
gtgacccaa ccccaacacc caccggcaca cagaccccaa caacgacacc catcagcacc   22980
accaccacgg tgaccccaac cccaacaccc accggcacac agaccccaac atcgacaccc   23040
atcaccacca ccactacggt gaccccaacc ccaacaccca ccggcacaca gaccccaacc   23100
ccgacaccca tcaccaccac caccggtg ccccaacccc aacacccacc ggcacacag   23160
accccaacat cgacacccat caccaccacc actacggtga ccccaacccc aacacccacc   23220
ggcacacaga ccccaaccac gacacccatc accaccacca ccggtgac cccaaccca   23280
acacccaccg gcacacagag tacaaccctg acacccatca ccaccaccac acggtgaac   23340
accaaccccc aacacccacc ggcacacaaa accccaacat caacacccat caccacccac   23400
cactacggtt gaccccaacc cccaaaaccc accggcacac agaccccaac cccaacacccc   23460
attctccacc accaataacg ggtgaccca accccaacaa cccaccggca cacagacccc   23520
aaccatgaca cccatcacca ccaccaccac ggtgaccca accccaacac caccggcac   23580
```

| | | | | |
|---|---|---|---|---|
| acagacccca | acatcgacac | ccatcaccac | caccactacg | gtgacccccaa ccccaacacc | 23640 |
| caccggcaca | cagaccccaa | ccatgacacc | catcaccacc | accaccacgg tgaccccaac | 23700 |
| cccaacaccc | actggcacac | aggccccaac | cccaacagcc | atcaccacca ccactacggt | 23760 |
| gaccccaacc | ccaacaccca | ccggcacaca | gaccccaacc | acgacaccca tcaccaccac | 23820 |
| caccacggtg | accccaaccc | caacacccac | cggcacacag | agtacaaccc tgacacccat | 23880 |
| caccaccacc | accacggtga | caccaacccc | aacacccacc | ggcacacaga ccccaacccc | 23940 |
| gacacccatc | tccaccacca | ctacggtgac | cccaacccca | acacccaccg gcacacagac | 24000 |
| cccaaccatg | acacccatca | ccaccaccac | acggtgaccc | caaccccaa cacccaccgg | 24060 |
| cacacagacc | ccaacaacga | cacccatcag | caccaccacc | acggtgaccc caaccccaac | 24120 |
| acccaccggc | acacagaccc | caacatcgac | acccatcacc | accaccacta cggtgacccc | 24180 |
| aaccccaaca | cccaccggca | cacagacccc | aaccacgaca | cccatcacca ccaccaccac | 24240 |
| ggtgacccca | accccaacac | ccactggcac | acaggcccca | accccaacag ccatcaccac | 24300 |
| caccagtacg | gtgaccccaa | ccccaacacc | caccggcaca | cagaccccaa ccacgacacc | 24360 |
| catcaccacc | accactacgg | tgacaccaac | cccaacaccc | accggcacac agtccccaac | 24420 |
| cccaacagcc | atcaccacca | ccactacggt | gaccccaacc | caacaccca ccggcacaca | 24480 |
| gaccccaaca | ttgacgccca | tcaccaccac | cactacggtg | accccaaccc caacacccac | 24540 |
| cggcacacag | accccaaccc | cgacacccat | ctccaccacc | actacggtga ccccaaccc | 24600 |
| aacacccacc | ggcacacaga | ccccaaccac | gacacccatc | accaccacca cacggtgac | 24660 |
| cccaaccccg | acacccaccg | gcacacagac | cccaaccacg | gtactcatca ccaccaccac | 24720 |
| tacgatgacc | ccaaccccaa | cacccaccag | cacaaagagt | acaaccgtga cacccatcac | 24780 |
| caccacaact | acggtgaccg | caaccccaac | acccaccggc | acacagaccc caaccatgat | 24840 |
| acccatcagc | accaccacta | cggtgacccc | aaccccaaca | cccaccactg gaagcacggg | 24900 |
| gcccccacc | cacacaagca | cagcaccgat | tgctgagttg | accacatcca atcctccgcc | 24960 |
| tgagtcctca | accctcaga | cctctcggtc | cacctcttcc | cctctcacgg agtcaaccac | 25020 |
| ccttctgagt | accctaccac | ctgccattga | gatgaccagc | acggcccac cctccacacc | 25080 |
| cacggcaccc | acgaccacga | gcggaggcca | cacactgtct | ccaccgccca gcaccaccac | 25140 |
| gtcccctcca | ggtaagcaga | gccgcttggt | tcctctggcc | tgggatgctt cttcctcccc | 25200 |
| ttgtgccggg | caggactgtc | ccaggaaggc | tcaaggcacg | ttctgggcgc ctctctgccc | 25260 |
| acgaagcttg | gtcactgtgt | gggcagaagc | cactgacact | ggccagtgct gggcagtgaa | 25320 |
| gccaaaggcc | attccgcttg | cccataggac | agccttctga | ggagctgctg acaccggcca | 25380 |
| gtgctgggca | gtggagccct | tggctatcct | gctcgcccat | aagacggcct tcttcagggg | 25440 |
| cccactgcta | tgtgatgcgg | tgctgtggga | gcccatcaag | gctgggggc agagagaggc | 25500 |
| tgccagtgag | gtgcctgcgg | gtccacctgc | ttctggctgc | agcccctcct tggggccttt | 25560 |
| tcctggtgga | cggcatgcca | cagccagtgc | cttctggacg | cctcttgctg gccatcggct | 25620 |
| tggccagcaa | gctgtgttgc | tgccagagca | ccaggtcacc | tgcaggctct cgtgacactc | 25680 |
| ggctgtggtg | atactggcct | tgccgctcca | ccctgcctgg | tgactctgag agcctgggag | 25740 |
| gtgggcacga | ggccctggtc | ctccagttct | gccaccggt | cggctgtctg gctcccttgc | 25800 |
| agctggggag | tggcagttgg | gacctgtgg | catctgagat | gtgcaacgtc tcagccctca | 25860 |
| ctggtgtctc | ctgctctcac | aggcacccc | actcgcggta | ccacgactgg gtcatcttca | 25920 |

```
gcccccaccc ccagcactgt gcagacgacc accaccagtg cctggacccc cacgccgacc    25980
ccactctcca cacccagcat catcaggacc acaggcctga ggccctaccc ttcctctgtg    26040
cttatctgct gtgtcctgaa cgacacctac tacgcaccag gtactcaggc tgttcacatc    26100
ctgtgcttgg gtggccgagg ctggcccegg catgtaccaa tgggtcaggt gccagggctg    26160
agatcgcagt agaagcgtct caggaggcag cagccgtcga gggtggctgt gtccagggca    26220
cggcttccct tgggtggcct ctgtggggac ctccgctgtg ggacctcca cggggtccag     26280 cggctagccc tgcctccggc tagccctgcc tctggacggt gtgatcgtgg gtctgtctcc    26340
cttcgcaggt gaggaggtgt acaacggcac atacggagac acctgttatt cgtcaactg     26400 ctcactgagc tgtacgttgg agttctataa ctggtcctgc ccatccacgc cctccccaac    26460
acccacgccc tccaagtcga cgcccacgcc ttccaagcca tcgtccacgc cctccaagcc    26520
gacgcccggc accaagcccc ccgagtgccc agactttgat cctcccagac aggtcagtgg    26580
gctgcaggcg gctttgtccc catggcactc tgcgcagcat gtccgggcag ctgaggcccc    26640
aggcaccact tcctgctggt cgtctgaggg ccgaggcctc cagcaaccct tgggtgcagg    26700
gtctgccgag ccctccacat tttcaccgtg ccccgctgtg cctggcgagg tggctggctg    26760
cagtgaggtc cgtggaagcc acttcggcct ccagcctccc ggctcagcac ccgcccctcc    26820
tgagcgcaga ccaccccatc ctgtgccggt cccctgacg tcccttgcct cccgtcccca     26880
ggagaacgag acttggtggc tgtgcgactg cttcatggcc acgtgcaagt acaacaacac    26940
ggtggagatc gtgaaggtgg agtgtgagcc gccgcccatg cccacctgct ccaacggcct    27000
ccaacccgtg cgcgtcgagg accccgacgg ctgctgctgg cactgggagt gcgactgtga    27060 gtccgggggcc cccaggccct ccccgcatct cctgccctct ccgtgggtgg gggctgcagg    27120
gcccgtctcc cggggggcgga agggctgagg ctccttgggc acagatccca ctgaggtgtt    27180
cgctgaggct gggtgacttc tgagggtctt ctcacagccc tgcttttgcc tcattgggtg    27240
gggagggcct gggcaggtgg agggcttgcc tggtggagtt agggctcctc cctgaacaa     27300 gggtgcttct gaggcaagag ggggctgagt tgaagtttga accctggtcc gtcctgcaga    27360
atgggccact gtgggtgcgc cagggcaagt gcagctcaga catccccgtg cccacgcaca    27420 ggagtgggggt tttcaggccc cagcttcctg ctggctcttc ctgactatgc cccagcccag    27480
cccttgcacc cgaccccggc cgaggggcac aggtggcacg gctcactccg gctcccttgc    27540
aggctactgc acgggctggg gcgacccgca ctatgtcacc ttcgacggac tctactacag    27600
ctaccagggc aactgcacct acgtgctggt ggaggagatc agcccctccg tggacaactt    27660
cggagtttac atcgacaact accactgcga tcccaacgac aaggtgtcct gccccgcac     27720 cctcatcgtg cgccacgaga cccaggaggt gctgatcaag accgtgcata tgatgcccat    27780
gcaggtgcag gtaggcacag cgtggccaca ggaggctggc atggaggcgg gtgctgacat    27840 gggcccccaat gcaccctggt tccccagggg ccagaggact gggctgtggg ggtgccaagg    27900
catagcctct cctagagttg ggctagaagg taggatgggg tgggcgactg gctccgggac    27960
atatcagctc ttcctgcagg ccctccaggt gtgtcctggg ccctcgagc cctggcacca     28020 tgccacgctg gcacagtct ctgcagcaga agctgcctcc tgaggacaga gtcagggaca     28080
gggctctgca caccccttggc tgagatgccc ctacttgcag gggaatcatt ggttctgagg    28140
ctcaggaggc cccgggagcc tgcgccggc tccacagtcc caggtgctc ccaggagagc      28200 tccttcactg gctcacccat gggaccaggg tctggttggg agcagtggag tggaagcaag    28260
aaagggggca ggaaagcggg gtaggcaggg ccctctccct acatgtgtag gtcagagagc    28320
```

-continued

```
aggcggggtg gggcagccct ggagctctca caaggagagg accgaggcag ctgcagctcc    28380
catggtgtgt cggccacagg tgcaggtgaa caggcaggcg gtggcactgc cctacaagaa    28440
gtacgggctg gaggtgtacc agtctggcat caactacgtg gtggacatcc ccgagctggg    28500
tgtcctcgtc tcctacaatg gcctgtcctt ctccgtcagg ctgccctacc accggtttgg    28560
caacaacacc aagggccagt gtggtgagtt ccgtgacccc catggccccc gaggccccca    28620
cggctcccac cgtcccctgt gcccccatgt cctgccccag gcgggtggc caggccaggc    28680
tgaggctgag gctgcgtgta aacacccatg ggcctggctg tgggcctctt gccccgctgc    28740
tcggggctgt tgtggccatc acccgggttc agtctctgtg aggagccaac aggagggggc    28800
ctggcctggt ctctgccctc ggccctggct ggccggtcct gggcatctgg gctggagaag    28860
ggcagggctt accctgtctg caacgtggcc tctctcactg atacaggcac ctgcaccaac    28920
accacctccg acgactgcat tctgcccagc ggggagatcg tctccaactg tgaggctgcg    28980
gctgaccagt ggctggtgaa cgaccccctcc aagccacact gccccacag cagctccacg    29040
accaagcgcc cggccgtcac tgtgcccggg ggcggtaaaa cgaccccaca caaggactgc    29100
accccatctc ccctctgcca gctcatcaag gacaggtgac cccgcccagg cctgcctgtg    29160
gccacgacac caataagctg agggcctctg tgccccagcc cccagctctt gcaaagagga    29220
aggaggcagc gcgtggggcc tggcgctggg gctgggaagg cacggagccg cggaaccagg    29280
atcaggcgct aggtcgccgt ggggtccagg acccaggccc ttgggttcca cggggctgag    29340
ctgctacgtg cggcctgtgc ctttgctgaa ctccagtctc tcctggctcc cgggaaggtg    29400
cagggctggc cgagtgtgag gcccggagta aaccagtcaa cccaggacag agctcagggc    29460
tgatattggg agggcagatt tgggctttga cagagagggg gtgctcctaa cgctggcagt    29520
catgggggt cagcatcctg tccctggaag tatagggggcc aggtataggc tgggtgtcca    29580
tctgccaggg ttgctggagg gggtcctgaa gctgatgacc acatagacgt ggtttctatc    29640
tctgggagcc gggctgcaga gccaccttgc tcggccatcc cttggtctgt ccctgagctg    29700
tccccctggc tggcctgtcc cttgaccctc catcagccac aggcgcctct ctggcgggtg    29760
ccggactcca ggaggacagt ccgggcagag acgctggggt agagagcagg ggagaggcag    29820
gtgccacctg agtgtgacct gtgcctctcc ctgcgcagcc tgtttgccca gtgccacgca    29880
ctggtgcccc cgcagcacta ctacgatgcc tgcgtgttcg acagctgctt catgccgggc    29940
tcgagcctgg agtgcgccag tctgcaggcc tacgcagccc tctgtgccca gcagaacatc    30000
tgcctcgact ggcggaacca cacgcatggg gcctgctgta agtgcccatc tgcccctgcc    30060
ctggagctgg gggcctgcag gccagacgtg gtctctaggc tctgccaggt gctgtgccca    30120
gcctgaagct agacctagat gggctgcggc cagggacgca gagatggcgg gtgtgagacc    30180
agggctgggg ccatggggtg gggaaggcca ggctggaggg gctgaggtgc tggggcttct    30240
gccagcatcg ctaaatgcaa ctgggtgccc accaccagc tcgggacaac ctcgagggtg    30300
gaggttgatg cccaggcagc tggtcaccct cctccgtgtg tggggcactg gcagctgtc    30360
actcaagggg gtccaggctc ctccgcctga catgaggcag ccctctgacc tctgcccatg    30420
tccctcagtg gtggagtgcc catctcacag ggagtaccag gcctgtggcc ctgcagaaga    30480
gcccacgtgc aaatccaggt atgttgtttg agggtccacc aggaccgtgg gctcgccttc    30540
tgcagtgcgg agggtggcat catctgggca tagcagtccc acctgccagc tcccagccc    30600
caccccacct gtctgacaat gccctcccgc ccccagctcc tcccagcaga acaacacagt    30660
```

| | |
|---|---|
| cctggtggaa ggctgcttct gtcctgaggg caccatgaac tacgctcctg gctttgatgt | 30720 |
| ctgcgtgaag acctgcggta cgccacccac tcacactgtc ccctcctgcc tccctcctgc | 30780 |
| ctcctcctgg gtgtccacgg aggctgggac caggacgctg accaccccc acctctgatc | 30840 |
| cctgttgcac aaggactctg ctaacacaac ttgtctcctg ggtgtccatg gaggctggga | 30900 |
| ccaggaggct gaccaccccc acccctgctc cctgctgcac aaggactctg ctaacacaac | 30960 |
| ttgtttcttc cctcttccta ggctgtgtgg gacctgacaa tgtgcccaga gaggtaggcc | 31020 |
| ccaccgtgtt gctgggggat ccttccacaa attctgaatt ctggggagtg agggatggac | 31080 |
| atgaaaacct ggagcctcaa agattgagga atgaggtcat ctaagtcctg gatggctgag | 31140 |
| ttggcatgga caccacccac tcacccaccc atccttccac ccacccactc atccacctgt | 31200 |
| gcacccatct acccactcac ctaccctcc atccttccac ctaccagtc atcccccact | 31260 |
| catctatgca cccccccacc cacccactca tccatccatc catccaccat ccacctaccc | 31320 |
| aaccatccac ccatccatcc accatccatc taccatccac catccaccca accatccacc | 31380 |
| atccatccat ccacccatca tccatctacc atccacccac ccacctatcc atccatccat | 31440 |
| ccaccatctg tctaccatcc acccacccac tcatccatcc atccatccac catctgtcta | 31500 |
| ccatccaccc acccacctat ccatccaccc atccatccat ccatccatcc atccatccat | 31560 |
| ccatccatcc acccaccatc tgtctaccat ccacccaccc acctatccac ccatccaccc | 31620 |
| acccatccat ccacccaacc atccaccatc catccatcca tccatccatc caccatccat | 31680 |
| ctaccatcca ccctcccatc catccacgca tccacccaac catccatcca tccatccacc | 31740 |
| atccaccac catccacccca tttatccatc cattctccct ccctccattc accacccatt | 31800 |
| ggtcatatga tactctgtct agaagctctg acatgacatc ttggccacct ctgtgctgcc | 31860 |
| catgcctcct acctgtggta gcagccatgt ggatgattcc ttagctaaat tctgtacaaa | 31920 |
| cctgagaggc ctgagtggag aatttgccac gtgccaagcc cctgcttgtc gatgctggtg | 31980 |
| agcaggtaat ggctttgtga tatcagtgaa tgagcagcta ctgtcctatc ccagaacctg | 32040 |
| cctggtgtgc tcagaagtga ggagggacat ggttttcccc caggatccct cagcactctg | 32100 |
| ctcagggtgt ctgtttctcc ccgctgacca cagctgcagc tccggggctg tggtgaggtg | 32160 |
| gggcctgcct ggtgccacct gtcctctcta ctcacccttc tttccctgca gtttggggag | 32220 |
| cacttcgagt tcgactgcaa gaactgtgtc tgcctggagg gtggaagtgg catcatctgc | 32280 |
| caacccaaga ggtgcagcca gaagcccgtt acccactgcg tggaagacgg cacctacctc | 32340 |
| gccacggagg tcaaccctgc cgacacctgc tgcaacatta ccgtctgcag taaggccatc | 32400 |
| ccctgggggcc catgccacct ctcaggggtg cacacatccc tgtaggctgg gctgcctgct | 32460 |
| gtcccctcct tggcaagtga ggaaacagct ggcttggggg cctctgctgt gcccttgag | 32520 |
| agggcttggg aggggccgc tgggcccagt ccaggcatcc ctgctgcagg gcctgacctg | 32580 |
| ggtggggagg gaccccttgg aggtgctgga ggcccgaccc tgtgcagtgg ccccggggc | 32640 |
| tttgcctggg aggagccacc ctcacggccg cgtgcgcacc ctgtcttcag agtgcaacac | 32700 |
| cagcctgtgc agtggccccg ggggcttggc ctgggaggag ccaccctcac ggccgcgtgc | 32760 |
| acaccctgtc ttcagagtgc aacaccagcc tgtgcaaaga gaagcccctcc gtgtgcccgc | 32820 |
| tgggattcga agtgaagagc aagatggtgc ctggaaggtg ctgtcctttc tactggtgtg | 32880 |
| gtaagcaggg ctggtgggca gggcaggag gaggctgccg cccggggtgg ggtggctgta | 32940 |
| aggggggttgg ctccctcctg ggggtctcag attctgggga cacagatggc tgtacgcttg | 33000 |
| gctgatgcac ccaccccagc cctgagcgct cgctccatcc actgggtgtg caccgggagt | 33060 |

```
gggggtctgg ccaggtggcc gccccggggc agtctccaac gaacggcctt ctccgttctt   33120
tctcccaaga gtccaagggg gtgtgtgttc acgggaatgc tgagtaccag gtgagccctg   33180
ggctgggtga gagggaggag gggaggaggt cggctgcagc gtggggggtcc tggcaggctg   33240 ttgggctggc tgggatgctg gagaggcccc tgcctcatgt ctctccctgt gcccgaagcc   33300
cggttctcca gtttattcct ccaagtgcca ggactgcgtg tgcacggaca aggtggacaa   33360
caacaccctg ctcaacgtca tcgcctgcac ccacgtgccc tgcaacacct cctgcagccc   33420
tgtaagcggc caccctcctc cttcagcctg ccctttttccc tcctcccaga caagcacccg   33480
ggcccatgtc tgcatcgtga ccctttcttt cctccttttca acgccaacct gtccctgtcc   33540
ccacctctcc atcctgacac ctgcccagcc tggggcctcc tccaggtggg ggggtctcgg   33600
cagccctgca ggctttgtgt ggtgtggggt acagcctggg agttcagttg cagtggcgtg   33660
tctatgtgcg cagggcttcg aactcatgga ggcccccggg gagtgctgta agaagtgtga   33720
acagacgcac tgtatcatca aacgcccga caaccagcac gtcatcctga aggtaggtgt   33780
gcactgccgg ccccgacgcg gccgggttgc ttgagcccag ggcaaggcgc gggccaccca   33840
ggatccccca gctgagtcct cccagtcctg ggcgcagctg tgatgggcgc cctggggctg   33900
ccatgacaaa tgagcaggcg tcttcagggc agaaagggat tctcctggtt ctgcggccca   33960
gaaatccata gagcaaaggg cctcaggggct gtgctccctc ggaggcgcta ggcaaggacc   34020
tttcccagcc tctggtcact ctaggtgccc cttggctgtg accacgaggt ttccttccct   34080
gtgtctgcct ctcctctccc ttttaaggat ttaggcaccc caagcaggat gatctcatct   34140
taggatcctt cacttaatga caccttcaaa gacccctttt ccaaggcagg tcacattcat   34200
agattcagag ttagaacaca gacagaccct tgagggttgt gtgggctcca ggctggtgcc   34260
tgatgtgggg ccccgcccat gtcacttgtc ctgtggccct gggcctcacc aggaagcctc   34320
cccggccagg tgtctccagg gtgtcttcct ggccgggctg gggctgggcc tgctgccctc   34380
cctcaccaga gctccctgcc ccacagcccg gggacttcaa gagcgacccg aagaacaact   34440
gcacattctt cagctgcgtg aagatccaca accagctcat ctcgtccgtc tccaacatca   34500
cctgccccaa ctttgatgcc agcatttgca tcccggtgag ttggccacct ggggcctggc   34560
tgtgtgtact ctgccgggag tgggggtgcc tggtgttctg gggggctggg gccccagtgc   34620
tgcgacagtg acctcgggcc tggtctgagc tgccgcagga ggctttgcct ggggcttttct   34680 gcagcagcta cccccgccca cggcatcgtg ggaaggtgct ctcatcccca ggaatgtccg   34740
ggggtcccgg gctcattctc ctttccctct agggctccat cacattcatg cccaatggat   34800
gctgcaagac ctgtgagtac agggcacagc ctgggggggta ggcagggtgg gggcacaagg   34860
gctggtgccc tcagccccgc ctgggtggc tggaggctgg acaacggcct tgggtgggc   34920 agtgagggct gggggctgag gccgagcctg ggagggggac gcagcgaggg agagcctcct   34980
cgaagatgtg gaggccctgc cctaagccgc tgcccgctct ccccaggcac ccctcgcaat   35040
gagaccaggg tgccctgctc caccgtcccc gtcaccacgg aggtttcgta cgccggctgc   35100
accaagaccg tcctcatgaa tcattgctcc gggtcctgcg ggacatttgt catgtgagtc   35160
ccaggctggg agtgtgcctg gaggggtgg tggagacccc agggaggcga gaggccagcg   35220
ctggccccgg aagtcacccc ctcactccgc cctccccca ggtactcggc caaggcccag   35280
gccctggacc acagctgctc ctgctgcaaa gaggagaaaa ccagccagcg tgaggtggtc   35340
ctgagctgcc ccaatggcgg ctcgctgaca cacacctaca cccacatcga gagctgccag   35400
```

```
tgccaggaca ccgtctgcgg gctccccacc ggcacctccc gccgggcccg gcgctcccct    35460
aggcatctgg ggagcgggtg agcggggtgg gcacagcccc cttcactgcc ctcgacagct    35520
ttacctcccc cggaccctct gagcctccta agctcggctt cctctcttca gatatttatt    35580
gtctgagtct tgttcagtc cttgctttcc aataataaac tcaggggac atgc            35634

<210> SEQ ID NO 31
<211> LENGTH: 21849
<212> TYPE: DNA
<213> ORGANISM: Homo sapiens
<220> FEATURE:
<223> OTHER INFORMATION: CEACAM5

<400> SEQUENCE: 31
gatgctgaga agtactcctg ccctaggaag agactcaggg cagagggagg aaggacagca      60
gaccagacag tcacagcagc cttgacaaaa cgttcctgga actcaagctc ttctccacag     120
aggaggacag agcagacagc agagaccatg gagtctccct cggcccctcc ccacagatgg     180
tgcatcccct ggcagaggct cctgctcaca ggtgaaggga ggacaacctg ggagagggtg     240
ggaggaggga gctggggtct cctgggtagg acagggctgt gagacggaca gagggctcct    300
gttggagcct gaatagggaa gaggacatca gagagggaca ggagtcacac cagaaaaatc     360
aaattgaact ggaattggaa aggggcagga aaacctcaag agttctattt tcctagttaa     420
ttgtcactgg ccactacgtt tttaaaaatc ataataactg catcagatga cacttttaaat    480 aaaaacataa ccagggcatg aaacactgtc ctcatccgcc taccgcggac attggaaaat     540
aagccccagg ctgtggaggg ccctgggaac cctcatgaac tcatccacag gaatctgcag     600
cctgtcccag gcactggggt gcaaccaaga tcacacaaat ccctgccctc atgaagctca     660
tgctctcatg ggaggaaga cagacataca aagagatcta gaatgtgagg tcaggtgttg     720
acaagagccc tggagggaat agagcaggga aaggtcagaa aaggaagacc cagggtctct     780
agaggaggtg tcaggaagg gatctcccaa gaatgccctg atgtgagcag gacctgaagg     840
caatggggag ggagccgtga agacccctgg aaaagcagat tccacacagg gaaatgccaa     900
ggtcagaggt gctaaggaaa taggagacac actgctgacc ttgacctagt aggacacaca     960
cacacacaca cacacacaca cactcactca ctccagggct gggggatgaa gagacctgct    1020
caggacccag gaccccattt ttccacccta atgcataggt cccaatattg accgatgctc    1080
tctgctctct cctagcctca cttctaacct tctggaaccc gcccaccact gccaagctca    1140
ctattgaatc cacgccgttc aatgtcgcag aggggaagga ggtgcttcta cttgtccaca    1200
atctgcccca gcatctttt ggctacagct ggtacaaagg tgaaagagtg gatggcaacc    1260
gtcaaattat aggatatgta ataggaactc aacaagctac cccagggccc gcatacagtg    1320
gtcgagagat aatatacccc aatgcatccc tgctgatcca gaacatcatc cagaatgaca    1380
caggattcta caccctacac gtcataaagt cagatcttgt gaatgaagaa gcaactggcc    1440
agttccgggt ataccgtgag tgattccccc atgacctctg ggtgttgggg gtcagttcta    1500
cttcccacac acaggattat caggcctggg ctgtgcctgt ggccccctct gcattacgca    1560
ccatgttagg gtttgggcat ttagtgcagg atacacacag aagagacaaa cttcaacaga    1620
tcagaattcc tttccggcat ccagaccctg cagacactca ctgcagagga aggacagtct    1680
gatgtggggg acttagcagg gggaggtcag tctcagccaa gcaccccgtg ccctccccgt    1740
aaacctgacc ctgagaaaga ccctggagaa ctgcatcaga gcctggcctg agggacccct    1800
gggatattca cagagaagct cagcccccagg gctcctggtt ccaggtgact caggggagcc    1860
```

```
tgtgccaggg ctgtgttgtg gcctcctggg caaggctaac tggaagcaag gacttagcag    1920
ctgtccaagg gctgtggctc ctggagctgg attctggatg cagaatcgga ctttctggcc    1980
acacttgttc cctgtcccca gagtctcatt tggacaagga cagagccttg tcctttactt    2040
gagactcaat gtggggagga tagatagaca aggttattag ggtgtcagtc cattgccctg    2100
gggacatagg tgactccatg ggaagctcag tgtccccagg aagaggaaca gaggagagaa    2160
gatgctcccg gcagctcctt gtccaccagg gatcaggccc agggccttct ctcttggagg    2220
caaataaaca taaatgatgt tcatttgagc agctcctctg tgcagagctg agatcaagta    2280
attgtaaata ttttgaggtt aattcacaaa caacctcaca gccaaatagc acttatccta    2340
cttattgaaa ggaaattgag gcacagggag acagtcacta acaagggtca cacaggccat    2400
aggtgtcaga ttgaagtcac atgaggtctg tctgtagcca cagcccctc ctctcctcaa     2460 ctgggggtgg gtggggctgt tgttgttag gcatctgcat ctgagaccag tcatgggctt     2520
gcgttctttt gtcttgggca tccacagctc agaagcggag attctggtct ggagagtgat    2580
aagtaaatgg agaaataatc agttttactc tagaactaga tcacctcaac agtcagggtc    2640
agtgccggga ttgtccaggc ctctccctga gatccacagc cccctcacat gacctcaaat    2700
cctgtgtttc ccgatgtgtc agtgtcactc ccacggaagg ataaaggaaa ggacttcgct    2760
ttctctcccc actcacaccc tgtgccaaca gaggcccaaa gtgagacaca cgcttgctca    2820
gtagctctct catgaagggg ggaatgagtg aaggaatgat ccataacctc tatagagact    2880
ggatcctgga tgcagaatcc tgggaggttc tgaccacacc tgttccgtgt ccatcagggg    2940
ctgagatcca tgtaccattc ctctgacccc ctgtcccgaa agccacccta tctcatgtga    3000
ctctggggtt ccttggccat gggagggttt tcaaggctcc ctggtcctgg tcgggacagc    3060
caagggactc ctagtcctgg ggtctccgag gtcactatac cccgcatggc tcattgccat    3120
gggcatttct gactttcttc tattcctcca tgttcttcgt cttcctccct cttcattcca    3180
gctgagatgc ccatccctga acatcttcct ccactcttag gccttcccca gacactccct    3240
tgaacaaggc tggctgtcct gtttttcttgc cgctcacact gtgtcctggc ccacttccca    3300
ggcaataggg aaggcacaga atcacaggc aataggaag gcacagatgg agccctgcc      3360 aggctccatc acaagccaat gtcaacaggt caccaggaga atgagcttcc gctgtgttcc    3420
tgcccagggc tctttacttc catgaggcca acacacggaa caggcagcag gacgggaatg    3480
agcgactcct ccatccactc cctacactga ctcaccaggg ggtcagaggc agaaggacag    3540
gtctgcagtc cccaaagccc gcatgcttat ttcactcact tcactaccca ctccatcttc    3600
atcctggtgt ggggctcaca tcctccagtg gatcctggga cctcccccag gtggagctgg    3660
ccaggcaggt gctgtctgat aggtttgctg cccattccac atacacctgt gtcctcatga    3720
tgatgccatt gtcataaggt ggagtccctt ggactgagaa gtgaaccagc cactggcgtc    3780
tcacttagac tctacccagt tacaaaaact taaactctag ttgtgttttc tgaggttgat    3840
aggagaggaa gaaaaccttt cacatgcctg ttttgaggct tctcctcttt ttgcctaact    3900
ctgcacagga actaggggca gggagcgctt tctaaattta ctaacatcac acacattgct    3960
tctcctaact tggcatcatt tctccctta tgtaattgac acacctaaga gttcctctct     4020
gaccggttct gtcctcttaa caggtctcac atccctctct ctgttcaggg agtcactgat    4080
ttcaaaccac tttcagcatc ttcctttgag cataatgtga tcactttgga attcagagca    4140
gacctaaacc ttagcataat attaaaagaa gtactacttc cagcaattga tcttagatct    4200
```

```
ttaggccatt gataagaatt tccacttatg gaaaaattt  aatgtttccc ccaaatgtct    4260 ttcactttt  taactatagt cagaaaataa catgagatct aaactcctga caaattttta    4320
agggcaaatt atagtactac agattgagta tcccaaatcc taaaatccaa aatctgaaat    4380
gctccaaaat ccaacatttt ttgaccactg acatgattct caaagaaat  gctcactgaa    4440 ggccgggcac ggtggctcat gcctgtaatc ccagcacttc gggaggccaa ggcgggaaga    4500
tcacaaagtc aagagatcaa gaccatcctg gccaacatgg tgaaacccg  tctctactaa    4560 aaatacaaaa attagctggg cgtggtggca tgcacctaca gtctcagcta ctttggaggc    4620
tgaggcagga gaatcgcttg aacccgggag gtggaggttg cagtgagctg agatcgtgcc    4680
actgcactcc agcctggcaa cagagcgaga ctccatctca aaaaaagaa  aagaaagaa    4740 aagaaaagaa aaagaaagg  ctcactggag cactttggat tccgtatttt cagatttggg    4800
gtgctaaact ggtaagtata ttgcaaatat tcaaaactca aaacagtca  gaaatccaaa    4860 acactttag  tcctaagcct tacacataag acatactcaa tctgtatgaa ctataggcac    4920
caagctgaac agcagatccc tagaacctcc tcatcctgca taactgaaac tgcagaccca    4980
tgaacaactc tccattcccc cagttcccag gctttgacaa ccaccattct actctctgat    5040
tccacaagtg tgactactct agggacttca tataagtgga atcctacagt atctgccctg    5100
tgagtggctt atttcattta gcataatgtc caatgggaga aaataattgc aaaacttctt    5160
ctcaaagttc tgtctcataa ctgtcaaaca cacatggtcc ttgagggcca gatttccagc    5220
agttcatgct ccccctttc  caccagtcag ttctgcatt  gcaaatgtcc acatgtattt    5280
atggagagat ccacagcatc ctcgcctgcc ctctgcaagg ggagaaggga cattaaagac    5340
caaagacagg ccgggtgcag tggctcatgc ttgtaatccc agcactttgg gaggccaagg    5400
tgggcagaac acctgaggtc agaagttcaa gaccagcctg accatatgg  tgaaaccca    5460 tctctactaa aaatacaaaa tttagctggg tgtggtggtg ggcgcctgta gtcccagcta    5520
ctcgggaggc tgagacagga gaatcgcttg aacccgggag gcagaggttg ccatgagccg    5580
agatcgtgcc tggccaacac agcaagactc catctcaaaa aacaaacaaa caaacaaaga    5640
ccaaagacaa agaacataca tatggttctg ctgttaaatc cgggcagctc ctgcctgtca    5700
cctgaagttc tagatcattc cctggactcc actctatctt taggggtctc tggctcaagt    5760
cagtcatcat caaacacctg ggaaaaactg ccccacct  tgcctccact gcctaacgac    5820
tgagctgacc tccaggcttg cctctggtgt ccctgtgtt  atttctactg aaacatccag    5880
tcccaggcca ggctgcacaa tatgtacagg gtttaaggac aatgggaaga cccatcacta    5940
tccatttcta ggatgtcctt gcaaagggaa accacagaaa aatatacct  agggaaacaa    6000 agtaggactg aaggtggaag ggacccagca cttgaatgtt ccaggtgagg accctacagt    6060
gggccaagta gtcaactggt cagggaggga ccaggagagg caccaggagc tgtgacctcc    6120 ccccagtcc  tgtgtctgtt cacagcccaa tgctgctgct taattcacac ttgagaaagt    6180
ctgtgcttcc cccacaccga gcaggcagcc tcgcagtctc tgagatctca gatcatcgtg    6240
catctgtctt gtgacacatg cacccaccgt gggtttttaa gggctcaggt gggctgagag    6300
gtggaaggtg ccaactctga ttgaaagatg cctgtgagga atcaaaggtg ccacacaggg    6360
caatcttctc tctgttatct gcacagcgga gctgcccaag ccctccatct ccagcaacaa    6420
ctccaaaccc gtggaggaca aggatgctgt ggccttcacc tgtgaacctg agactccagga    6480 cgcaacctac ctgtggtggg taacaatca  gagcctcccg gtcagtccca ggctgcagct    6540
gtccaatggc aacaggaccc tcactctatt caatgtcaca agaaatgaca cagcaagcta    6600
```

```
caaatgtgaa acccagaacc cagtgagtgc caggcgcagt gattcagtca tcctgaatgt    6660
cctctgtgag tatatctgct cctctctggc ccaggctgcc agcccaaatc cacagggcca    6720
gaggcaggat ttctcagtcc ctctcaggtt caagtacaca gaccctcaac cctggacatc    6780
cagactgtct gtgactttct gccccagaaa aacctgggca gaccaagtct tgaccaagaa    6840
taggagggga ggggctgctt ctgtcctggg aggctcaggg tccacaccct atgatgggag    6900
aaacaggtga atatctcaga ctcaggctca gtagatacaa gaggggtttg gctgagactt    6960
taggattgtg attcagctta gagggacact gtggtccttc catagaccag gaacttccac    7020
ttccctctga caatatcacc tgtggcttta ttttgtttgc tccagatggc ccggatgccc    7080
ccaccatttc ccctctaaac acatcttaca gatcagggga aaatctgaac ctctcctgcc    7140
acgcagcctc taacccacct gcacagtact cttggtttgt caatgggact ttccagcaat    7200
ccacccaaga gctctttatc cccaacatca ctgtgaataa tagtggatcc tatacgtgcc    7260
aagcccataa ctcagacact ggcctcaata ggaccacagt cacgacgatc acagtctatg    7320
gtaagtggat ccacgaagca ctgacatcat gttttgaggt ggagtctgtc tggttttcaa    7380
acaagagcca ggaagacatt ttctatccca gcctgtgtcc agtgggcaca agcaaatccc    7440
agattctccc actgaacctc cccaatatgt ctctacagac tcttttcttc ttgttctgat    7500
ttctcatggc gggccccagg tccagcttgg aatgtgggga ggaggctccc tcagccccac    7560
agccctgtgt agtggaggaa gcttcacaga gcgggaagga gcaagggttc tcaaggtcaa    7620
gttgcttctc tctgtcacca atgtgtccct ttctgtcacc tctttgtgtt cttttgccta    7680
ctccatgagc tacaagcaac attcaaggct ttgaaacaag ctcatacttt tttcccaaat    7740
gagagaagga agcccttgg gtgagggaga cacagctcag actgctccct gctctgctct    7800
gggctcccct gggtgactgg ccttgcctga ctccacctag gtgggaacga ggtgtgtgga    7860
gaaggagccc gggtggtctg tcctgaattc ggctaaatca agctgccaat caacaccaaa    7920
gcttcccttc gtcccagtca ggctgcagga aaatggaaag agagggagcc tcagggcaga    7980
ctcctgagct gcgtcctggc tctgatgtca ccagctatat gaggctgtgg gcacagcaca    8040
tgggacacag cacaggggac agcaagtgac ccacacttgg agaaatcagg agattcacca    8100
caggggctct gcacggcagg gaatggcagt gtcaaaaatc gtgtgtttat acagatggta    8160
acagtacata tctaacacaa acttaccatc ttaacttttc tacacatgca gttcagtggt    8220
attaaatata ttccccttgt tctgcttcca tcaccaccat ctacccacag gactctttc    8280 ttcctcccaa aatgaaactc tgttcccatc aaactcctgg gcagagctgc cccatctatg    8340
gcccacagtc tgatccctga cttgtcacct ctagacatgc tcctagtctc ctgcactatt    8400
tctgctcaaa catccatctc catcatcacc tatctctagg atgtccttaa atagcaaagc    8460
ctcagagcaa acacaacttg gctgggtggt gtgggactgt gcagctggaa gaaacgcagc    8520
tccttcaaat tccaggtgag gaccccaatg ggccaggcag ccagccagtc aggaaaggac    8580
cagaagtgct gggggctgtg acccccagcc ctgtgtctgt ccacaaccca atgctactgc    8640
ccaattcaca cttgagaaag tctgtgcttc tcccacacaa aacagccagc ctcatggtct    8700
ctgagccctc agatcattgt gcatctgtct tgtgacgcac acacacctgc catgagcttt    8760
taaggactca gttgggctga gaggtgggag atgccaactc tgattgatag atgcccgtgg    8820
aggaatcaca ggtgccacac agggcaatct tctctctgtt atctgcacag cagagccacc    8880
caaacccttc atcaccagca acaactccaa ccccgtggag gatgaggatg ctgtagcctt    8940
```

```
aacctgtgaa cctgagattc agaacacaac ctacctgtgg tgggtaaata atcagagcct    9000
cccggtcagt cccaggctgc agctgtccaa tgacaacagg accctcactc tactcagtgt    9060
cacaaggaat gatgtaggac cctatgagtg tggaatccag aacgaattaa gtgttgacca    9120
cagcgaccca gtcatcctga atgtcctctg tgagtatctt ctgttcctct gtggctcagg    9180
ctgccagccc aaatccacat agccaaagtc caggcctctc agtccctctc aggcccaagg    9240
acagagactt ttacccctgg acatccaggc tggccctacc cccagcaaat ccatgcaggc    9300
ccagtcctga ccaagaatag agggggaggg tctgctcctg tcctgtaaca ctcgggatcc    9360
acagctagtg atgggagaaa cagatgaatg tctcagactc tggctaattg gatacagtag    9420
gggtttggtt aggacttcag gattgtgact tggctcaggg ggacactgtt gcccttttcac   9480
agaccaggag cttcccctttt gctctgatga cattcacctg tggccctatt ctctttgctc   9540
cagatggccc agacgacccc accatttccc cctcatacac ctattaccgt ccaggggtga    9600
acctcagcct ctcctgccat gcagcctcta acccacctgc acagtattct tggctgattg    9660
atgggaacat ccagcaacac acacaagagc tctttatctc caacatcact gagaagaaca    9720
gcggactcta tacctgccag gccaataact cagccagtgg ccacagcagg actacagtca    9780
agacaatcac agtctctggt aagtggatcc ctggaccgtt agcaatatgt tctggagcgg    9840
aatctgtctg gttttcagaa aagagccagg aagaattttt ctttcctagt atgcatccaa    9900
tgggcacaag caatcccaaa ttcaatcctg agcactccca atttgtctct acaaacactc    9960
ttccccttgt ttttctgatt tctcatggct gaccttgtgt ccaccctgag aaatgtgggg   10020
agggtcttc atcagccctg agccctatgt agtggaaggg gcttcacaga gggggaagca    10080
agaagggtcc tcaaggtcaa gttgctcctc tctgtcacca atatgtccct ttctgacacc   10140
actttgtgtt cttttaccta atccatgagc tacaaggaac aactgaggct ttgaaacaag   10200
ctcacacttt ttccccaaat gagaggagga tgcccccttgg atgagggagg agcagctcag   10260
actctgctcc cggctccgct ccgggctccc ccagtgactg gccctgccct gatttcacct   10320
ggggtgggat ccgggcatgt ggagaaggtg ctcaggtggc ctgtcctgaa tctggctaag   10380
tcaagatgcc agatgaagcc aagccttccc agggtcaggc tacagggaaa taagaagaga   10440
gggagcctcg gggcagactc ctgagctgtg tcctggagtc tgaagtcacc ggctgtatga   10500
gattgtgggc acagcacatg ggacacagca cagaagacag tcagtggcac acacttggag   10560
acacacagag attcacccat ggggactcaa catggcaggg aaggggcagt gccaaaaagt   10620
gtgtgtttat agacagggta agaataccag ccactatata tatctaacat aagacaccat   10680
tttaaccttt ctatgtatgc agtttagtag cattaaatat tttcccatta ttctgctacc   10740
atcatcacca tccacccaca gaactctttt cttcttccta aaatgaaact ctgttcccat   10800
caaactcttg ggtagagctg cccacctgtg gcccacagcc tgaccctga actcacctct   10860
agcttgctc ctggtctcct gagctatttc tgcttaaaca cccatcccg tcatcaccca     10920
tctccaggat agccttgaaa caaaggctc agagaaaaca cccacggtt gggtggtgtg      10980
ggaccgtgca gctgaacgga attcagcacc cacaagtccc caggttggcc aggccgtcag   11040
ccatcaggga agaaccaaag gaggtgctgg gggctgtgac tcccagtcct gggtctgtcc   11100
acaacccaac gctgctgccc aattcacact tgagaaagtc tgtgcttccc ccacacaaag   11160
cagccggcct tacagtctct gagccctcag atcatcgtac atctgtcttg tgatacacac   11220
acctgccatg ggcttttaag gactcgggtg ggctgaaggg tgggagttgc caactctgat   11280
tgaaagatgc ctgtgaggaa tcaaaagtgc cacacagggc aatcttctct ctgttatctg   11340
```

```
cacagcggag ctgcccaagc cctccatctc cagcaacaac tccaaacccg tggaggacaa    11400
ggatgctgtg gccttcacct gtgaacctga ggctcagaac acaacctacc tgtggtgggt    11460
aaatggtcag agcctcccag tcagtcccag gctgcagctg tccaatggca acaggaccct    11520
cactctattc aatgtcacaa gaaatgacgc aagagcctat gtatgtggaa tccagaactc    11580
agtgagtgca aaccgcagtg acccagtcac cctggatgtc ctctgtgagt atcttctgtt    11640
cctctgtggc cctggtttcc aacccaaatc cacacagcca gaggccagga ctctcagttc    11700
tcctcaggtc caaagaggca gactcccacc cctggacacc caggctggcc ataacttcct    11760
gtcccaggaa aatttgggca acctcagcct ggaccaagaa taggagggga gaggctgctc    11820
ctgtcctagg aggctcagag tccacagcct atgatgggag aaacagatga acgtctcaga    11880
cccagactca gtggacatga gggttatggt ttggactttt tttttttttt tttttttttt    11940
gagacggagt ctcgctcttt cgcccaggct ggactgcagt ggtgtgatct cggctcactg    12000
caagctccgc ctcctaggtt cacaccattc tcctgcctca gcctcccgag taactgggat    12060
tacacacacg tgccgccatg cccagctaat gttttttgta ttttagtag agacgggtt    12120 tcaccatgtt ggtcaggctg gtctcgaact cctgatctgc cgcctcggc ctcccaaagt    12180 gctgggatta caggcgtgag ccaccgcacc cggccgattt ggactttta acacaggatt    12240 gggacaggat tcagagggac actgtggccc ttctacaatc aggagcttcc cctttcctct    12300
gatgacatca cctgtggctt tgttctcttt gttccagatg ggccggacac ccccatcatt    12360
tcccccccag actcgtctta cctttcggga gcgaacctca acctctcctg ccactcggcc    12420
tctaacccat ccccgcagta ttcttggcgt atcaatggga taccgcagca acacacacaa    12480
gttctcttta tcgccaaaat cacgccaaat aataacggga cctatgcctg ttttgtctct    12540
aacttggcta ctggccgcaa taattccata gtcaagagca tcacagtctc tggtaagtgg    12600
ctccctggag catcagcatc atattctggg gtggagtcta tctggttctc accaaagagc    12660
caagaagaca ttttctttcc cagtctgtgt tccatgggca caaggaaatc ccaaattcta    12720
tcctgagccc cctcactcca tctcggccaa ctctctcctc cccggcttct ctgatatctc    12780
acggctgacc tcgggtccag cctggaatgt ggggagggc ctcccttagc cccagaaggc    12840
ccccaatagt gaaagggact tcatagtcca gaagaaagaa gggtccttaa ggtcgagttg    12900
ctcctctcta tcaccaatat gtccctttct gtcacctctt tgtgtttttt cacctactct    12960
gtgagctaca aggaacaagg aggctttgaa accagcccac acttttttccc caaatgagag    13020 gaggaagccc cttggatgag gcaggagcag ctcagactct gctccctgct ctgcgcccgg    13080
ctcacccggt gactggctct gccctggctc acttggggt gggaccgggg catgtggaga    13140
aggtgtccag gtggcctgtt ttgaatctgg gtaaatcaag ctgccaatcc acagcagagc    13200
ctcccttggg tcaggttgca gggaaatggg aaaagaggga gcctcgggac agactcctga    13260
gctgtgtcct ggctctgaag tcactggctg tatgaggctg tggacacagc acataggaca    13320
cagcagagga aagtgagtga cacacacttg gagaaatagg gagattcagc cataggggct    13380
ctgcatggga gggaacaggc agtgccaaaa agtgtgtgtt tatagagagg gtaagactat    13440
cagccactat atatatctaa cataaaactt accattaacc atttctaagt gtacaattaa    13500
gtgaaacagc ataaatatca atcaagtata ttgcccggtg tggtggctca tccctgtaat    13560
cccagcactt tgggaggcca aggcgagtgg atcacctgag gtcaggagtt caagatacag    13620
aaaaaaaaaa atagctaggc atggtggtgg gtgcctgtaa tcccagctac tcgggaggct    13680
```

```
gaggcaggag aatcgctcga acctgggcgg tgtagtttgc agtgagccga gattgagcca    13740
ctgcactcca gcctgggtga cagagtgaga ctacatcaca aaaaaaaaaa aaaaaaggaa    13800
aaaataaatc aagtcttttt atactcatgt ctaaccatca catcacacta tccatttcca    13860
gaacttttc atcttaccat actaaacctc tgtacccaat aaacagtaac tccttctctc    13920
ccctaaactc tggtaatctc cattctactt tctgtctcta ggtaatcaac tattctaacg    13980
atcttacaaa aatggaatta tataatagtt gtccttttgt gtctgcccta tttcacttag    14040
cataatgtct tcaaggttca tccattttgc accatgtatc acaatttctt ccttgttaag    14100
gttgaagaac attccattgt atggatacac ctcattttc tatccactta tctttcaatg    14160
gacttttcag ttgtttccac cttttggcta ttgtgagtaa tgctgctgtg aacatcagtg    14220
tacaaatatc tgttcaaatc actgccttca attcttttg gtgtatgtcc agaaatggaa    14280
ttggtagatc aaatgttaat tctttttttt gtttgtttgt ttgtttgttt gtttgttttt    14340
tgagatggag tctcgctctg tcgaccaggc tggagtgcac tggcgcgatc tcggctcact    14400
gcaagctccg cctcccgtgt tcacgccatt ctcctgcctc agcctcccga gtagctggga    14460
ctacaggtgc cgccaacaa gcttggctaa ttttttttt tttattttta gtagagactg    14520
agtttcacag tgttagccag gatggtctcg atctcctgac ctcgtgatcc gcctgccttg    14580
gcctcccaaa gtgctgggat tacaggcatg agccaccgtg tccggcccca aatgttaatt    14640
atttatttaa ttttttgagg aaccaccata ccatttttcca cagtagctaa tatttcacat    14700
ttctatcagc aatgcactag agttccaatt tttccacctc cttgaaaaca cttattgttt    14760
tgtggccatc ctgatgtgtg tgaggtggag tatcattgtg gctttgactt gcatatctct    14820
aagtgttagt gatgttgagc atatttgcat gtgcttgttg gccatttgta tatcttccta    14880
ggagaaatct ctactttagt cctttgtcca tttattaatt gggattttgg attttgtgg    14940
ttgttgattt gtaagagttc ttcatatatt ctggaaatta atcccttatc agatatatga    15000
tttgcaaata tatttcccat ttcataggtt gccttttcac tttctcgata atgttcttta    15060
atatataaaa gttttaatt ttcgaggccc tgcacggtgg ttcctgtaat cccagcactt    15120
tgggaggccg aggcaggtag attacaaggt caggagatca agaccatcct ggctaacaca    15180
gtgaaacccc gtctctacta aaaatacaaa aaaaattatc caggcgtggt ggtgggcgcc    15240
tgtagtccca gctactcaag aggctgaggc aggagaatgg catgaaccca ggaggcatag    15300
cttgcagtga gctgagatcg caccactgca ctccagccag ggtgacagag cgagactctg    15360
tcaaaaaaaa aaaaaaaaag tttttaattt tcatgaagtc cagtttatca atttttttct    15420
tttgttgcct atttgttgtt ataaccaaga catgactgtg aaattaaatg tcattaagct    15480
ttttccccta tgttttcttc tcagagtttt atacttttca ctcttacatt taggtctttg    15540
atccatttta ggttaatttg catatatggt atcaggcaaa gattcaactt gttcttgtgc    15600
atggatattc agctttccct atatcatttg ttgaaaagac tgtcctttcc ccattaaatg    15660
gtcttggcac cgttatcaaa aatcatttgg ccatatatgc aagcatttct ttctgggctc    15720
tatattctat tgctttggtt tcaatatctt cctttatgcc aataccacac tgtattgatt    15780
actgtggctt tatagcaaat gctgaaatca ggaagtgtga gtcctccagc ttcattcttt    15840
attttccagg ttgtttggct atttagagtc ctgagattcc atatgaattt caggatatgt    15900
ttttctattt ctgcaaaaaa tgtcactggg actctggtac aaattgcgtt gaacctgcag    15960
ctcactttga gtggtattgt cctcctagca atattgagac ttcccatcca tgaaaaaaaa    16020
atgtctttcc atctattgat gttgtcttta atttccttca gcagtgtttt atagttttca    16080
```

```
gggtacaatc ctttcacctc cttggttaag cttattctta actattttat actatttat      16140
gttaatgtga attggaaatt ttttcttaat ttccttttag attgttcatt gttagtgtgt      16200
agaagtacaa ctgatgtttg cgtgttgatt ttgtatcctg caacatcact gaatttattt      16260
attaactcta acaagttttt taatcttcag ggttttctac agagaagtcc aagttatctg      16320
aaaacacaga tcattttact tctttccaat ttggatgtct ttttttttct tgcctaattt      16380
ctctggctag gacttctaat actgtgtcga atagacgtgg caaaagcagg cattcttgtc      16440
ttgttcctgg tcttacaggg aaagcttcca gtctttctcc attgagtatc atgttagcat      16500
tgggcttttc acacattgcc tttattatgc tgaggtggtt tccttccatt cataattaga      16560
gtgttttgt tgtgaaagaa tggtgaattt tgtcaaatgc ttttattggt tctatctaat       16620
tataggccta ttaaatttt ttgtgtttcc aggaatttgt ccatttcatc taggttattc       16680
aacagtttgt tggcatacaa ttattcatag cattcttgta gtccttaata tttctgtaga      16740
atttgtagca ttggtagcaa tatctccatt ttctttttt ttttctttt ttttttaag        16800
agacagggtc tcactctgta gcccagcaca agctagagtg cagtggtgcc atcatagctt      16860
actgcagcct caacctccaa ggctcaagtg atcttctgcc ccagcctctt gagaagctgg      16920
gactacagac atgtgacacc aagcctggat agtttttaa agaaattttg tagacactgt       16980
gtctgcctat gttgcccagg ctggtcttga cctcctgacc tcaagtaatc ctcttgcttg      17040
agtctcccaa tgtgctggga ttaaatgtgt gagccgctat acctccattt tcatttctga     17100
ttttagtaat ttgaatcttc tctcttttt cttagtcaat ctaataaatg attgtcaatt       17160
ttgttgatct ttttttgaaga accaactttt ggtttcattg attccttcta ttgtttttca    17220
attttccatt ttatttattt aaactctaat ccttattatt tccttcatgt actatctgtg     17280
gtttgaggtg gttctttttc tgtatcctga agttgtaaag ttaggttgtt gatttgagat     17340
ctctctttat atttaatgta tttaccatta aatttctcac acaagattct taacttctct    17400
gagccttcaa ttcttcaact gaaaattgta ataattctca tcaccaggaa atggaggaaa     17460
aatgaaaatt gcaataagaa tgactgttta acagtattgt tttaaagatt taatgtaata    17520
ttcgattaag ctttcagcaa aatgctacac acagagggaa acttcataaa tattagctgc   17580
tattatcact actgttatta ttagcttgaa gttaggcagt tctagagcca atcctagat    17640
ccacttctca ctaattatat gactttggat aagttttttc accactccaa gtctctgtca  17700
tttcatctgt aagatggaaa tcatgcctac ccaacagggt tattgtatgg atcaaatgag   17760
atgccagaaa agcatttaca gtagctaaca tagcattaat catcagcctg agttgactag    17820
tgagagccaa gccccaaatg aaaacccact aggacatggt tactggctaa aatgggga       17880
gagaaaaaaa agttaagtgc aaagaatcaa gcctggtatg ttagttttca tccactgaga    17940
ttcagccaag atggaattag aggtgcaaga taatttaccg gggggaacca ccatgaggaa    18000
aagtggagta gaagtgggag gagcctgaga gagccctcag accacgatgc agatctgatt    18060
cctgagaagg agaaagagga gagagttta gatagtgatg cagttctcag agtttccaca   18120
aggctggtgg ggcgtcctca agcccctcac ccatgagaga gaagcagagt cccccagaac     18180
tgggcttttc attcccctgg tgggagccca tgagaagcga gttctctgtg caacggactt     18240
agtaaataca gaatgcacta gcctgggcct tctgccaatc aagtccctgc cacagagacc    18300
caacagactt atttatgcct accacaactg agacactgag aaaagatgc aaccatgaaa     18360
agatagaaag ttcaatgac acgcaaaaat agcaatcaga cttctcaaa tttcaaagcc      18420
```

-continued

```
ttcagaaata gctgagtgca gacaggccag ggtggaattg acagaagact gatcaccaac    18480
tagcaacaca gtgagagaga aaaaattgca actttcccac aaaactaatg cattccttga    18540
agcaacaagt agagactgct tcatgctgag agctggaacc tggggcaccc cactgtaaaa    18600
taacatcaca ttcattcctt ctcttttctt tccatgacgg acgattcagc atctggaact    18660
tctcctggtc tctcagctgg ggccactgtc ggcatcatga ttggagtgct ggttggggtt    18720
gctctgatat agcagccctg gtgtagtttc ttcatttcag gaagactggt aggtataatg    18780 gccttttcctc ttgttctgtt tcctgcagtg ctgactgcca tgcttgggag agggaaggga    18840
tttcttcacc tgtatctggg actggatctc ttcctcctac ccccaagctc ctgcttctca    18900
gcactaattc ctgcaggtct cttcttccct ggtcttcatg ctccctgtac gccactgtct    18960
cttagatata attatcccca ccctctgctc atttgtttcc cagattcaat acattgtcaa    19020
agcctcttgg tccttttta acatctcaca cttgtgtcat tctctccatt cccataaacc    19080
tcaacaactg ctcaaagtcc tgcttgaccc cttgttgcca gtctttgaaa tctttcttgc    19140
atatgactgc ctcattacct tcctaaaatc tagttcactc gcctactcaa gaagacacag    19200
gggcctactg tggtgtatta gataagttca catttcttct ctttactaat ctttttttact    19260 tcctttacca ccactccctt atataattcc atcatcctaa tagatctgtt tccctacaca    19320
tccctgcctc tccaccccac atgtacacag aattcttagt tccggtgtta cacctaaaaa    19380
catgtcaaac agggtgaccct ccttccactg tctgcactgt ggagttaccc acacccttaa    19440
tcacaagcaa cttctgacct catgaagaac aaagactgta gcattaacct gtgagtctta    19500
agctcaggac acaactgtgc ctgtgactga gaacctttc ctgataacca attcatatgt    19560
tcataacaga tacagaaatg aagaaggcaa ggtccttaat tctataacag gagacaaaac    19620
ctgaaaaata atcataatgc caaaatagaa aggagtgaac atcacaagaa attagagaaa    19680
tctgacggaa aatatagcta cacattggaa tcactcagaa acatttata aaatggatac    19740 ttaagtccca ccgataaaatt ccgatttact ggtctggagt gggacccagg cattcgtaat    19800
ttttaagcct ccccagatgc tactaatgtg tagccaggat ggagaaaccc tgttctaaat    19860
aggtaggact tggggctaaa cccatgactt tcagctagga ggattagaat tgcccatgga    19920 gttttttctgg ctgggcacgg tggctcacgc ctataatccc agcactttgg gaggccaagg    19980
cggacggatc aggagttcaa gaccagcctg accaacatgg tgaaacccccc tctctactaa    20040 aaatacaaaa aaatcagctg ggcatggtgg cacgtgcctg taattccagc tactcagaag    20100
gctgaggcag gagaatcgct tgaacccggg aggtggagat tgcagtgagc cgagatcgtg    20160
ccactgcact ccagcctggg cgacagagca agactccgtc tcaaaaaaaa aaaaaaaaa    20220 agaattgcct gtggagtttt tcaacatacg taagcctata ctttgttggc cctgttcatt    20280
aatgggctcc accaggaaat taggaatcta gttgagaaac agaagctgaa tggaaaggcc    20340
accttatttg atatgttaaa ttatatggga agcactgtca aatcattagt gatgttaaac    20400
cttctctaag ttatatttat gagtatgtta ttgatgtatt ccaaaagtta tataagaaat    20460
tctagaaatc taattggtta tcagccataa tgtcatatgc cacagaagta actaaatttc    20520
tatgtgagtt gtgttcttat tataataaat tatcatcaga tttttaactg tactcatttt    20580
aaatctttgt cattcacaga cagttgtttt gcttcttcct taaagcattt gcaacagcta    20640
cagtctaaaa ttgcttcttt accaaggata tttacagaaa agactctgac cagagatcga    20700
gaccatccta gccaacatcg tgaaacccca tctctactaa aaatacaaaa atgagctggg    20760
cttggtggcg cacacctgta gtcccagtta ctcgggaggc tgaggcagga gaatcgcttg    20820
```

-continued

```
aacccgggag gtggagattg cagtgagccc agatcgcacc actgcactcc agtctggcaa    20880
cagagcaaga ctccatctca aaaagaaaag aaaagaagac tctgacctgt actcttgaat    20940
acaagtttct gataccactg cactgtctga gaatttccaa aactttaatg aactaactga    21000
cagcttcatg aaactgtcca ccaagatcaa gcagagaaaa taattaattt catgggacta    21060
aatgaactaa tgaggataat attttcataa tttttattt gaaattttgc tgattcttta     21120
aatgtcttgt ttcccagatt tcaggaaact ttttttcttt taagctatcc acagcttaca    21180
gcaatttgat aaaatatact tttgtgaaca aaaattgaga catttacatt ttctccctat    21240
gtggtcgctc cagacttggg aaactattca tgaatattta tattgtatgg taatatagtt    21300
attgcacaag ttcaataaaa atctgctctt tgtatgacag aatacatttg aaaacattgg    21360
ttatattacc aagactttga ctagaatgtc gtatttgagg atataaaccc ataggtaata    21420
aacccacagg tactacaaac aaagtctgaa gtcagccttg gtttggcttc ctagtgtcaa    21480
ttaaacttct aaaagtttaa tctgagattc cttataaaaa cttccagcaa agcaacttta    21540
aaaaagtctg tgtgggccgg gcgcggtggc tcacgcctgt aatcccagca ctttgatccg    21600
ccgaggcggg cggatcacga ggtcaggaga tccagaccat cctggctaac acagtgaaac    21660
cccgtctcta ctaaaaatac aaaaaaagtt agccgggcgt ggtggtgggg gcctgtagtc    21720
ccagctactc aggaggctga ggcaggagaa cggcatgaac ccgggaggca gggcttgcag    21780
tgagccaaga tcatgccgct gcactccagc ctgggagaca aagtgagact ccgtcaaaaa    21840
aaaaaaaaa                                                            21849
```

<210> SEQ ID NO 32
<211> LENGTH: 1869
<212> TYPE: DNA
<213> ORGANISM: Homo sapiens
<220> FEATURE:
<223> OTHER INFORMATION: RNA18SN5

<400> SEQUENCE: 32

```
tacctggttg atcctgccag tagcatatgc ttgtctcaaa gattaagcca tgcatgtctg      60
agtacgcacg gccggtacag tgaaactgcg aatggctcat taaatcagtt atggttcctt     120
tggtcgctcg ctcctctcct acttggataa ctgtggtaat tctagagcta atacatgccg     180
acgggcgctg accccttcg cggggggat gcgtgcattt atcagatcaa aaccaacccg       240
gtcagcccct ctccggcccc ggccgggggg cgggcgccgg cggctttggt gactctagat     300
aacctcgggc cgatcgcacg cccccgtgg cggcgacgac ccattcgaac gtctgcccta      360
tcaactttcg atggtagtcg ccgtgcctac catggtgacc acgggtgacg gggaatcagg     420
gttcgattcc ggagagggag cctgagaaac ggctaccaca tccaaggaag gcagcaggcg     480
cgcaaattac ccactcccga cccggggagg tagtgacgaa aataacaat acaggactct      540 ttcgaggccc tgtaattgga atgagtccac tttaaatcct ttaacgagga tccattggag     600
ggcaagtctg gtgccagcag ccgcggtaat tccagctcca atagcgtata ttaaagttgc     660
tgcagttaaa aagctcgtag ttggatcttg ggagcgggcg ggcggtccgc cgcgaggcga     720
gccaccgccc gtccccgccc cttgcctctc ggcgccccct cgatgctctt agctgagtgt     780 cccgcgggc ccgaagcgtt tactttgaaa aaattagagt gttcaaagca ggcccgagcc     840
gcctggatac cgcagctagg aataatggaa taggaccgcg gttctatttt gttggttttc     900
ggaactgagg ccatgattaa gagggacggc cgggggcatt cgtattgcgc cgctagaggt     960
```

-continued

```
gaaattcttg gaccggcgca agacggacca gagcgaaagc atttgccaag aatgttttca    1020
ttaatcaaga acgaaagtcg gaggttcgaa gacgatcaga taccgtcgta gttccgacca    1080
taaacgatgc cgaccggcga tgcggcggcg ttattcccat gacccgccgg gcagcttccg    1140
ggaaaccaaa gtctttgggt tccgggggga gtatggttgc aaagctgaaa cttaaaggaa    1200
ttgacggaag ggcaccacca ggagtggagc ctgcggctta atttgactca acacgggaaa    1260
cctcacccgg cccggacacg gacaggattg acagattgat agctctttct cgattccgtg    1320
ggtggtggtg catggccgtt cttagttggt ggagcgattt gtctggttaa ttccgataac    1380
gaacgagact ctggcatgct aactagttac gcgaccccccg agcggtcggc gtcccccaac    1440
ttcttagagg gacaagtggc gttcagccac ccgagattga gcaataacag gtctgtgatg    1500
cccttagatg tccggggctg cacgcgcgct acactgactg gctcagcgtg tgcctaccct    1560
acgccggcag gcgcgggtaa cccgttgaac cccattcgtg atggggatcg gggattgcaa    1620
ttattcccca tgaacgagga attcccagta agtgcgggtc ataagcttgc gttgattaag    1680
tccctgccct ttgtacacac cgcccgtcgc tactaccgat tggatggttt agtgaggccc    1740
tcggatcggc cccgccgggg tcggcccacg gccctggcgg agcgctgaga agacggtcga    1800
acttgactat ctagaggaag taaaagtcgt aacaaggttt ccgtaggtga acctgcggaa    1860
ggatcatta                                                            1869
```

MARKER GENES FOR COLORECTAL CANCER CLASSIFICATION, METHOD FOR JUDGING LYMPH NODE METASTASIS FOR PROGNOSIS OF COLORECTAL CANCER AND KIT THEREFOR

This application is a National Stage entry under § 371 of International Application No. PCT/SE2017/050368, filed on Apr. 12, 2017, and claims priority to Swedish Patent Application No. 1630095-6, filed on Apr. 20, 2016.

The instant application contains a Sequence Listing which has been filed electronically in ASCII format and is hereby incorporated by reference in its entirety. Said ASCII copy, created on Oct. 8, 2018, is named 000640US_SL.txt and is 148,194 bytes in size.

FIELD OF THE INVENTION

The present invention relates to the field of classification, prognostics and treatment of cancer, in particular colorectal cancer.

BACKGROUND

Colorectal cancer (CRC) is the second leading cause of mortality among cancer patients in the world and the third most diagnosed form of cancer globally. It represents a huge burden on healthcare systems. The most important prognostic characteristic of CRC is presence or absence of lymph node metastasis (Chang G. J. et al. J. Natl. Cancer Inst., vol. 99, p. 433-441 (2007); Iddings D. and Bilchik A. J. Surg. Oncol., vol. 96, p. 671-677 (2007); Nicastri D. G. et al. J. Mol. Diagn., vol. 9, p. 563-571 (2007)). Relevant lymph nodes are accessible for investigation only when patients are resected for cure. Therefore, thorough determination of the lymph node status in the resected tumor specimen is crucial. Currently, approximately 50% of patients with tumor-cell-positive lymph nodes, i.e. stage III CRC (anyTN1-2M0) and about 25% with no detected tumor-cell positive lymph nodes, i.e. stage I (T1-2 N0M0) and stage II (T3-4N0M0) patients will recur (Bockelman C. et al. Acta Oncol., vol. 54, p. 5-16 (2015)). These results strongly suggest that tumor cells in lymph nodes may vary in aggressiveness, and that presence of tumor cells in the node in many cases is missed by the present standard method. Therefore it is of utmost importance to 1) accurately detect presence of tumor cells in lymph nodes and 2) determine their metastatic potential i.e. their aggressiveness. By improving determination of lymph node status, N-staging, and introducing the aggressiveness parameter for the spread tumor cells, improved staging will be achieved thereby avoiding undertreatment of stage I and II patients and overtreatment of stage III patients. Moreover, if patients with tumor cells in their lymph nodes can be classified into subgroups according to differences in risk of recurrence and cancer death this information may be used not only for treatment with the current arsenal of drugs but also in the development of new drugs, new treatment schedules as well as for follow-up schedules adjusted to the risk of recurrence, etc.

In clinical practice, presence or absence of lymph node metastasis is currently determined by histopathological examination of hematoxylin & eosin (H&E) stained tissue sections of resected regional lymph nodes. Present guidelines require that at least 12 lymph nodes should be examined (Tsai H. L. et al. BMC Surg., vol. 16, p. 17 (2016)) In the TNM classification, N1 signifies that 1 to 3 examined nodes were positive for presence of tumor cells and N2 that 4 to 6 nodes were positive. N2 patients have poorer prognosis than N1 patients. Moreover, the lymph node ratio, i.e., number of positive lymph nodes over total number of examined lymph nodes, is an important prognostic factor—the higher ratio the worse prognosis (Parnaby C. N. et al, Br. J. Cancer, vol. 113, p. 212-219 (2015)). The main reasons why tumor cells are missed by the routine method are twofold: too small sample size and inadequate sensitivity. At best, only a few % of the volume of the lymph node is examined by H&E staining of tissue sections. An alternative method is to determine the mRNA level of one or several biomarkers that is expressed in all tumor cells of this type, and to extract RNA from the entire lymph node or, as for ethical reasons is the current option, half the node. It has been shown that real time quantitative reverse transcriptase-polymerase chain reaction (qRT-PCR) analysis with copy standard is a most useful method for mRNA analysis of biomarkers. It is highly sensitive, objective, quantitative, and amendable for automation. It was found that mRNA analysis of the biomarker carcinoembryonic antigen (CEA, CEACAM5) is very useful for detection of tumor cells originating from the large intestine. This biomarker allowed the identification of stage I and stage II patients with tumor cells in their lymph nodes that were not detected by the present gold standard, i.e. histopathology of H&E stained sections (Ohlsson L. et al. Br. J. Cancer, vol. 95, p. 218-225 (2006); Ohlsson L. et al. Int. J. Cancer, vol. 130, p. 1833-1843 (2012)). Some of these patients have succumbed from recurrent disease (Ohlsson L. et al. Br. J. Cancer, vol. 95, p. 218-225 (2006); Ohlsson L. et al. Int. J. Cancer, vol. 130, p. 1833-1843 (2012)). Thus, a more sophisticated stratification was obtained by using this marker compared to the gold standard only. The biomarker cytokeratin 20 (CK20) is also useful for this purpose, albeit somewhat less sensitive (Ohlsson L. et al. Br. J. Cancer, vol. 95, p. 218-225 (2006). Currently there is only one published biomarker for CRC that displays the properties of an aggression marker, namely kallikrein related peptidase 6 (KLK6) (Ohlsson L. et al. Br. J. Cancer, vol. 107, p. 150-157 (2012)). It is ectopically expressed in CRC tumor cells and appears to be expressed at increasing levels with increasing aggressiveness.

A generally accepted pathway for the development of distant metastases in CRC is that tumor cells leave the primary site in colon or rectum via lymphatic vessels, first settle in a regional lymph node, and thereafter, spread to distant sites like the liver. It is the distant metastasis that eventually kills the patient. Evidence for this pathway is the fact that presence or absence of tumor cells in a regional lymph node is the best prognostic marker for CRC death or survival.

The present invention concerns: 1) the identification of two new aggression biomarkers for CRC; one expressed in the CRC tumor cells themselves and the other in supporting cells in the microenvironment of the lymph node. 2) A method for determination of lymph node status, which accurately detects presence or absence of tumor cells in the lymph nodes, and in addition provides information on the aggressiveness of these cells. In the proposed method, quantitative mRNA levels of the 2 new biomarkers and 3 previously described biomarkers are determined. If applied for CRC lymph node analysis, it will accurately determine lymph node involvement and allow classification of CRC patients into different risk groups with respect to risk for recurrence and cancer death after the primary treatment, i.e. surgical resection of the tumor. This goal has hitherto not been possible to achieve.

OBJECT OF THE INVENTION

It is an object of the present invention to provide a group of molecular biomarkers, which are useful for classification, for prediction of prognosis and for guiding treatment decisions of a subject with colorectal cancer.

It is another object of the present invention to provide objective and quantitative methods for classifying colorectal cancer in a subject, as well as for using the classification for predicting prognosis of the subject and for making a treatment decisions for the subject.

DESCRIPTION OF THE INVENTION

The present inventors have identified the expression levels of the genes solute carrier family 35 member D3 (SLC35D3) (GenBank NM_001008783) and periostin, osteoblast specific factor (POSTN) (GenBank NM_006475) as molecular biomarkers that can be used for determining the metastatic potential and/or tumor aggressiveness of a colorectal cancer in a subject.

Expression levels of the genes SLC35D3 and POSTN can preferable be used together with the expression levels of the gene kallikrein related peptidase 6 (KLK6) (GenBank NM 002774), and even more preferably also together with the expression level of the gen mucin 2, oligomeric mucus/gel-forming (MUC2) (GenBank NM_002457) for determining the metastatic potential and/or tumor aggressiveness.

The method can be applied to determine gene expression levels in regional lymph node samples obtained from the subject, or in primary intestinal tumor, blood, and/or feces samples obtained from the subject.

The expression levels of these genes can be related to the expression level of the gene carcinoembryonic antigen related cell adhesion molecule 5 (CEACAM5) (GenBank NM_004363), which is a known tumor marker, and/or related to the level of 18S rRNA.

Accordingly, one aspect of the present invention provides methods for determining the metastatic potential and/or tumor aggressiveness of a colorectal cancer in a subject, comprising the steps:
  a) determining the gene expression levels of genes SLC35D3, and POSTN in a regional lymph node sample obtained from the subject; and
  b) comparing the gene expression levels determined in step a) with reference gene expression levels of the same genes in a reference patient population;
wherein higher expression levels of the genes SLC35D3 and POSTN compared to the reference are associated with an increased metastatic potential and for tumor aggressiveness.

Preferably the method can further comprise determining the gene expression level of the gene KLK6 in said sample.

Accordingly, in one embodiment the first aspect of the present invention provides methods for determining the metastatic potential and/or tumor aggressiveness of a colorectal cancer in a subject, comprising the steps:
  a) determining the gene expression levels of genes SLC35D3, POSTN and KLK6 in a regional lymph node sample obtained from the subject; and
  b) comparing the gene expression levels determined in step a) with reference gene expression levels of the same genes in a reference patient population;
wherein higher expression levels of the genes SLC35D3, POSTN and KLK6 compared to the reference are associated with an increased metastatic potential and f/or tumor aggressiveness.

Preferably the method can further comprise determining the gene expression level of the gene MUC2 in said sample.

Accordingly, in another embodiment the first aspect of the present invention provides methods for determining the metastatic potential and/or tumor aggressiveness of a colorectal cancer in a subject, comprising the steps:
  a) determining the gene expression levels of genes SLC35D3, POSTN, KLK6 and MUC2 in a regional lymph node sample obtained from the subject; and
  b) comparing the gene expression levels determined in step a) with reference gene expression levels of the same genes in a reference patient population;
wherein higher expression levels of the genes SLC35D3, POSTN, KLK6 and MUC2 compared to the reference are associated with an increased metastatic potential and for tumor aggressiveness.

Preferably the method can further comprise the steps
  c) determining the gene expression level of the gene CEACAM5 and the level of 18S rRNA in said sample;
  d) based on the results obtained in steps a) and c) calculating the ratios SLC35D3/CEACAM5, KLK6/CEACAM5, POSTN/18S rRNA, and MUC2/CEACAM5;
  e) giving the ratios obtained in step d) the values of (+1) or (0) depending on whether said ratio is larger than a cut-off value based on the same ratio in said reference patient population, and where ratios higher than the cut-off value obtain a value of (+1) and values lower than the cut-off level obtain a value of (0); and
  f) calculating an index using the ratios obtained in step e) using the formula [A=SLC35D3/CEACAM5+KLK6/CEACAM5+POSTN/18S rRNA−MUC2/CEACAM5];
wherein the index (+3) is associated with very high metastatic potential and/or tumor aggressiveness, the index (+2) and (+1) with high metastatic potential and/or tumor aggressiveness, and the index (0) and (−1) with low metastatic potential and/or tumor aggressiveness.

Said cut-off values can be the ratios of the 7th decile of said reference patient population, the ratios of the $3^{rd}$ quartile of said reference patient population, or the ratios of the 8th decile of said reference patient population.

The methods can be performed in vitro and/or ex vivo.

The methods can further comprise the additional step of treating colorectal cancer in a subject in need thereof.

In another aspect the present invention provides methods of determining the metastatic potential and/or tumor aggressiveness of a colorectal cancer in a subject, comprising:
  a) determining the gene expression levels of the genes SLC35D3, KLK6, MUC2 and CEACAM5 in a primary intestinal tumor, blood, or feces sample obtained from the subject;
  b) based on the result obtained in step a) calculating the ratios SLC35D3/CEACAM5, KLK6/CEACAM5 and MUC2/CEACAM5; and
  c) comparing the ratios determined in step b) with reference ratios calculated from expression levels of the same genes in a reference patient population;
wherein higher ratios SLC35D3/CEACAM5 and KLK6/CEACAM5 compared to reference are associated with an increased metastatic potential and/or tumor aggressiveness and a higher ratio MUC2/CEACAM5 compared to reference is associated with decreased metastatic potential and/or tumor aggressiveness.

The methods can be performed in vitro and/or ex vivo.

The methods can further comprise the additional step of treating colorectal cancer in a subject in need thereof.

According to the invention the gene expression levels can be determined by quantifying the amount of mRNA expressed from said genes.

The amount of mRNA can be determined by hybridization, sequencing or quantitative RT-PCR.

More specifically the amount of mRNA can be determined by use of a method selected from microarray and bead array technologies, transcriptome sequencing, real time quantitative RT-PCR, multiplex quantitative RT-PCR.

According to the methods the gene expression levels can be determined using RNA or DNA copy standard and/or the 18S rRNA level can be determined using 18S rRNA standard.

Another aspect of the present invention provides methods for determining the prognosis of a subject diagnosed with colorectal cancer. Said method can comprise determining the metastatic potential and/or tumor aggressiveness of a colorectal cancer in a subject using a method according to the present invention.

Said methods can comprise determining that the subject has a good prognosis if the metastatic potential and/or tumor aggressiveness is low, or determining that the subject has a poor prognosis if the metastatic potential and/or tumor aggressiveness is high. Poor prognosis can be a decrease in the likelihood of survival compared to the good prognosis.

The methods can be performed in vitro and/or ex vivo.

The methods can further comprise the additional step of treating colorectal cancer in a subject in need thereof.

Another aspect of the present invention provides methods for determining the treatment for a subject diagnosed with colorectal cancer and having a tumor. Said method can comprise determining the metastatic potential and/or tumor aggressiveness of a colorectal cancer in a subject using a method according to the present invention and determining the treatment for said subject dependent on the metastatic potential and/or tumor aggressiveness determined.

The methods can be performed in vitro and/or ex vivo.

The methods can further comprise the additional step of treating colorectal cancer in a subject in need thereof.

The treatment can be to give postoperative treatment, e.g. chemotherapy, to a patient determined to have a high metastatic potential and/or tumor aggressiveness.

The treatment can be to abstain from postoperative treatment to a patient with a low metastatic potential and/or tumor aggressiveness.

Another aspect of the present invention provides a kit for determining metastatic potential and/or tumor aggressiveness of a subject diagnosed with colorectal cancer.

The kit can comprise nucleic acid primers and probes for determination of the gene expression levels, of one or more of the genes CEACAM5, KLK6, POSTN, SLC35D3, and MUC2 and optionally nucleic acid primers and probes for determination of the level of 18S rRNA.

In one embodiment the invention provides a kit for determining metastatic potential and/or tumor aggressiveness of a subject diagnosed with colorectal cancer, comprising nucleic acid primers and probes for determination of the gene expression levels of the genes SLC35D3 and POSTN.

In another embodiment the invention provides a kit for determining metastatic potential and/or tumor aggressiveness of a subject diagnosed with colorectal cancer, comprising nucleic acid primers and probes for determination of the gene expression levels of the genes SLC35D3, POSTN and KLK6.

In another embodiment the invention provides a kit for determining metastatic potential and/or tumor aggressiveness of a subject diagnosed with colorectal cancer, comprising nucleic acid primers and probes for determination of the gene expression levels of the genes SLC35D3, POSTN and MUC2.

In another embodiment the invention provides a kit for determining metastatic potential and/or tumor aggressiveness of a subject diagnosed with colorectal cancer, comprising nucleic acid primers and probes for determination of the gene expression levels of the genes SLC35D3, POSTN, KLK6 and MUC2.

In another embodiment the invention provides a kit for determining metastatic potential and/or tumor aggressiveness of a subject diagnosed with colorectal cancer, comprising nucleic acid primers and probes for determination of the gene expression levels of the genes SLC35D3, POSTN, KLK6, MUC2, and CEACAM5.

The nucleic acid primers and probes can be selected from those given in Table 1. More specifically the nucleic acid primers and probes can be selected from SEQ ID NO:1, 2, 3, 4, 5, 6, 7, 8, 9, 10, 11, 12, 13, 14, or 15.

The kit can further comprise mRNA, RNA and/or DNA copy standards.

Another aspect of the present invention provides methods for treatment of colorectal cancer. Said method can comprise determining the metastatic potential and/or tumor aggressiveness of a colorectal cancer in a subject using a method according to the present invention, and treating said subject dependent on the metastatic potential and/or tumor aggressiveness determined.

The treatment can be to give postoperative treatment, e.g. chemotherapy, to a patient determined to have a high metastatic potential and/or tumor aggressiveness.

The treatment can be to abstain from postoperative treatment to a patient with a low metastatic potential and/or tumor aggressiveness.

FIGURE LEGENDS

FIG. 1. Expression levels of CEACAM5, MUC2, KLK6, POSTN and SLC35D3 mRNA in primary CRC tumors (●) (n=56) and normal colon tissue (n=5) (○)

Figure 2:
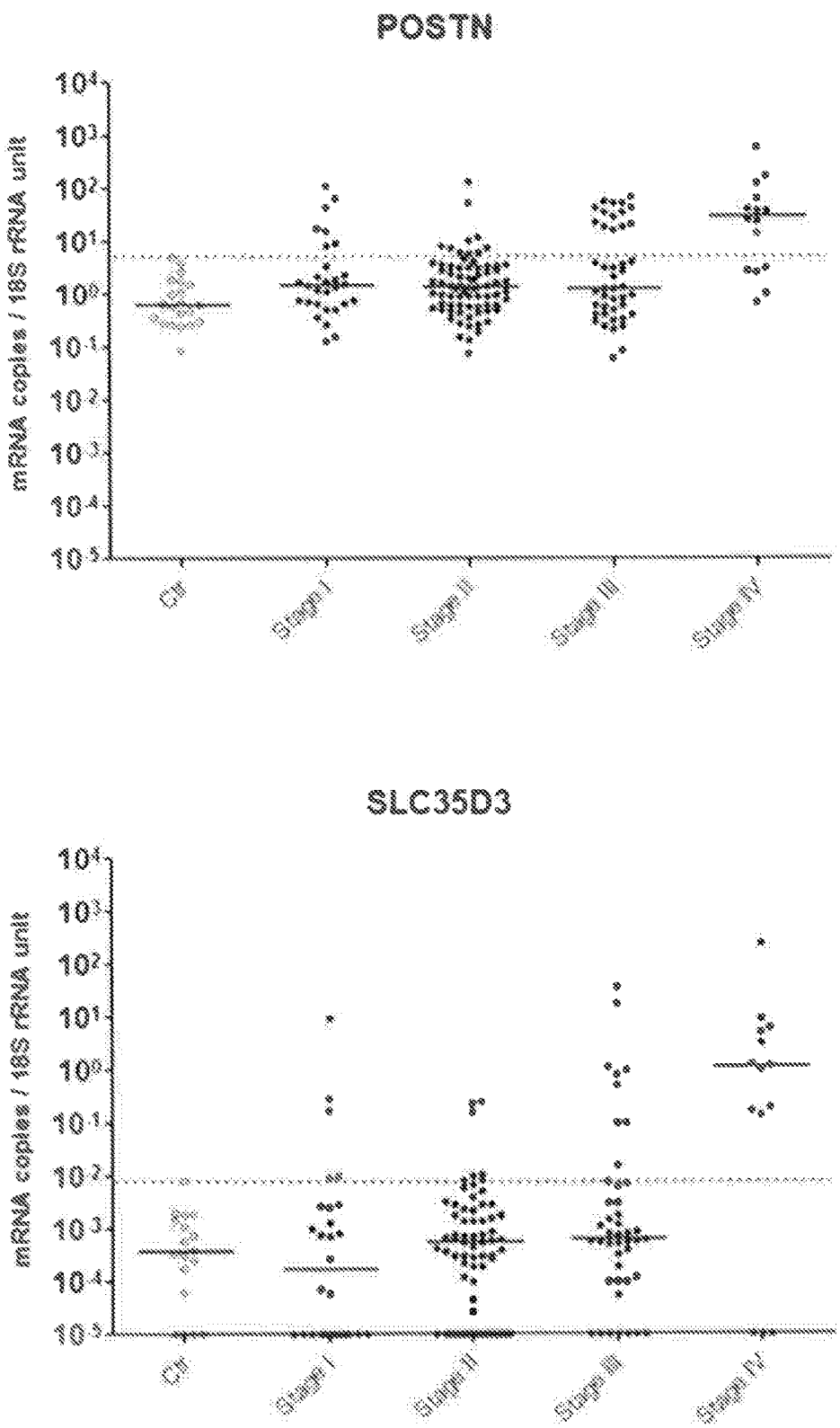

FIG. 2. (A) SLC35D3 and (B) POSTN mRNA expression levels in lymph nodes of patients with stage I to IV CRC and control patients (Ctr). Each of the 166 CRC patients and 23 control patients is represented by the lymph node with the highest mRNA value.

Figure 3:
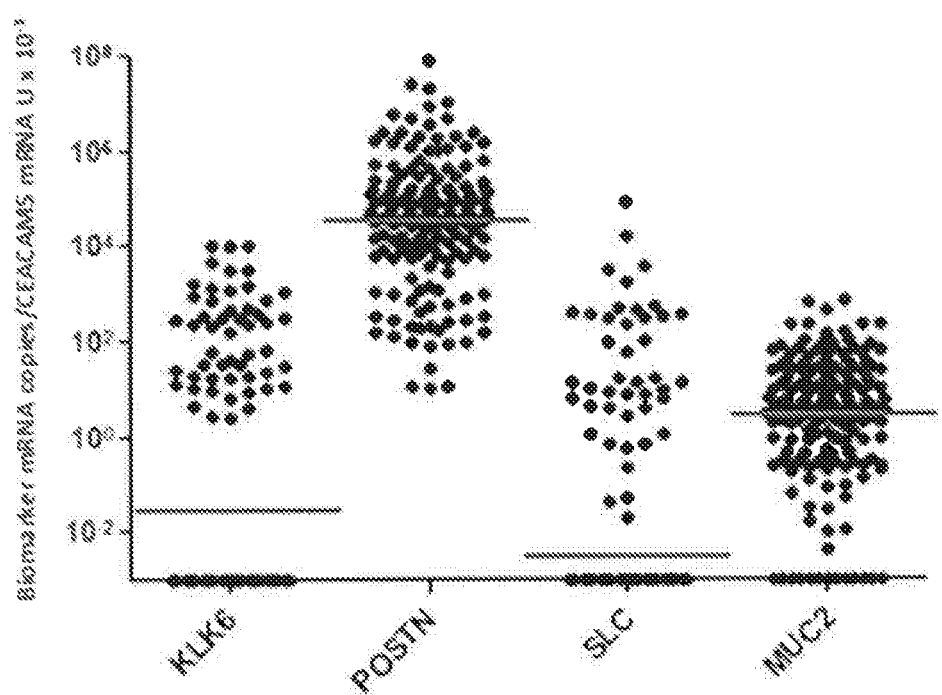

FIG. 3. Ratios of biomarker mRNA over CEACAM5 mRNA in lymph nodes from patients with stage I to IV CRC. Each of the 166 patients is represented by the lymph node with the highest mRNA value and indicated by a filled circle.

Figure 4:
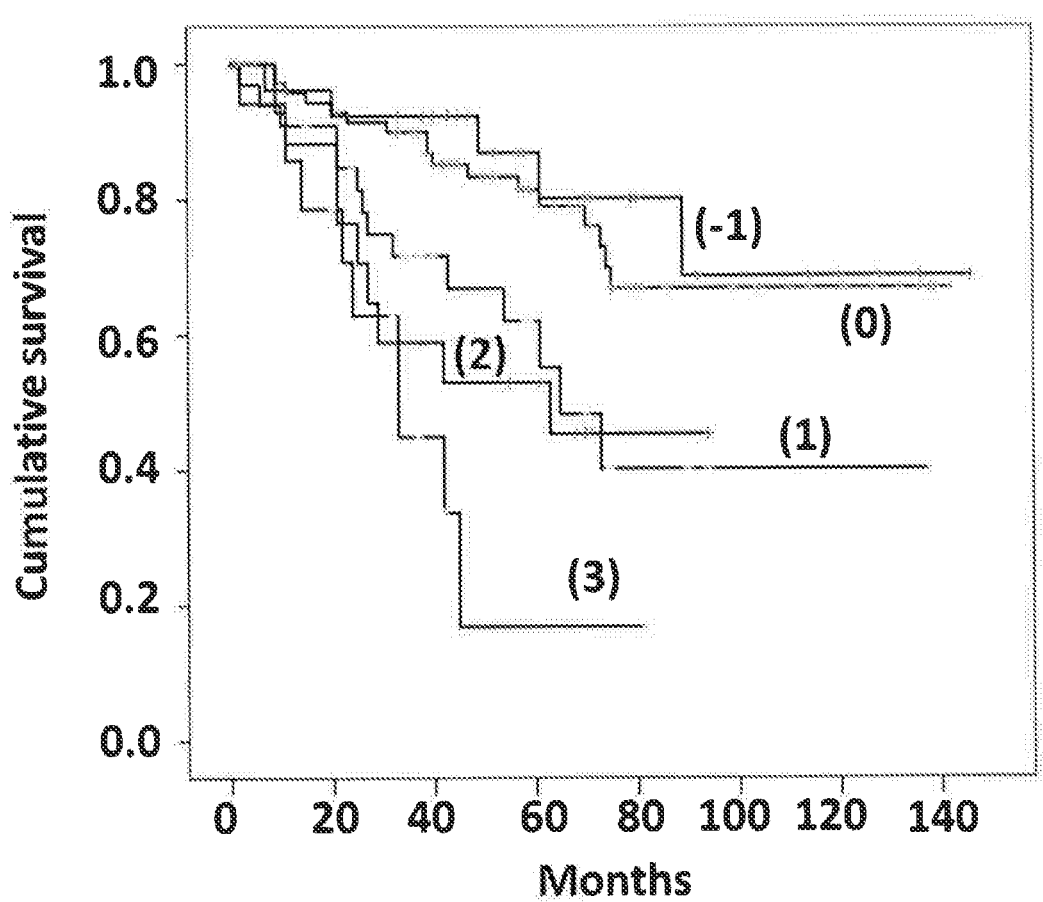

FIG. 4. Cumulative survival curves according to Kaplan-Meier for CRC patients (n=166). Patients are classified in groups (−1, 0, +1, +2 and +3) based on the mRNA value of the biomarkers SLC35D3, POSTN, KLK6, MUC2 and CEACAM5 and calculated according to formula: (Formula A=SLC35D3/CEACAM5+KLK6/CEACAM5+POSTN/ 18S rRNA-MUC2/CEACAM5). The 8th decile of the mRNA values for each marker was used to classify the marker value as positive or negative, giving the former a value of (1) and the latter a value of (0). The lymph node with the highest CEACAM5 mRNA value was chosen to represent the patient. For further details see text.

Figure 5:
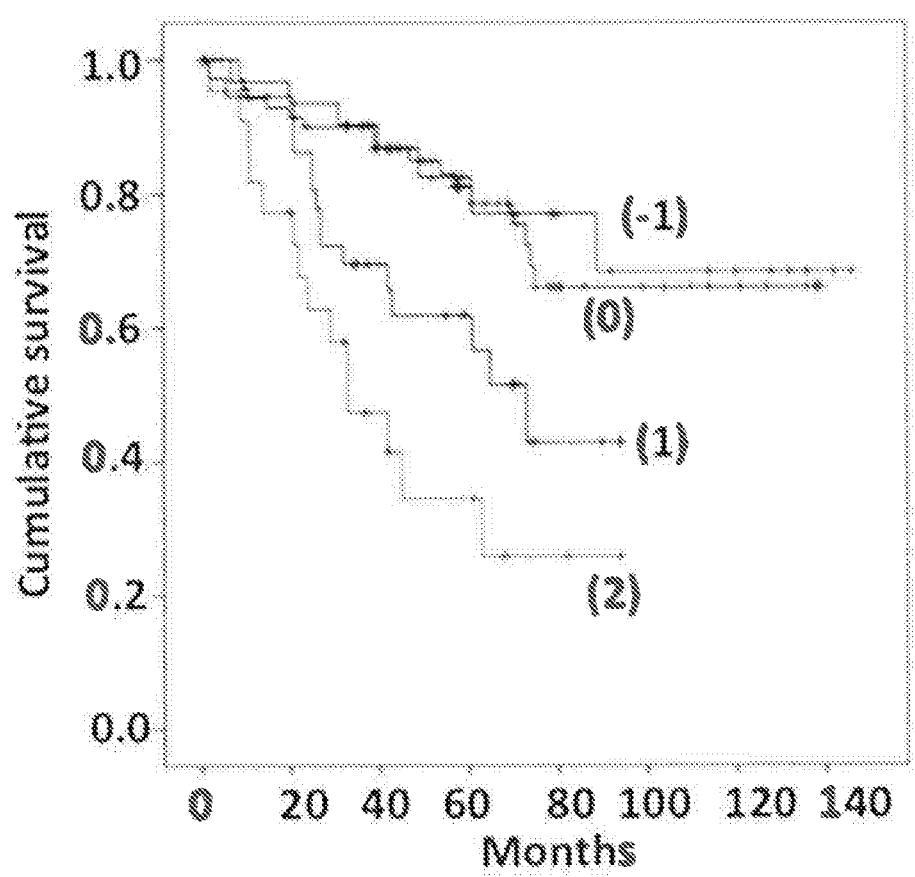

FIG. 5. Cumulative survival curves according to Kaplan-Meier for CRC patients (n=166). Patients are classified in groups (−1, 0, +1, and +2) based on the mRNA value of the biomarkers SLC35D3, KLK6, MUC2 and CEACAM5 and calculated according to formula: (Formula E=SLC35D3/

CEACAM5+KLK6/CEACAM5−MUC2/CEACAM5). For further details see legend to FIG. 4 and text.

EXAMPLES

Identification of Genes and Gene Signatures that are Significantly Correlated to Risk of Cancer Death in Colorectal Cancer Subjects A gene that is of importance for tumor progression is most likely expressed both in the primary tumor tissue and in secondary tumors present in a regional lymph node draining the intestine. A microarray-search for progression markers was performed by analyzing RNA from 4 different H&E positive lymph nodes (i.e. tumor cell containing lymph nodes) of 4 patients with stage III CRC plus 3 primary tumors from 3 of these patients. RNA from 7 control patients (lymph nodes from 2 ulcerative colitis patients, 1 Crohns' colitis patient, 1 colon lipoma patient and 3 normal colon epithelial cells samples) were also analyzed. CRC samples were compared individually relative to all control samples as one group. The microarray data were filtered by setting statistical significance to P<0.05, fold change to ≥5, and minimum intensity to 15. In this way a number of genes that were expressed in most of the CRC samples (≥5/7) with a fold change ≥5 times were identified. Among these were SLC35D3, POSTN and KLK6.

Commercially available real-time qRT-PCR assays were used to verify the microarray results (TaqMan Gene Expression Assays) for POSTN, SLC35D3 and KLK6. In the latter case 3 assays for different splice forms. All three genes were expressed in a panel of primary CRC tumors samples (n=8) while SLC35D3 and KLK6 but not POSTN were expressed in all CRC cell lines (n=5).

Real-time qRT-PCR assays with RNA copy standards using the Taqman EZ RT-PCR technology as described (Fahlgren A. et al. Clin. Exp. Immunol., vol. 131, p. 90-101 (2003); Ohlsson L. Thesis, ISBN 978-91-7459-318-1 (2011)) were constructed. Primer and probe sequences for real-time qRT-PCR assays for SLC35D3, POSTN, KLK6, MUC2, and CEA, mRNA are shown in Table 1 and primers for construction of RNA copy standards in Table 2. Using these assays a panel of RNA samples including primary CRC tumors, normal colon tissue and purified colon epithelial cells, CRC cell lines, peripheral blood mononuclear cells (PBMCs), different immune cell lines and a fibroblast cell line were analyzed (Table 3). The individual values of 56 primary CRC tumors and 5 normal colon samples are shown in FIG. 1. For comparison the result for CEACAM5 and MUC2 is included (Ohlsson L. Thesis, ISBN 978-91-7459-318-1 (2011)).

It is apparent that all five biomarker mRNAs are expressed in primary CRC tumors, although at highly different copy number levels normalized to the 18S rRNA content in the sample, from a median of 164 for CEACAM5 to 0.17 for SLC35D3 reflecting the abundance of the protein molecule that the particular mRNA is coding for.

Secondly, that the CRC cell lines express all marker mRNAs except POSTN, which instead is expressed at high levels in the fibroblast cell line.

Thirdly, that none of the markers is expressed to a significant degree in immune cell lines.

Fourthly, that CEACAM5 is expressed at similar levels in primary CRC tumors and normal colon epithelial cells. Based on the latter finding and previous knowledge (Ohlsson L. et al. Br. J. Cancer, vol. 95, p. 218-225 (2006)), CEACAM5 was considered to be the preferable marker for cells originating from the large intestine. Moreover, its high expression level makes it a very sensitive marker for detection of colorectal cancer cells in lymph nodes.

Fifthly, MUC2 measures to what extent a CRC tumor is mucinous or not, MUC2 being the dominant mucin in colon

TABLE 1

Primer and probe sequences used in qRT-PCR assays for SLC35D3, POSTN, KLK6, MUC2, CEACAM5, and 18S rRNA

| Gene | 3' primer sequence (reverse) | 5' primer sequence (forward) | Probe sequence |
| --- | --- | --- | --- |
| SLC35D3 | AGC ACT CCC GTG ACG TAC C (SEQ ID NO: 1) | TCA TCA CCA CCT GCG GC (SEQ ID NO: 2) | CCT GGC AGG AGC CGG CGA (SEQ ID NO: 3) |
| POSTN | CCC TTG CTT ACT CCC TTT CTC (SEQ ID NO: 4) | ACA GCT CAG AGT CTT CGT ATA TCG (SEQ ID NO: 5) | ACA GCT GTC TGC ATT GA (SEQ ID NO: 6) |
| KLK6 | AAG GTT ATG CTT CCC CAG G (SEQ ID NO: 7) | CTT ATC CAT CCA CTG TGG GTC (SEQ ID NO: 8) | CAC TGC AAA AAA CCG AAT CTT CAG GTC (SEQ ID NO: 9) |
| MUC2 | TAG TGT CCA GCT CCA GCA TGA (SEQ ID NO: 10) | AAG AGC GAT GCC TAC ACC AAA (SEQ ID NO: 11) | TCC CGG TTC CAC ATG A (SEQ ID NO: 12) |
| CEACAM5 | TGT AGC TGT TGC AAA TGC TTT AAG (SEQ ID NO: 13) | CTG ATA TAG CAG CCC TGG TGT AGT (SEQ ID NO: 14) | AGG AAG ACT GAC AGT TGT (SEQ ID NO: 15) |
| 18S rRNA | CCG CTC CCA AGA TCC AA (SEQ ID NO: 16) | GTA ATT CCA GCT CCA ATA GCG TA (SEQ ID NO: 17) | CTG CAG TTA AAA AGC (SEQ ID NO: 18) | and rectum. Patients with mucinous tumors have a better prognosis than those with non-mucinous tumors (Byrd J. C. and Bresalier R. S. Cancer Metastasis Review, vol. 23, p. 77-99 (204); Ohlsson L. et al. Int. J. Cancer, vol. 130, p. 1833-1843 (2012)).

Finally, in contrast to CEACAM5 and MUC2, both KLK6 and SLC35D3 were expressed in CRC tumors and most CRC lines but not in normal colon epithelial cells, i.e. they are ectopically expressed in CRC tumors.

rRNA and expressed as mRNA copies/18S rRNA unit. Previous studies by our group have demonstrated that 18S rRNA is an excellent RNA species for normalization (Bas A. et al, Scand. J. Immunol., vol. 59, p. 566-573 (2004);

TABLE 2

Primer sequences used in RT-PCR for cloning of cDNA and construction of RNA copy standards for SLC35D3, POSTN, KLK6, MUC2, CEACAM5, and 18S rRNA

| Gene | 3' primer sequence (reverse) | 5' primer sequence (forward) |
|---|---|---|
| SLC35D3 | CAGCACTCCCGTGACGTAC (SEQ ID NO: 19) | CATCGGCGTCCTGGTTC (SEQ ID NO: 20) |
| POSTN | CCCTTGCTTACTCCCTTTCTC (SEQ ID NO: 4) | ACAGCTCAGAGTCTTCGTATATCG (SEQ ID NO: 5) |
| KLK6 | TGGATCACAGCCCGGA (SEQ ID NO: 21) | TACACCTCGGGCCACTTG (SEQ ID NO: 22) |
| MUC2 | TAGTGTCCAGCTCCAGCATGA (SEQ ID NO: 10) | CCGGGCTGCTCATTGAGA (SEQ ID NO: 23) |
| CEACAM5 | TGGCTAGGATGGTCTCGAT (SEQ ID NO: 24) | GGACCTATGCCTGTTTTGTCT (SEQ ID NO: 25) |
| 18S rRNA | CGCTCCCAAGATCCAACTAC (SEQ ID NO: 26) | GTAATTCCAGCTCCAATAGCGTA (SEQ ID NO: 17) |

TABLE 3

Expression levels of SLC35D3, POSTN, KLK6, MUC2 and CEACAM5 mRNAs in primary CRC tumor, normal colon, normal colon epithelial cells, CRC cell lines, immune cell lines, a fibroblast cell line, CRC liver metastases and normal liver.

| | | | mRNA copies/18S rRNA unit | | | | |
|---|---|---|---|---|---|---|---|
| SOURCE | n | | SLC35D3 | POSTN | KLK6 | MUC2 | CEACAM5 |
| Primary CRC tumors | 56 | | 0.1* (0.04-0.4) | 9.7 (4.6-22.2) | 2.9 (0.9-8.5) | 1.1 (0.3-4.2) | 175 (107-283) |
| CRC cell lines | 1** | LS174T | 0 | 0 | 79 | 4.3 | 328 |
| | 1 | HT29 | 0.02 | 0 | 256 | 0.01 | 32 |
| | 1 | T84 | 0.7 | 0 | 316 | 0.5 | 33 |
| | 1 | HCT8 | 0.07 | 0 | 32 | 0.02 | 32 |
| | 1 | CaCo2 | 0.09 | 0.0009 | 0.4 | 0.04 | 3 |
| Normal Colon Tissue | 5 | | 0.02 | 5.9 | 0 | 9 | 222* |
| Normal Colon ECs | 5 | | 0.0009 | 0.2 | 0 | 32 | 300 |
| PBMCs | 1 | | 0.06 | 0 | 0 | 0 | 0 |
| Activated PBMCs | 1 | | 0 | 0 | 0 | 0 | 0 |
| T cell line | 1 | Jurcat | 0 | 0.009 | 0 | 0 | 0 |
| B cell lines | 1 | B6 + KR4 | 0 | 0 | 0 | 0 | 0 |
| Plasma cell line | 1 | U266 | 0 | 0.005 | 0 | 0 | 0 |
| Monocyte cell line | 1 | U937 | 0 | 0 | 0 | 0 | 0.005 |
| Granulocyte cell line | 1 | HL60 | 0 | 0 | 0 | 0 | 0 |
| Pre-erythrocyte cell line | 1 | K562 | 0.09 | 0.001 | 0 | 0 | 0 |
| Fibroblast cell line | 1 | FSU | 0 | 5.5 | 0 | 0.004 | 0.0002 |
| Livermetastasis | 2 | | 0.07 | 22.6 | 2 | 0.003 | 78 |
| Normal liver | 2 | | 0 | 2.3 | 0 | 0.00004 | 0.01 |

*Median and interquartile range from the 25$^{th}$ to the 75$^{th}$ percentile.
**Cell lines and PBMCs, mean of 3 determinations. ECs, purified epithelial cells; PBMCs, peripheral blood mononuclear cells; 0, <0.00001 mRNA copies/18S rRNA unit.

Application of Combined Biomarker mRNA Analysis for Predicting Probability of CRC-Death A clinical material of lymph nodes from 166 surgically treated patients with CRC representing all four TNM stages and with known CEACAM5 mRNA, KLK6 mRNA, MUC2 mRNA and 18S rRNA expression levels was analyzed for expression levels of SLC35D3 mRNA and POSTN mRNA. In total mRNA from more than 600 lymph nodes were analyzed. The mRNA values were normalized against 18S rRNA and expressed as mRNA copies/18S rRNA unit. Previous studies by our group have demonstrated that 18S rRNA is an excellent RNA species for normalization (Bas A. et al, Scand. J. Immunol., vol. 59, p. 566-573 (2004); Ohlsson L. et al. Int. J. Cancer, vol. 130, p. 1833-1843 (2012)). The node with the highest mRNA expression level was used to represent the patient in further analysis. This is in analogy with the present clinical practice that H&E positive nodes are considered informative, while H&E negative nodes are considered non-informative except in the case when all nodes are negative. FIG. 2 shows the result. The figure also shows the mRNA values for lymph nodes from non-CRC control patients and the dashed line indicates the highest value of this control group. Lymph nodes from stage III and IV patients displayed a larger fraction of nodes with mRNA values above the cut-off level than nodes from stage I or II patients [SLC35D3: stage I=18%, stage II=9%, stage III=25%, and stage IV=79%; POSTN: stage I=25%, stage II=13%, stage III=32%, and stage IV=69%].

The results from analysis of SLC35D3- and POSTN mRNA expression levels were used in combination with the known expression levels for CEACAM5-, KLK6- and MUC2 mRNA in the same nodes of the CRC patients (Ohlsson L et al. Br. J. Cancer, vol. 95, p. 218-225 (2006); Ohlsson L. Thesis, ISBN 978-91-7459-318-1 (2011); Ohlsson L. et al. Br. J. Cancer, vol. 107, p. 150-157 (2012)). Cut-off levels were determined for the 5 biomarkers as follows: The patients were ranked according to the biomarker expression level in the highest lymph node and then divided into five groups of equal number of patients. The groups were compared with respect to disease-free survival using Cox regression analysis. From this analysis, the cut-off level was defined as the mRNA expression level at the 8th decile because, for all five markers, the groups below the $8^{th}$ decile did not differ significantly in disease-free survival. Patients who died from causes other than CRC were considered as disease-free. Patients were divided into two groups, mRNA expression value above and mRNA expression value below the cut-off and for each group the mean survival time after surgery was calculated by cumulative survival analysis according to Kaplan-Meier and risk for recurrence of CRC estimated according to univariate Cox regression analysis. The result for the five biomarkers is shown in Table 4. As can be seen, mRNA values above the cut-off levels for all of them were correlated with poorer prognosis with highly significant P-values.

Determining the levels for all five biomarkers and combining the different measurements achieves further differentiation of the patient groups with respect to survival. In one embodiment of the invention the combined information derived from the biomarker analysis to predict survival after surgery is used as follows: For each highest lymph node the values for the biomarkers, SLC35D3, KLK6 and MUC2 is first divided by their corresponding CEACAM5 value. For SLC35D3/CEACAM5 and KLK6/CEACAM5 the ratios were then referred to one of two groups >0.00001 or <0.00001 (FIG. 3). The former group was assigned a value of 1 and the latter a value of 0. For MUC2/CEACAM5 the division was achieved at a ratio of 3.0 assigning nodes with values above 3.0 a value of 1 and below a value of 0 (FIG. 3). For POSTN the POSTN/18S rRNA ratio and the clinical cut-off (8.0 copies/18S rRNA unit; FIG. 2) were used to achieve the two groups, assigning values of 1 above the clinical cut-off and 0 for below. A formula, (Formula A: SLC35D3/CEACAM5+KLK6/CEACAM5+POSTN/18S rRNA−MUC2/CEACAM5) was used to classify each patient into one of five groups (formula result: −1, 0, +1, +2, +3) and cumulative survival analysis according to Kaplan-Meier was performed on these groups. The result is shown in FIG. 4. Five different curves are obtained. Group (−1) and (0) show good 3 and 5 years survival, group (+1) and (+2), relatively poor survival and group (+3) very poor survival (Table 5). The risk ratios calculated according to univariate Cox regression analysis, for groups (0), (+1), (+2) and (+3) in comparison to group (−1), is shown in Table 6.

In other embodiments of the invention the biomarker mRNA measurements were calculated in the same way as in Formula A except that in these formulas, e.g. Formula B to Formula E, one of the terms was systematically excluded. FIG. 5 shows the cumulative survival according to Kaplan-Meier calculated according to formula E. Table 5 summarizes 3 and 5 years survival for biomarker mRNA measurements as determined by the 5 formulas (Formula A to Formula E) and Table 6 summarizes the hazards ratios for biomarker mRNA measurements as determined by Formula A, B and C. Although useful information with respect to survival after surgery is generated by biomarker data treated according to formula B to formula E it is clear that treating the biomarker mRNA data according to Formula A is the most informative demonstrating that all of these biomarkers contribute to the result.

TABLE 4

Comparative analysis of average survival time and risk for recurrence of disease of CRC patients with biomarker (+) or biomarker (−) lymph nodes

| Biomarker | mRNA (copies/18S rRNA unit) Level | Survival time after surgery (months) Average | Difference vs marker (−) | P-Value | Risk for recurrence of CRC Hazard ratio | P-value |
|---|---|---|---|---|---|---|
| SLC35D3 (−) | <0.0059* | 103** | | | | |
| SLC35D3 (+) | >0.0059 | 54 | 49 | 0.002 | 2.48*** | 0.002 |
| POSTN (−) | <11.05 | 107 | | | | |
| POSTN (+) | >11.05 | 76 | 31 | 0.001 | 2.52 | 0.002 |
| KLK6 (−) | <0.0831 | 110 | | | | |
| KLK6 (+) | >0.0831 | 46 | 64 | <0.0001 | 4.01 | <0.0001 |
| MUC2 (−) | <0.0045 | 108 | | | | |
| MUC2 (+) | >0.0045 | 64 | 44 | 0.001 | 2.53 | 0.001 |
| CEA (−) | <4.2 | 112 | | | | |
| CEA (+) | >4.2 | 44 | 68 | <0.0001 | 4.67 | <0.0001 |

*The cut-off level is the $8^{th}$ decile of the patient population.
**Mean survival time after surgery as calculated by cumulative survival analysis according to Kaplan-Meier.
***Risk ratio as calculated according to univariate Cox regression analysis.

TABLE 5

Percentage of CRC patients that have died from cancer 3 and 5 years after surgery as determined by cumulative survival according to Kaplan-Meier. Comparison between patients classified into groups according to formula A, B, C, D and E.

| | Formula | | | | | | | | | |
|---|---|---|---|---|---|---|---|---|---|---|
| | A | B | C | D | E | A | B | C | D | E |
| Group | 3 years | | | | | 5 years | | | | |
| −1 | 7 | 10 | 5 | — | 10 | 14 | 15 | 12 | — | 18 |
| 0 | 10 | 13 | 14 | 9 | 10 | 20 | 26 | 21 | 15 | 19 |

TABLE 5-continued

Percentage of CRC patients that have died from cancer 3 and 5 years after surgery as determined by cumulative survival according to Kaplan-Meier. Comparison between patients classified into groups according to formula A, B, C, D and E.

| | Formula | | | | | | | | |
|---|---|---|---|---|---|---|---|---|---|
| | A | B | C | D | E | A | B | C | D | E |
| Group | | 3 years | | | | | 5 years | | | |
| +1 | 28 | 31 | 34 | 20 | 29 | 37 | 38 | 42 | 32 | 38 |
| +2 | 42 | 57 | 41 | 51 | 42 | 47 | 84 | 80 | 58 | 65 |
| +3 | 56 | — | — | 34 | — | 84 | — | — | 60 | — |

Formula A: [SLC35D3/CEACAM5 + POSTN/18S rRNA + KLK6/CEACAM5 – MUC2/CEACAM5] giving the groups –1, 0, +1, +2, +3
Formula B: [SLC35D3/CEACAM5 + POSTN/18S rRNA – MUC2/CEACAM5] giving the groups –1, 0, +1, +2
Formula C: [KLK6/CEACAM5 + POSTN/18S rRNA – MUC2/CEACAM5] giving the groups –1, 0, +1, +2
Formula D: [SLC35D3/CEACAM5 + KLK6/CEACAM5 + POSTN/18S rRNA] giving the group 0, +1, +2, +3
Formula E: [SLC35D3/CEACAM5 + KLK6/CEACAM5 – MUC2/CEACAM5] giving the groups –1, 0, +1, +2.

TABLE 6

Risk for recurrence of CRC after surgery as calculated according to univariate Cox regression analysis. Comparison between patients classified into groups according to formula A, B and C.

| | Formula A | | Formula B | | Formula C | |
|---|---|---|---|---|---|---|
| Group | Hazards ratio | P-value | Hazards ratio | P-value | Hazards ratio | P-value |
| –1 | * | | * | | * | |
| 0 | 1.33 | ns | 0.49 | Ns | 0.41 | ns |
| +1 | 3.15 | 0.028 | 2.34 | Ns | 3.3 | 0.008 |
| +2 | 3.64 | 0.021 | 5.56 | 0.001 | 6.59 | <0.0001 |
| +3 | 6.98 | 0.001 | | | | |

Formula A: [SLC35D3/CEACAM5 + POSTN/18S rRNA + KLK6/CEACAM5 – MUC2/CEACAM5] giving the groups –1, 0, +1, +2, and +3
Formula B: [POSTN/18S rRNA + SLC/CEACAM5 – MUC2/CEACAM5] giving the groups –1, 0, +1, +2
Formula C: [POSTN/18S rRNA + KLK6/CEACAM5 – MUC2/CEACAM5] giving the groups –1, 0, +1 and +2.

A Kit for Determination of Biomarker mRNAs

The invention also includes a kit for analysis of biomarker mRNA and 18S rRNA and transformation of raw data to clinically useful information as illustrated by formulas Formula A to Formula E.

In one embodiment of the invention the particular forward and reverse primers as well as probe sequences given in Table 1 are used in real-time quantitative RT-PCR. Quantitation is achieved by using specific copy standards (RNA) and 3' primers for reverse transcription with biomarker mRNA values normalized to content of 18S rRNA and/or content of CEACAM5 mRNA in the sample. Normalized values are allocated to one of two groups, either (1=high risk for recurrence) and (0=low risk for recurrence) according to the biomarker level with cut-off levels determined from analysis of a clinical material of lymph nodes from surgically treated CRC patients. Using a specifically designed algorithm the (1) and (0) values for each biomarker is transformed to an estimate of relative risk of cancer death, with a range –1, 0, +1, +2, +3, where –1 stands for the lowest risk and +3 for the highest risk, based on the formula: SLC35D3/CEACAM5+KLK6/CEACAM5+POSTN/18S rRNA–MUC2/CEACAM5.

In the embodiments of the invention as exemplified in FIGS. 4 and 5 and Tables 5 and 6 preferably only the information from the lymph node with the highest biomarker mRNA is of value. However, a number of patients have more than one lymph node harboring tumor cells. The methods according to the invention can also be used in this case, i.e. for differentiation between N1 and N2 stage patients, adding prognostic value.

Experimental Methods

General Methods

Bioinformatics Analysis—

Results from microarray gene expression analysis were analyzed by using Illumina Beadstudio software (version 3.3) for direct hybridization assays. Intensity data were normalized by Beadstudios cubic spline algorithm with subtracted background. Significant difference in expression was calculated using Beadstudio software Error Model Illumina Custom with multiple testing corrections using Benjamini and Hochberg False Discovery Rate (Reiner A. et al. Bioinformatics, vol. 19, p. 368-375 (2003)). Difference in gene expression was calculated as fold change, dividing the signal in the CRC samples of interest over average signal of controls.

Cell Lines and Peripheral Blood Mononuclear Cells—

The following established human cell lines were utilized: LS174T, HT29, T84, HCT8 and CaCo2 (all colon carcinomas), Jurkat and Molt-4 (T-cell lymphomas), B6 and KR4 (EBV-transformed B cell lines), U266 (plasmacytoma), U937 (monocyte-like cell line), K562 (erythroblastoid cell line), HL60 (granulocyte cell line), FSU (fibroblast cell line). Peripheral blood mononuclear cells (PBMCs) were isolated from peripheral blood of healthy adults by Ficoll-Isopaque gradient centrifugation. PBMCs were activated in vitro by incubation with the OKT3 monoclonal antibody (50 ng/ml) in HEPES-buffered RPMI 1640 supplemented with 0.4% human serum albumin. PBMCs from seven individuals were incubated with the stimulus in parallel cultures for 4, 7, 20, 48 and 72 hours, washed, pooled and RNA extracted.

Clinical Characteristics of the CRC Patients and Controls—

Surgery for treatment of CRC was carried out in 166 patients [81 men, 85 women, median age 72, (range 42-90) years]. Thirteen of the tumors were located in rectum and 153 in the colon. Seven of the rectal cancer patients received 25 Gy of preoperative radiotherapy. A locally radical tumor resection was carried out in all patients. The tumor differentiation grade was poor, moderate and high in 11, 145 and 10 tumors, respectively. Routine hematoxylin and eosin (H&E) staining was performed on 2,351 lymph nodes, giving a median of 13 (range 1-51) nodes per patient. According to the TNM classification, 30 patients were in stage I (T1-2N0M0), 74 in stage II (T3-4N0M0), 46 in stage III (anyTN1-2M0) and 16 in stage IV (anyTanyNM1). Thirty-four patients (4 in stage II, 19 in stage III and 11 in stage IV) received chemotherapy after surgery. The median follow-up time was 75 (range 33-147) months and no patient was lost at follow-up.

Controls included 18 men and 5 women [median age 25 years, (range 10-61)] undergoing surgery for ulcerative colitis (n=18), Crohn's colitis (n=3), rectal prolapse (n=1), and colon lipoma (n=1).

Informed consent was obtained from the patients and in one case his parents. The Research Ethics Committee of the Medical Faculty, Umeå University, Sweden approved the study.

Primary and Distant CRC Tumor and Normal Colon Tissue—

One hundred and thirteen samples from 85 primary CRC tumors were analyzed for biomarker mRNA levels (22 samples from 16 stage I patients, 44 samples from 35 stage II patients, 41 samples from 25 stage 11 patients, and 8 samples from 8 stage IV patients). Primary tumor stage distribution (pT1-pT4) was 2, 14, 55 and 13 respectively. The differentiation grade was poor in 11 tumors, moderate in 71 tumors and high in 3 tumors. One to four samples, approximately 0.5×0.5×0.5 cm in size, were collected from primary tumor specimens immediately after resection, snap-frozen, and stored at −70° C. until RNA extraction. Six normal colon samples, retrieved from the proximal or distal resection margin and two distant liver metastasis samples were collected and treated in the same way as the primary CRC tumors.

Epithelial Cells from Colon Tissue—

Colonic epithelial cells (ECs) were isolated from the normal colon mucosa at the resection margins as described (Fahlgren A. et al. Clin. Exp. Immunol., vol. 131, p. 90-101 (2003)).

Lymph Nodes—

Lymph nodes were retrieved from the resected specimens and bisected with separate, sterile knives. One half of each node was fixed in 10% buffered formalin for routine H&E-staining. The other half was snap frozen in liquid nitrogen and stored at −70° C. until RNA extraction. From CRC patients, 503 lymph nodes (91, 253, 107 and 52 nodes from stage I-IV patients, respectively) were collected. A median of 2 (range 1-15) lymph nodes was obtained per patient.

From control patients, 108 lymph nodes (82, 9, 13 and 4 nodes from ulcerative colitis, Crohn's colitis, colon lipoma and rectal prolapse patients, respectively) were collected.

RNA Isolation—

Total RNA was extracted from lymph nodes, normal and tumor colon tissues, colon epithelial cells, PBMCs and cell lines using the acid guanidine phenol chloroform method (Chomczynski P and Sacchi N. Analyt. Biochem., vol. 162, p. 156-159 (1987)) by adding 0.5 ml of a solution containing 4 M guanidinium thiocyanate, 25 mM sodium citrate (pH 7.0), 0.5% sarcosyl and 0.1 M 2-mercaptoethanol per 25 mg tissue and up to $2.5 \times 10^6$ cells in the first homogenization step. Extracted RNA was dissolved in RNAse-free water containing the RNAse inhibitor RNAsin (1 U/μl; Promega, Madison, Wis.). The RNA concentration was measured in a NanoDrop ND-1000 Spectrophotometer (NanoDrop Technologies) and for bead microarray analysis the integrity of the RNA was analyzed in a 2100 Bioanalyzer using an RNA nano assay (Agilent Technologies).

Preparation of RNA Copy Standards—

Total RNA from a primary CRC tumor, two lymph nodes from two patients with CRC and the colon carcinoma cell lines LS174T and T84 were used as starting material for copy standard preparations. The primers used for RT-PCR are given in Table 2. The PCR products, which include the respective sequences amplified in quantitative RT-PCR, were cloned, sequenced and used as template for in vitro transcription with T7 polymerase/RiboProbe In Vitro Transcription Systems (Promega). Linearized DNA, 3-7 μg, was used in large-scale synthesis reactions carried out at 37° C. for 2-3 hr. The reaction products were then treated with 1 U/μg of RNase-free DNase (Promega) for 30-40 min at 37° C. followed by extraction with phenol: chloroform: isoamylalcohol (25:24:1) and chloroform: isoamylalcohol (24:1). RNA was precipitated with 2.5 volumes of 99.5% ethanol and 0.5 volumes of 7.5 M ammonium acetate at −70° C. for at least one hr. DNase treatment was repeated at least twice. Finally the copy standards were checked by RT-PCR and PCR to evaluate the content of DNA, which proved to be less than 0.2% for all of them. Concentration of the transcripts was calculated on the basis of the $OD_{260}$ value, the molecular weight of the transcript and Avogadro's number. The standards were finally diluted to $10^8$ copies/μl.

Real-Time qRT-PCR—

Real-time qRT-PCR assays with RNA copy standards were constructed for SLC35D3, POSTN, KLK6, CEACAM5, and MUC2 using the Tacman EZ RT-PCR technology (Applied Biosystems Foster City Ca). Primer and probe sequences are shown in Table 1. The RT-PCR profile was 49° C. for 2 min, 59° C. for 30 min, 94° C. for 5 min, followed by 45 cycles of 93° C. for 20 sec and 61° C. for 1 min. Serial dilutions of the respective RNA copy standard at concentrations from $10^3$ to $10^8$ copies/g were included in each analysis. All qRT-PCR analyses were carried out in triplicates. Emission from released reporter dye was monitored by the ABI Prism 7900 Sequence Detection System (Perkin-Elmer, Wellesley, Ma). For normalization of mRNA levels, the concentration of 18S rRNA was determined in each sample by real-time qRT-PCR according to the manufacturer's protocol (Applied Biosystems) or by use of primers and probe given in Table 1 (SEQ ID NO: 16-18) and copy standard prepared by using the primers given in Table 2 (SEQ ID NO: 26,17). Results were expressed as mRNA copies per unit of 18S rRNA or as RNA copies per copy of 18S rRNA in both cases yielding directly comparable levels of biomarkers.

Statistical Analysis—

Differences in disease free survival and risk for recurrent disease after surgery between patients groups were calculated according to Kaplan-Meier survival model in combination with the log rank test and univariate Cox regression analysis. Differences in survival time and hazards ratios with a P value <0.05 were considered to be statistically significant. The software utilized was SPSS (version 18).

The invention claimed is:

1. A kit, the kit comprising: nucleic acid primers and nucleic probes for determination of gene expression levels of genes SLC35D3 and POSTN to determine metastatic potential and/or tumor aggressiveness in a subject diagnosed with colorectal cancer wherein the primers and probes comprise (a) SEQ ID NO: 1-2 and 3, (b) SEQ ID NO: 4-5 and 6, or (c) a combination of (a) and (b) and wherein the probes contain a dye.

2. The kit according to claim 1, comprising further nucleic acid primers and probes for determination of gene expression levels of gene KLK6, wherein the probes contain a dye.

3. The kit according to claim 1, comprising further nucleic acid primers and probes for determination of gene expression levels of gene MUC2, wherein the probes contain a dye.

4. The kit according to claim 1, comprising further nucleic acid primers and probes for determination of gene expression levels of gene MUC2, wherein the probes contain a dye.

5. The kit according to claim 1, comprising further nucleic acid primers and probes for determination of gene expression levels of genes KLK6, MUC2, and CEACAM5.

6. The kit according to claim 1, further comprising mRNA, RNA and/or DNA copy standards.

* * * * *